US012653635B2

(12) United States Patent　　(10) Patent No.:　US 12,653,635 B2
Bernhard et al.　　　　　　　　(45) Date of Patent:　Jun. 16, 2026

(54) MANIPULATION DEVICE

(71) Applicant: KATHOLIEKE UNIVERSITEIT LEUVEN, Leuven (BE)

(72) Inventors: Felix Bernhard, Lilienthal (DE); Mouloud Ourak, Leuven (BE); Omar Al-Ahmad, Heverlee (BE); Jonas Smits, Korbeek-Lo (BE); Emmanuel B. Vander Poorten, Mechelen (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 1256 days.

(21) Appl. No.: 17/274,528

(22) PCT Filed: Sep. 10, 2019

(86) PCT No.: PCT/EP2019/074145
§ 371 (c)(1),
(2) Date: Mar. 9, 2021

(87) PCT Pub. No.: WO2020/053233
PCT Pub. Date: Mar. 19, 2020

(65) Prior Publication Data
US 2021/0307854 A1　　Oct. 7, 2021

Related U.S. Application Data

(60) Provisional application No. 62/765,729, filed on Sep. 10, 2018.

(30) Foreign Application Priority Data

Sep. 11, 2018　　(GB) ..................................... 1814750

(51) Int. Cl.
*A61B 34/00*　　　(2016.01)
*A61B 17/00*　　　(2006.01)
(Continued)

(52) U.S. Cl.
CPC ........ *A61B 34/76* (2016.02); *A61B 17/00234* (2013.01); *A61B 34/30* (2016.02);
(Continued)

(58) Field of Classification Search
CPC ........... A61B 1/00103; A61B 1/00135; A61B 1/00137; A61B 1/0052; A61B 2034/301;
(Continued)

(56) References Cited

U.S. PATENT DOCUMENTS 2,143,985 A * 1/1939 Kellems ................. H01R 13/58
29/283
2,352,391 A * 6/1944 Kitselman ............... F16G 11/12
138/123
(Continued)

FOREIGN PATENT DOCUMENTS

CN　　　201777776 U　　3/2011
DE　　　20213015 U1　　12/2003
(Continued)

OTHER PUBLICATIONS

Brimathveeravalli et al., "Design and Fabrication of a Robotic Mechanism for Remote Steering and Positioning of Interventional Devices", The International Journal of Medical Robotics and Computer Assisted Surgery, vol. 6, Feb. 4, 2010, pp. 160-170.
(Continued)

*Primary Examiner* — Scott J Medway
(74) *Attorney, Agent, or Firm* — Workman Nydegger

(57) ABSTRACT

A gripper for manipulation of an elongate member includes a flexible sleeve for receiving the elongate member, the sleeve extends along a sleeve axis and has first and second opposite ends; a first clamping element is configured to receive and removably couple to the first end of the sleeve; and a second clamping element is configured to receive and removably couple to the second end of the sleeve. The sleeve
(Continued)

has a first width at a first location when the first and second clamping elements have a first spacing along the sleeve axis and a second width at the first location when the first and second clamping elements have a second spacing along the sleeve axis which is less than the first spacing.

14 Claims, 65 Drawing Sheets

(51) Int. Cl.
  *A61B 34/30* (2016.01)
  *A61B 46/10* (2016.01)
(52) U.S. Cl.
  CPC .... *A61B 46/10* (2016.02); *A61B 2017/00327* (2013.01); *A61B 2017/00477* (2013.01); *A61B 2034/301* (2016.02)
(58) Field of Classification Search
  CPC .......... A61B 34/30; A61B 2017/06185; A61B 17/221; F16B 7/04; F16B 2/06; F16B 7/0413; F16B 7/0406; A61M 2025/0206; A61M 2025/024; A61M 25/02; A61M 2025/0253; A61M 25/0113; A61M 25/013; F16L 3/00; Y10T 403/45; Y10T 24/39; Y10T 24/3996; Y10T 24/1397; F16G 11/03; Y10S 128/26; Y10S 16/12; D04C 1/06; D04C 1/12
  See application file for complete search history.

(56) References Cited

U.S. PATENT DOCUMENTS

| | | | | |
|---|---|---|---|---|
| 2,434,358 | A | 1/1948 | Frank | |
| 2,740,178 | A * | 4/1956 | Kellems | H02G 1/081 294/86.42 |
| 3,033,502 | A * | 5/1962 | Silver | A01K 97/10 248/314 |
| 3,122,806 | A * | 3/1964 | Lewis | F16G 11/103 174/79 |
| 3,291,507 | A * | 12/1966 | Clay | F16L 3/00 285/305 |
| 3,368,564 | A * | 2/1968 | Selix | A61M 25/02 248/205.3 |
| 3,599,913 | A * | 8/1971 | DiPalma | F16L 3/00 403/204 |
| 3,975,919 | A | 8/1976 | Harrison | |
| 4,368,910 | A * | 1/1983 | Fidrych | G02B 6/545 24/115 N |
| 4,509,877 | A * | 4/1985 | Sobin | F16C 1/262 403/41 |
| 4,604,821 | A * | 8/1986 | Moser | A01K 91/047 87/8 |
| 5,147,322 | A * | 9/1992 | Bowen | A61M 25/02 128/DIG. 26 |
| 5,295,323 | A * | 3/1994 | Fasulkey | A01M 23/24 43/87 |
| 5,382,239 | A * | 1/1995 | Orr | A61M 25/02 604/177 |
| 5,397,323 | A | 3/1995 | Taylor et al. | |
| 5,476,493 | A * | 12/1995 | Muff | A61N 1/057 607/119 |
| 5,555,881 | A * | 9/1996 | Rogers | A61M 25/02 128/207.14 |
| 5,653,232 | A * | 8/1997 | Rogers | A61M 16/0488 128/207.14 |
| 5,848,453 | A * | 12/1998 | Racodon | B25G 3/00 16/431 |
| 6,471,268 | B1 * | 10/2002 | Stenstrom | F16L 1/06 16/431 |
| 6,830,545 | B2 * | 12/2004 | Bendall | A61B 1/00052 600/102 |
| 6,981,945 | B1 * | 1/2006 | Sarvazyan | A61B 1/31 606/1 |
| 7,214,230 | B2 | 5/2007 | Brock et al. | |
| 7,478,794 | B1 * | 1/2009 | Gohlke | B66C 1/42 254/134.3 R |
| 8,052,621 | B2 * | 11/2011 | Wallace | A61B 5/6885 600/587 |
| 8,209,899 | B2 * | 7/2012 | Klein | A01K 91/047 43/43.1 |
| 8,333,689 | B2 * | 12/2012 | Okamoto | A61B 1/01 600/102 |
| 8,388,518 | B2 * | 3/2013 | Sarvazyan | A61B 1/00147 600/101 |
| 8,784,379 | B2 * | 7/2014 | Akitomo | A61M 25/00 604/117 |
| 9,072,871 | B2 * | 7/2015 | Spinoza | A61M 25/02 |
| 9,630,817 | B2 * | 4/2017 | Vogt | F16D 63/008 |
| 10,695,533 | B2 | 6/2020 | Deboeuf et al. | |
| 10,862,289 | B2 * | 12/2020 | Diop | H02G 15/115 |
| 11,013,394 | B2 * | 5/2021 | Thornton | A61B 1/00101 |
| 11,248,973 | B2 * | 2/2022 | Hine | G01L 5/0033 |
| 11,278,703 | B2 * | 3/2022 | Kokish | A61M 25/0113 |
| 11,285,296 | B1 * | 3/2022 | Benz | A61M 25/0662 |
| 11,464,396 | B2 * | 10/2022 | Yahagi | A61B 1/00154 |
| 11,596,773 | B2 * | 3/2023 | Sorensen | A61M 5/14276 |
| 11,628,277 | B1 * | 4/2023 | Carroccio | A61B 1/0014 604/93.01 |
| 12,082,779 | B2 * | 9/2024 | Yahagi | A61B 1/00071 |
| 12,233,223 | B2 * | 2/2025 | Katz | A61M 25/02 |
| 2003/0212308 | A1 * | 11/2003 | Bendall | A61B 1/00052 600/102 |
| 2006/0217687 | A1 * | 9/2006 | Bakos | A61B 5/416 606/1 |
| 2008/0147011 | A1 * | 6/2008 | Urmey | A61N 1/0551 607/116 |
| 2009/0026682 | A1 * | 1/2009 | Smith | A61B 1/00128 269/216 |
| 2009/0142132 | A1 * | 6/2009 | Klein | A01K 91/12 403/301 |
| 2009/0194970 | A1 * | 8/2009 | Yeh | B60D 1/28 280/483 |
| 2009/0247827 | A1 * | 10/2009 | Secrest | A61B 1/0014 600/131 |
| 2009/0287053 | A1 * | 11/2009 | Okamoto | A61B 1/00142 600/139 |
| 2011/0065991 | A1 * | 3/2011 | Sarvazyan | A61B 1/31 600/131 |
| 2012/0024119 | A1 * | 2/2012 | Aldy | F16G 11/02 29/419.1 |
| 2013/0035537 | A1 * | 2/2013 | Wallace | A61B 34/30 604/95.01 |
| 2015/0112141 | A1 * | 4/2015 | Oginski | A61B 1/00195 600/136 |
| 2015/0148816 | A1 | 5/2015 | Govari et al. | |
| 2016/0158523 | A1 * | 6/2016 | Helm | A61M 39/162 604/513 |
| 2016/0296105 | A1 * | 10/2016 | Ramsey | A61B 1/00154 |
| 2017/0326338 | A1 | 11/2017 | Watson | |
| 2019/0008543 | A1 * | 1/2019 | Scoggins | A61B 17/320068 |

FOREIGN PATENT DOCUMENTS

| | | | | |
|---|---|---|---|---|
| GB | 2456325 | A * | 7/2009 | A61M 25/02 |
| GB | 2520332 | A | 5/2015 | |
| WO | 91/02179 | A1 | 2/1991 | |

OTHER PUBLICATIONS

Search Report from corresponding GB Application No. GB1814750. 4, Feb. 15, 2019.

(56) References Cited

OTHER PUBLICATIONS

International Search Report and Written Opinion from corresponding PCT Application No. PCT/EP2019/074145, Jan. 17, 2020.

* cited by examiner

1100

1110

1115

1000

MANIPULATION DEVICE

FIELD OF THE INVENTION

The present invention relates to devices and systems for manipulating elongate members.

BACKGROUND OF THE INVENTION

Minimally Invasive Surgery (MIS) is taking in an increasingly important role in modern surgery. Compared to the large incisions used in open surgery, incisions are small in MIS. Surgeons pass long and slender instruments and operate with them through these small incisions.

Due to reduced invasiveness, patients which were not considered yet for treatment e.g. due to high peri-operative risks, may now be treated. For example in cardiovascular diseases (CVD), catheter-based interventions can extend the range of patients able to receive interventional CVD treatment to age groups dominated by co-morbidity and unacceptable risks for open surgery.

However, minimizing access incisions gives rise to the increased complexity of manipulation of the instruments and anatomical targets.

The loss of direct access to the anatomy, lack of haptic feedback and poor visualization of the surgical site can make the intervention less intuitive. In catheter-based interventions, steering compliant catheters through a fragile cardiovascular system, under the presence of slack, friction, deformation and disturbances such as induced by physiological motion, is a complex and demanding task.

Robotic steering of tubular structures such as endoscopes, needles, catheters or guidewires is complex because can be difficult to grasp such fragile devices. For example a catheter may be held in storage liquid and may be required to remain sterile (U.S. patent application Ser. No. 15/580,700 Robotic method for driving a catheter and a catheter guide, 2018). Increasing the gripping pressure to prevent slip may damage the instruments. Continued use of a damaged instrument, for example if damage is undetected, can put the patient's health at risk.

Existing systems for driving tubular structures can be classified into systems relying on one or more sets of rollers, systems making use of translational guides or systems that rely on sets of driving belts.

Roller-based systems such as that described in U.S. Pat. No. 5,397,323 A1, 2017 rely on friction and more in particular on the frictional contact between one or more so-called friction wheels and the tubular body to drive the said tubular body.

If the tubular device meets resistance, the resistance can be overcome by increasing the contact pressure between the friction wheels and the tubular structure. This risks damage to the tubular structure and any components inside the structure such as sensors or guide wires. Alternatively the tubular structure can be retracted and a new route searched for alongside the resistance. This increases the duration of the operation. The robotic catheter driver can be bypassed and manual operation undertaken. This introduces risks such as lack of precision of a manual operator.

Srimathveeravalli, G., Kesavadas, T., & Li, X. (2010) "Design and fabrication of a robotic mechanism for remote steering and positioning of interventional devices", The International Journal of Medical Robotics and Computer Assisted Surgery, 6 (2), 160-170 describes a spring-loaded roller based system.

A challenge with roller-based and spring-loaded roller-based systems exists in the need to allow easy exchange of tubular structures or to allow driving tubular structures with different outer diameters.

U.S. Pat. No. 7,214,230 B2 describes a catheter drive system that relies on a linear guide and linear drive system. When large distances are to be traversed this means that the linear guide must be at least equally long, resulting in a bulky drive system.

Other limitations of existing systems include difficulty in achieving alignment of the tubular structure with respect to the longitudinal axis of the apparatus. This means it can be difficult to cause the tubular structure to rotate properly about its own axis. Existing systems do not allow for easy installation and removal of a gripping element for gripping the tubular member so that this can be cleaned.

Systems like the Magellan™ from Hansen Medical make use of a pair of conveyor belts between which the tubular structure is clamped.

The pair of conveyor belts does not provide a complete closure of the tubular structure. This means that the tubular structure may wander off-axis, may drift in orientation or may take on an non-straight shape. As a consequence additional means are needed to constrain the tubular structure. Large stress concentrations or buckling can occur at the locations where the tubular structure is constrained by these additional means.

Existing systems can struggle to manipulate complex tubular structures such as a structure having a varying diameter, cross-sectional shape, and compliance.

Therefore there is a need for a system for manipulating a wide range of tubular structures that provides a stable grip with proper enclosure, that does not risk damage to the tubular structure through gripping, and that allows a gripping element to be easily replaced.

SUMMARY

It is an object of embodiments of the present invention to provide a gripper and a system capable of translating an elongate member with precision, reliably and safely. It is a further object of the present invention to provide a system capable of rotating an elongate member with precision, reliably and safely.

It is an advantage of embodiments of the present invention that it allows for sterile operation due to the possibility of sideways placement of the elongated member, e.g. catheter, by opening one or both of the clamping elements thus providing an opening in the circumference of one or both of the clamping elements. Sterile operation is especially useful, and often crucial, for medical applications.

It is an advantage of at least some embodiments of the present invention to provide a gripper and a system capable of manipulating elongate members of varying compliance, cross-sectional shape, and diameter.

It is an advantage of at least some embodiments of the present invention to provide a gripper which allows an elongate member to be easily and quickly installed and removed.

It is an advantage of at least some embodiments of the present invention to allows establishing a reliable grasp or grip of the elongate member that can be easily released, initiated, and regulated in intensity and where the intensity is typically set or regulated such as to ensure an acceptable pressure or stress concentration upon gripping the elongate member such that the integrity of the elongate member can be guaranteed.

It is an advantage of at least some embodiments of the present invention that the described method offers a theoretical infinite stroke allowing unlimited propulsion or retraction of the elongate member along the first axis. Whereby theoretical infinite stroke means that in principle an infinitely long elongate member can be driven, and in practice, that a elongate member can be driven over the length of the elongate member along the first axis, independent of the length of the elongate member or at least the part of the structure that is tubular.

It is an advantage of at least some embodiments of the present invention that the invention can be combined with other drive systems or other embodiments of the invention to drive a plurality of elongate members simultaneously and/or to control different motion degrees-of-freedom of the said elongate member. For example, the apparatus can be combined with another drive system that controls the distal tip of the said elongate member for example by controlling a cable or wire that is connected at the distal tip of the elongate member and that when operated causes a bending motion of the said distal tip.

It is an advantage of at least some embodiments of the present invention to provide a method to drive an elongate member. The method allows linear translation of the elongate member in a direction that coincides locally with the longitudinal axis of the said elongate member but also allows controlled rotation of the elongate member about an axis that coincides with this local longitudinal axis.

Embodiments of the present invention are particularly useful for driving fragile elongate members such as optical fibers or in a surgical context endoscopes, catheters, needles or guidewires. A particularly useful feature of embodiments of the present invention to provide a distributed and controllable contact with the fragile elongate member such that large stress concentrations can be avoided. Thanks to the distributed contact between the gripper and the driven structure a reliable grip can be established and slip can be avoided. This allows the position and orientation of the elongate member to be controlled with improved precision.

Embodiments of the present invention provide a compact device or apparatus that is capable of delivering an unrestricted translational stroke. The modular nature of embodiments of the present invention allows for an easy exchange of the driven elongate member and for an easy adjustment to drive elongate members with very different diameters. The easy exchange simplifies for example ensuring safe operation under sterile conditions.

The modular nature of embodiments of the present invention further allows for easy combination of multiple embodiments to drive a plurality of elongate members. For example a combination of such drives could be used to simultaneously drive a guidance catheter, a guidewire and a working catheter. For example in some embodiments the different elongate members are driven sequentially, where interface components are exchanged to switch between elongate members to be driven.

According to a first aspect of the present invention, there is provided a gripper for manipulation of an elongate member, comprising a flexible sleeve for receiving the elongate member, the sleeve extending along a sleeve axis and having first and second opposite ends; a first clamping element configured to receive and removably couple to the first end of the sleeve; and a second clamping element configured to receive and removably couple to the second end of the sleeve. The sleeve has a first width at a first location when the first and second clamping elements have a first spacing along the sleeve axis and a second width at the first location when the first and second clamping elements have a second spacing along the sleeve axis which is less than the first spacing. The first width is different to the second width.

At least one of the first clamping element and the second clamping element is adapted for being arranged in an open configuration, e.g. when the elongate member is to be positioned, providing at least sideways access for inserting the sleeve sideways in a direction not along a sleeve axis direction in said at least one clamping element, and for alternatively, when in use, being arranged in a closed configuration wherein the sleeve is clamped.

The gripper may be adapted for manipulating an elongate medical member such as for example a catheter, a colonoscope, an endoscope, etc.

In some embodiments, both the first and the second clamping elements are adapted for being arranged in an open configuration, e.g. when the elongate member is to be positioned, providing at least sideways access for inserting the sleeve sideways in a direction not along a sleeve axis direction in said clamping element, and for alternatively, when in use, being arranged in a closed configuration wherein the sleeve is clamped.

The open configuration may be a configuration wherein the clamping element comprises an opening along its circumference.

The sleeve may be configured to engage with the surface of the elongate member for a specified spacing of the first and second clamping elements.

The first clamping element may have an open configuration for receiving the sleeve and a closed configuration for securing the first end of the sleeve, and the second clamping element may have an open configuration for receiving the sleeve and a closed configuration for securing the second end of the sleeve.

The first clamping element may be configured to receive the sleeve in a direction substantially perpendicular to the sleeve axis.

The second clamping element may be configured to receive the sleeve in a direction substantially parallel to the sleeve axis.

The first width may be greater than the second width.

The first width may be less than the second width.

The first clamping element may be rotatable about the sleeve axis relative to the second clamping element.

The second clamping element may be rotatable about the sleeve axis relative to the first clamping element.

The first clamping element may have the form of a cylindrical shell.

The first clamping element may comprise an aperture in the shell for receiving the sleeve, the aperture extending parallel to the axis of the cylindrical shell.

The second clamping element may have the form of a cylindrical shell.

The second clamping element may comprise an aperture in the shell for receiving the sleeve, the aperture extending parallel to the axis of the cylindrical shell.

The sleeve may comprise a first collar at the first end of the sleeve and a second collar at the second end of the sleeve, wherein the first clamping element is configured to couple to the first collar and the second clamping element is configured to couple to the second collar.

The elongated body may comprise a catheter.

The elongated body may comprise an endoscope.

According to a second aspect of the present invention there is provided a device for manipulation of an elongate member, the device comprising at least one gripper according to the first aspect and a driving element coupled to the first clamping element and to the second clamping element.

The driving element may be configured to control the spacing of the first clamping element and the second clamping element along the sleeve axis.

The driving element may be configured to rotate the first clamping element about the sleeve axis.

The driving element may be configured to rotate the second clamping element about the sleeve axis.

The device may comprise at least two grippers according to the first aspect, the at least two grippers being spaced apart along the axis of the sleeves comprised in the at least two grippers.

The device may comprise at least one sensor.

The device may comprise a control element configured to receive data from the sensor and to provide a control signal to the driving element in dependence upon the received data.

The device may comprise a sterile barrier for separating the elongate member.

According to a third aspect of the present invention there is provided a gripper according to the first aspect or a device according to the second aspect, and a driving module configured to rotate and/or translate the gripper or the device.

According to a fourth aspect of the present invention there is provided apparatus for manipulating a first elongate body and a second elongate body coaxial with the first elongate body, the apparatus comprising a first device according to the second aspect or a first apparatus according to the third aspect configured to manipulate the first elongate body, and a second device according to the second aspect or a first apparatus according to the third aspect configured to manipulate the second elongate body.

The first elongate body may be a catheter and the second elongate body may be a guide wire.

BRIEF DESCRIPTION OF THE DRAWINGS

Certain embodiments of the present invention will now be described, by way of example, with reference to the accompanying drawings, in which:

FIG. 7b illustrates the relation between braid contraction and dilation as a function of initial braid angle for a braided sleeve as one embodiment of a sleeve comprised in a gripper according to embodiments of the present invention, for a relatively large initial braid angle as compared to FIG. 7a;

FIG. 20, including

FIG. 36b is a plot of tracking error for FIG. 36a;

Figure 1:
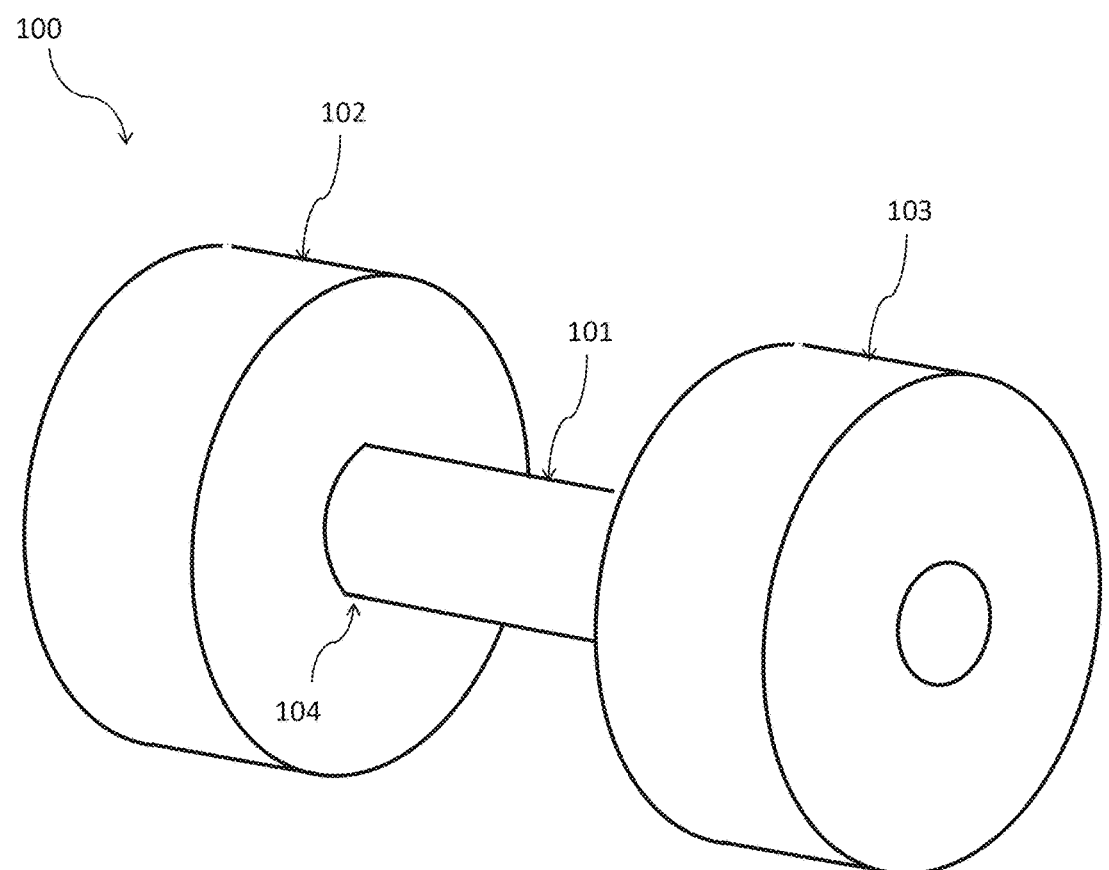
FIG. 1 is a schematic perspective view of a gripper according to embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF CERTAIN EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention is based on the insight that a sleeve having a diameter than can be varied by translating the end points of the sleeve can be used to grip and manipulate an elongate element. By translating and/or rotating the ends of the sleeve, the sleeve can engage with the elongate element and transfer the translation and/or rotation to the elongate element. This can allow precision manipulation, for example translation and/or rotation, of the elongate element. By providing the sleeve as an element which is removably couplable to elements for clamping and actuating the sleeve ends, assembly of the elongate member within the sleeve can be simplified, as the sleeve can simply be slid onto the elongate member and then coupled to the clamping elements.

Referring to FIG. 1, a gripper 100 according to embodiments of the present invention is shown. The gripper 100 comprises a flexible sleeve 101, a first clamping element 102, and a second clamping element 103.

Figure 2A:
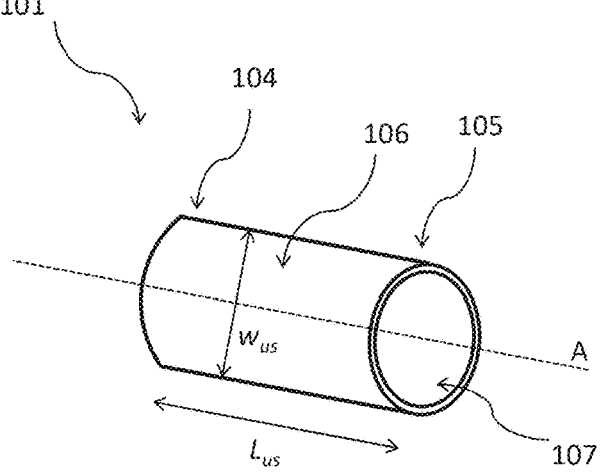
FIG. 2a is a schematic perspective view of a sleeve comprised in a gripper according to embodiments of the present invention.

Referring also to FIG. 2a, the flexible sleeve 101 has a generally tubular form, extending between a first end 104 and a second end 105 spaced apart from the first end 104 along a sleeve axis A. The flexible sleeve 101 has an outer surface 106 and an inner surface 107. The sleeve 101 has an unstretched length $L_{us}$ when no tension is applied to the sleeve 101. The sleeve 101 has an unstretched width $w_{us}$ when no tension is applied to the sleeve 101.

Figures 2B, 3A:
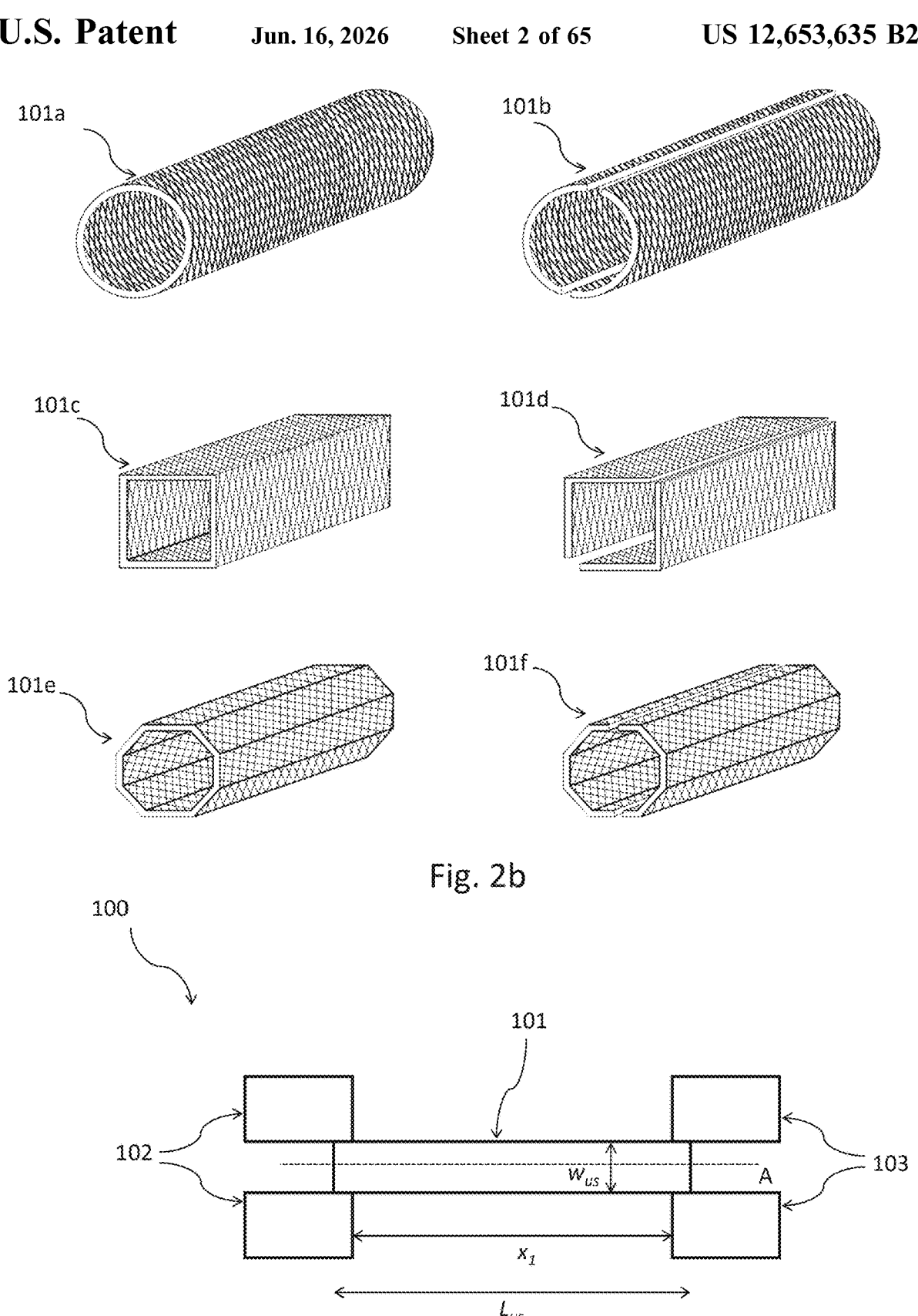
FIG. 2b illustrates various alternative sleeves which may be comprised in a gripper according to embodiments of the present invention.
FIG. 3a is a cross-sectional view of a gripper according to embodiments of the present invention with a first spacing between clamping elements.

However, referring to FIG. 2b, the flexible sleeve 101 is not limited to a closed tubular form or a cylindrical form and may take, for example, a tubular form 101a with a circular cross-section and a closed curved surface; a tubular form 101b with a circular cross-section and a curved surface having a longitudinal aperture; a tubular form 101c with a square or rectangular cross section; a tubular form 101d with a square or rectangular cross section having a longitudinal aperture; a tubular form 101e with an octagonal cross section; a tubular form 101f with an octagonal cross section having a longitudinal aperture;

Referring again to FIG. 1, the first clamping element 102 is configured to receive and removably couple to the first end 104 of the sleeve 101. The second clamping element 103 is configured to receive and removably couple to the second end 105 of the sleeve 101.

Figure 3B:
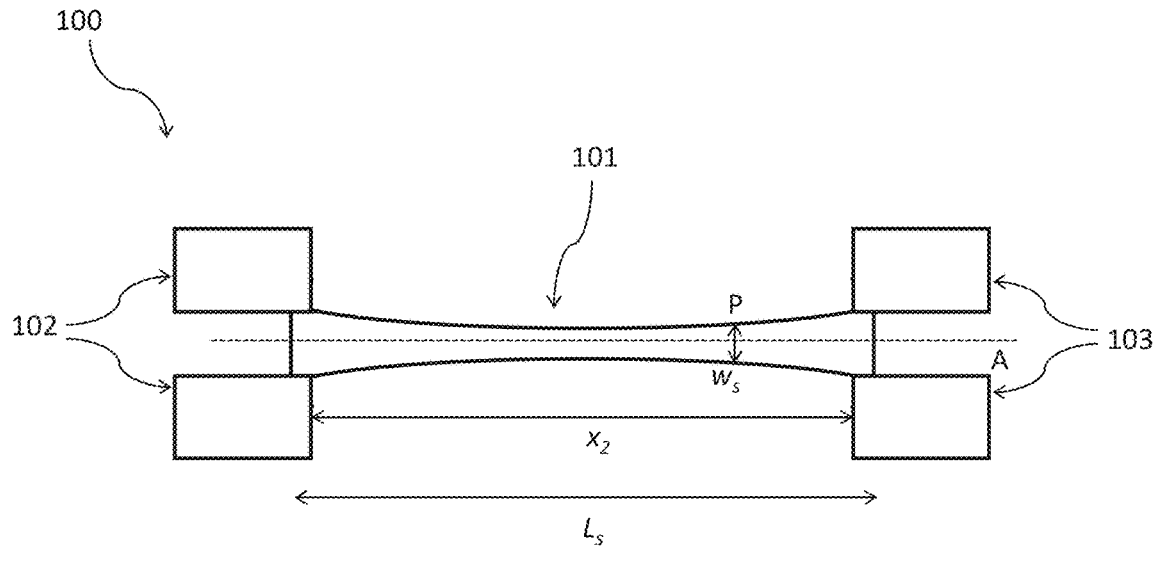
FIG. 3b is a cross-sectional view of a gripper according to embodiments of the present invention with a second spacing between clamping elements.

The first clamping element 102 and the second clamping element 103 can be translated along the sleeve axis A relative to each other. When the sleeve 101 is coupled to the first clamping element 102 and the second clamping element 103, relative movement of the first and second clamping elements 102, 103 along the sleeve axis A causes a change in tension applied to the sleeve 101. Referring to FIG. 3a, the first clamping element 102 and the second clamping element 103 have a spacing $x_1$ along the sleeve axis A such that no tension is applied to the sleeve 101 in a direction parallel to the sleeve axis A. The length of the sleeve 101 is then equal to its unstretched length $L_{us}$ and the width of the sleeve 101 is equal to its unstretched width $w_{us}$. Referring to FIG. 3b, the first clamping element 102 and the second clamping element 103 have a spacing $x_2$ along the sleeve axis A which is greater than the spacing $x_1$. The sleeve 101 is stretched along its axis and has a stretched length $L_s$. The width $w_s$ of the sleeve 101 at a point P between the first end 104 and the second end 105 is less than the unstretched width $w_{us}$.

Figure 4:
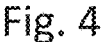
FIG. 4 is a cross-sectional view of a gripper according to embodiments of the present invention and an elongate member held by the gripper.

Referring to FIG. 4, the gripper 100 is configured to receive an elongate member 120 such that the elongate member 120 extends through the sleeve 101 and the first and second clamping elements 102, 103 respectively. At an engagement spacing $x_s$ of the first clamping element 102 and the second clamping element 103, at least part of the inner surface 107 of the sleeve 101 engages circumferentially with the surface of the elongate member 120, that is, the elongate member 120 is gripped around its circumference along a length which is within the sleeve 101. The engagement spacing can depend on multiple factors such as the diameter of the elongate member, the unstretched width of the sleeve, the unstretched length of the sleeve, the flexibility of the sleeve. The gripper 101 can then be translated and/or rotated and the elongate member 120 will be translated and/or rotated along with the gripper 101. This provides a mechanism for precision manipulation of the elongate member 120.

Advantageously, the elongate member 120 can be assembled to the gripper 100 in various ways. For example, the elongate member 120 can be threaded through the first clamping element 102, the sleeve 101, and the second clamping element 103 without removal of the sleeve 101 from the gripper 100.

Figure 5A:
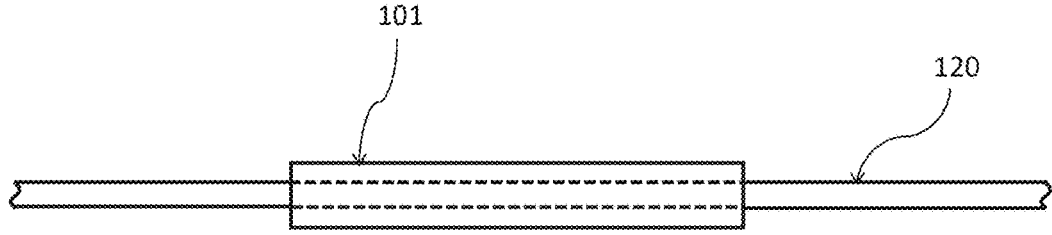
FIG. 5a is a cross-sectional view of a first step in a process of assembling an elongate member to a gripper according to embodiments of the present invention.
Figures 5B, 6:
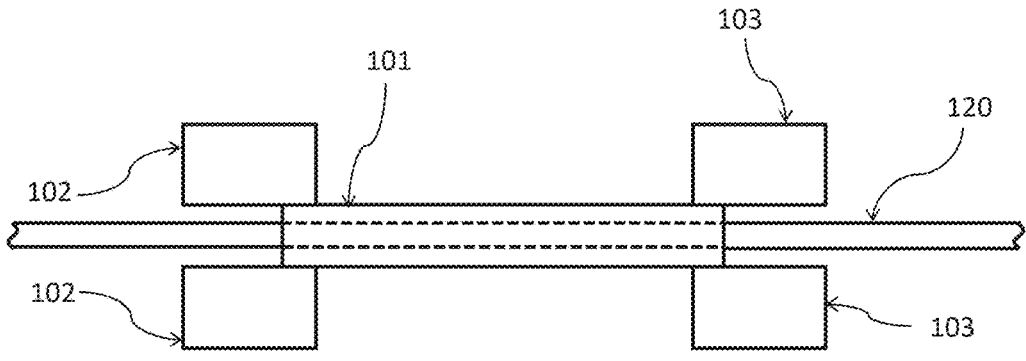
FIG. 5b is a cross-sectional view of a second step in a process of assembling an elongate member to a gripper according to embodiments of the present invention.
FIG. 6 illustrates a braided sleeve as one embodiment of a sleeve comprised in a gripper according to embodiments of the present invention, the sleeve being shown in a neutral and an extended configuration.

Alternatively, an elongate member 120 can be disposed in the gripper according to the following steps. Referring to FIG. 5a, first, the sleeve 101 is slid over the elongate member 120 to a desired position. Referring to FIG. 5b, the first end 104 of the sleeve 101 is placed in the first clamping element 102 and the second end 105 is placed in the second clamping element 103. This approach can simplify the assembly of the elongate member 120 within the gripper 100 in applications wherein threading the elongate member 120 through the clamping elements 102, 103 may be difficult.

In embodiments of the present invention, the elongate member 120 may comprise any of a number of tubular structures, catheters, guidewires, sheaths, needles or other elongated instruments, connectors, conduits for energy, water, drugs or other supplies, infusion, suction or signal lines, sensors, actuators, balloons, prosthetics.

Preferably, in embodiments wherein the gripper 100 is used for performing one or more gripping-and-translating maneuvers, wherein for each maneuver the elongate member is translated along a stroke distance $L_s$, the elongate member 120 has a generally cylindrical shape over a length $L_t$ which is larger than the stroke distance $L_s$. The stroke distance $L_s$ generally depends on the particular application; for example, in a cardiovascular application, wherein a catheter is to be inserted in the groin to operate on the heart, $L_s$ may be chosen as larger than the maximal traveled distance along all paths from groin to heart for that specific patient or from a cohort of targeted patients.

Embodiments of the present invention can advantageously drive an elongate member having a cross-section which is not necessarily circular, as well as tubular structures having a generally cylindrical shape, such as is the case for many vascular catheters. The circumference of the elongate member may be ellipsoidal, square, rectangular, and may in some embodiments be an open shape. For example, a tube having a slot running along at least part of the length of the tube, for example for providing access to the tube's inner area, would be an example of an elongate member for which the circumference is not closed.

According to embodiments of the present invention, an elongate member can be manipulated whose cross-sectional shape is not axi-symmetric or even not symmetric. Shape variations can be both geometric as well as mechanical. For example the compliance of the elongate member may be anisotropic such that upon application of an external load to the elongate member, the cross-section takes a shape which is not axi-symmetric.

A gripper according to embodiments of the present invention is capable of manipulating an elongate member having a cross-section which is not constant over $L_f$. The cross-section may vary at one or more different locations; for example, the elongate member may comprise more than one section, each having a different, constant cross-section. The elongate member may comprise a section over which the cross-section varies continuously. For example, the cross-section may vary monotonically from a relatively smaller cross-section towards a relatively larger cross-section or vice versa. The variation may in some embodiments follow non-monotonic profiles.

It is an advantage of embodiments of the present invention that an elongate member having variations in the diameter, width, cross-section, or shape of an elongate member can be manipulated safely and precisely.

One example of an elongate member which can be manipulated using a gripper according to embodiments of the present invention is a catheter comprising a plurality of different sections along the length of the catheter which may have different cross-sections, for example a catheter which supports a valve implant at its distal end, or which supports tracking sensors, balloons, stents or which has actuators or other components embedded along the length of the catheter. Embodiments of the present invention can allow unrestricted and safe manipulation of such multi-component, multi-section tubular structures.

Embodiments of the present invention can allow manipulation of an elongate member having a compliance which varies over the length of the elongate member. Such an elongate member may have for example a constant cross-sectional shape in the absence of external load, which may deform locally upon application of an external load. Such deformation may have a different form at different points along the elongate member. Embodiments of the proposed invention allow manipulation of the elongate member in the presence of such variation.

An elongate member capable of being manipulated by a gripper according to embodiments of the present invention may be for example a catheter containing an inflatable balloon in a particular section and having a relatively larger radial compliance at this section compared to a part of the catheter where no balloon is present. Embodiments of the present invention allow manipulation of the elongate member in the presence of such variations.

Embodiments of the present invention allow manipulation of a plurality of concentric elongate members having varying cross-sections.

For example embodiments of the present invention allow manipulation of a first elongate member having a relatively smaller cross-section and a second elongate member having a relatively larger cross-section, the second elongate member surrounding or partially surrounding the first elongate member. Manipulation can be provided at the transition from the first elongate member to the second elongate member and at intermediate points.

It is an advantage of embodiments of the present invention that the sleeve is capable of deformation and can conform to the profile of the elongate member, which can allow to establish a reliable, controlled and safe grip on the elongate member. The performance of the gripper can be less dependent on the actual shape of the elongate member.

Similar to the digestive tract a tubular deformable structure is proposed to drive the object to be transported, here an elongated tubular body, through its internal lumen. As the tubular structure contracts it constraints the inner object. When applying a twist or wrench upon the tubular deformable structure this twist or wrench can be transferred, possibly partially, upon the inner object. E.g. when the inner object is not constrained, and upon displacement of the outer tubular structure also the inner object will move. If no slip occurs, the displacement will in such case take place with a precision that is comparable to the precision with which the tubular structure is moved.

The spacing of the sleeve ends for gripping the elongate member may be determined, among other factors, by a load that the elongate member is required to overcome. For example in catheterization a catheter is pushed through an access port into the patient. The access port as well as the friction between the catheter and the patient can generate a resistance to catheter movement. This resistance should be overcome in order to be able to advance the catheter and represents a load for the elongate member to overcome. A drive system for driving the gripper should be capable of supplying the required force to overcome the load. It is noted that the force is transferred to the elongate member from the drive system by the sleeve and static friction between sleeve and the elongate member can also be in effect. As long as the static friction between the sleeve and the elongate member is greater than the load to be overcome and the force delivered by the drive system, the latter can be effectively transmitted from the sleeve to the elongate member. If the force is larger than the static friction between sleeve and catheter, the the sleeve can slip with respect to the elongate member. At such point only a force component equal to the dynamic friction force (which is typically will be much lower than the static friction force) can be transferred to the elongate member and the load cannot be overcome. For example the catheter may become stuck in the patient.

The longer the sleeve, the easier it is to generate a certain static friction (that is, using a smaller displacement of the ends of the sleeve). The material properties of the elongate member and the sleeve can also play a role in the required spacing as the static friction is typically proportional to a gripping force (perpendicular to the surface of the sleeve) with a scale factor equal to the static friction coefficient, this being is dependent on the combination of materials.

There can be a trade-off between providing sufficient static friction and keeping the sleeve as short as possible so as to have a more compact gripper. For a set sleeve length, different sleeve materials can be tested to increase the friction or gripping force without damaging the elongate member.

A sleeve 101 comprised in a gripper according to embodiments of the present invention preferably has a shape which can be adjusted to conform to and to constrain an elongate member. The sleeve 101 may be a braid, sheath, hose, bellow, bladder, cylindrical spring or other deformable tubular body suitable for engaging with the elongate member. The sleeve can serve as an intermediate component for translating the elongate member along the sleeve axis. The sleeve can serve as an intermediate component for rotating the elongate member about the sleeve axis.

In the following example, the operation of a sleeve in the form of a braided sleeve is described; however, it will be understood that the sleeve 101 comprised in a gripper 100 according to embodiments of the present invention may comprise a sheath, other type of sleeve, hose, bellow, bladder, cylindrical spring or other deformable tubular body.

Referring to FIG. 6, a braided sleeve 201 comprises a network of fibers 230 arranged in a tubular three-dimensional structure. Typically each individual fiber 231 of the braided sleeve 201 takes a helical form between a first end 204 of the sleeve 201 and a second end 205 of the sleeve 201.

In an equilibrium state the length of the braided sleeve 201 is $L_0$. In this state the internal stress in the fibers 230 of the braided sleeve 201 is relatively low. The stress is sustained by static friction that exists between contacting fibers 230. In this equilibrium state the braided sleeve 201 takes a generally cylindrical shape. For simplicity, ignoring the effects of gravity, the shape of the inner lumen can be considered to have an approximately circular cross-section with diameter $d_{b0}$. In this equilibrium state the shape of the cross-section can be considered to vary only marginally over the length of the braided sleeve 201.

By increasing and decreasing the distance between the first and second ends 204, 205 of the braid 201, the braid 201 contracts and expands radially. As the ends of each fiber are translated relative to each other and as the length of the individual fibers can be assumed to remain more or less constant during this action, the fibers will re-align and undergo a relative movement with respect to each other and the braid's central axis, thus causing a change in the shape of the cross-section of the braided sleeve 201.

Referring to FIG. 6 upper part, the braid is shown in the equilibrium state with length $L_0$. The fibers 230 follow a helical trajectory whereby the fiber direction takes on an angle $a_0$ with respect to the axis A-A of the braid 201. The braid 201 has an inner diameter of $d_{b0}$. If the distance between the first end 204 and the second end 205 is reduced to less than $L_0$, the braid will expand and have an inner diameter greater than $d_{b0}$. If the distance between the first end and the second end is subsequently increased to $L_0$, the braid returns to the original length $L_0$ and diameter $d_{b0}$.

In the equilibrium state the area of the inner surface of the braid is $$A_{b0} = \pi d_{b0}^2 / 4.$$

The inner circumference of the braid is given by $\pi d_{b0}$. The total length B of a single wound fiber 230 is constant and is given by equation 1:

$$B = \frac{\pi d_{b0} N}{\sin \alpha_0} \tag{1}$$

where N is the number of windings of the fiber. The braid length $L_0$ is then equal to $B\cos(a_0)$ and the length $dx_0$ of a single fiber winding is $L_0/N$.

Due to the construction of the braid and the property that the fiber length B remains essentially constant (it can be assumed to undergo only a negligible elongation along the fiber axis, for example less than 10%, less than 5% or less than 1%), when the distance between the first end 204 and the second end 205 is increased to a length L, the braid contracts radially. This can be seen in FIG. 6b.

Since the fiber length B can be treated as invariant, the variation of the fiber angle as a function of braid diameter $d_b$, given an initial braid angle $a_0$ and equilibrium state length $L_0$, can be described according to equation (2) or (3):

$$\frac{\pi d_{b0} N}{\sin \alpha} = \frac{\pi d_{b0} N}{\sin \alpha_0} \tag{2}$$

$$\frac{\sin \alpha}{\pi d_b N} = \frac{\sin \alpha_0}{\pi d_{b0} N} \tag{3}$$

Figure 7A:
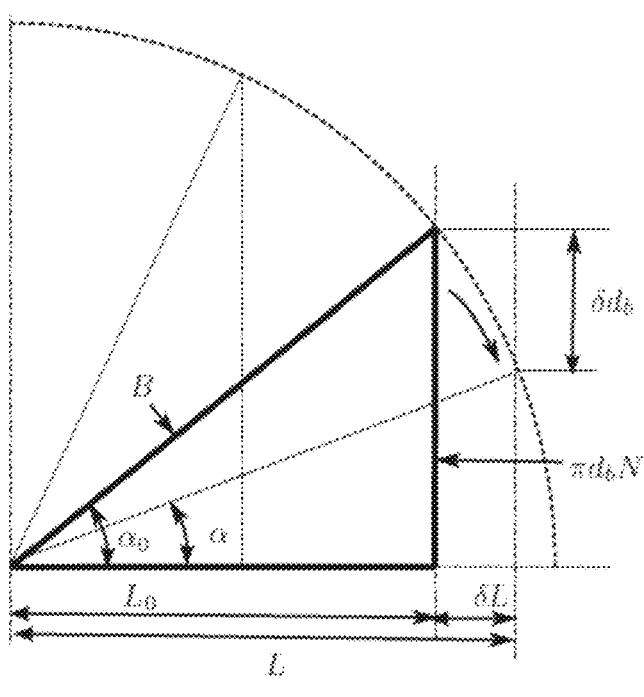
FIG. 7a illustrates the relation between braid contraction and dilation as a function of initial braid angle for a braided sleeve as one embodiment of a sleeve comprised in a gripper according to embodiments of the present invention, for a relatively small initial braid angle as compared to FIG. 7b.
Figure 7B:
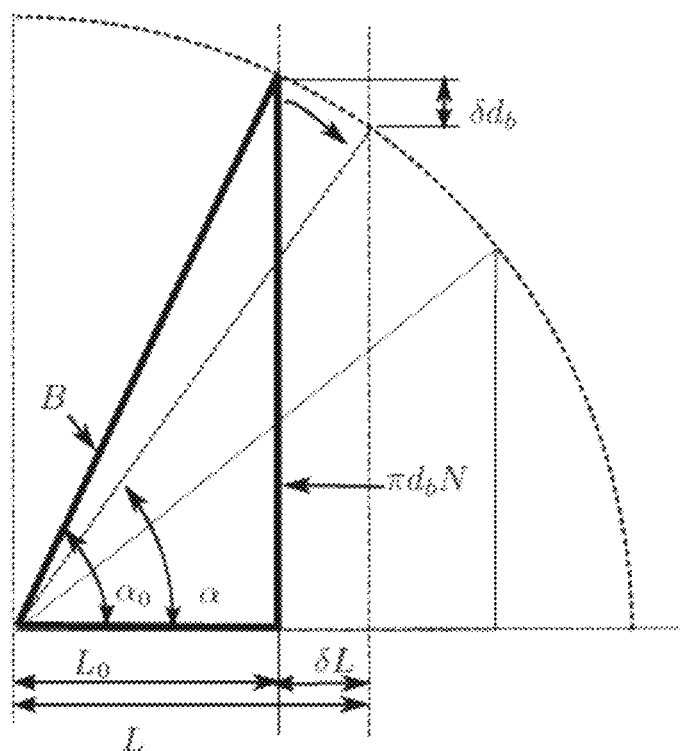

With reference to the schematic view as shown in FIG. 7 showing the relation between contraction and dilatation as a function of the initial braid angle upon extension and relaxation of a braid, where FIG. 7a shows the geometry for a relatively small value of initial braid angle and FIG. 7b shows the geometry for a relatively large value of initial braid angle, equations 2 and 3 can be reformulated to provide the braid length L as a function of the braid diameter $d_b$ according to equation 4:

$$L = \sqrt{(\pi d_{b0} N)^2 + L_0^2 - (\pi d_b N)^2} \tag{4}$$

and the braid diameter $d_b$ as function of the braid length L according to equation 5:

$$d_b = \frac{\sqrt{(\pi d_{b0} N)^2 + L_0^2 - L^2}}{\pi N} \tag{5}$$

It can be seen from FIG. 7 that depending on the initial braid angle $a_0$, for the same stroke length $\delta L$ the radial contraction varies such that the radial contraction is greater if a larger one if $a_0$ is smaller, and this also corresponds to a longer total sleeve length.

The choice of initial braid angle can depend on the application. For example if the sleeve is to be used with elongate members having a large variation in diameters, for example a guidewire having a diameter of 1 mm, a catheter having a diameter in the range 3-5 mm, an endoscope having a diameter in the range 3 to 15 mm, then a relatively large radial contraction is desired such that each of the instruments can be sufficiently gripped by the gripper. If the gripper is used only in a specific application such as radio-frequency-ablation of atrial fibrillation wherein the same 3 mm diameter catheter is repeatedly used, then for example a 4 mm outer diameter sleeve could be used with a contraction of for example 1.4 mm.

Figure 8:
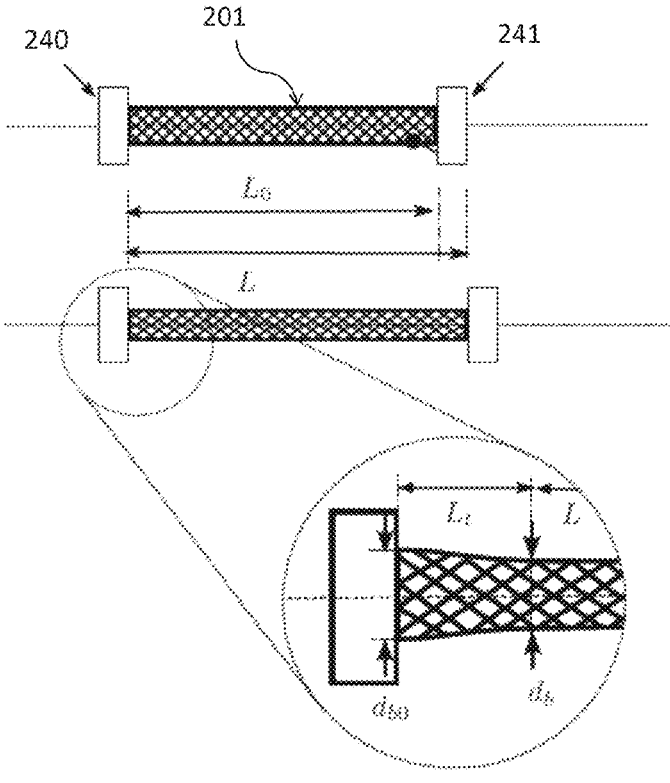
FIG. 8 is a cross-sectional view of a braided sleeve as one embodiment of a sleeve comprised in a gripper according to embodiments of the present invention, held between two collars and shows a detailed view of the sleeve adjacent to one of the collars.

Referring to FIG. 8, the braid 201 may be held at the first end by a first collar or clamp 240 and at the second end by a second collar or clamp 241. FIG. 8 shows a detailed view of the sleeve adjacent to the first collar 240, where a transition region can be seen. The transition region has a length $L_t$ over which the braid diameter varies from its equilibrium state diameter $d_{b0}$ at the first collar 240 and a contracted diameter $d_b$. In some embodiments the length of this transition region can be considered to be constant such that the total length $L_{tot}$ of the braid can be expressed according to equation 6:

$$L_{tot}=2L_t+L \tag{6}$$

where equations (1), (2), (3), (4), (5) hold for the length $L_0$ of the braid only, independent of the length of the transition regions. The total length in an extended state between the first end 204 and the second end 205 is then twice the length of the transition region plus the extended length L (which can be determined according to equation 4).

In some embodiments the transition region can vary in length. This can be incorporated by modeling the transition region to improve the overall accuracy of the contraction model. However, preferably and in general the transition region can be assumed to be constant.

The transition region itself provides a smooth transition from the ends of the braid towards the contracted region such that stresses upon the elongate member can build up gradually along the length of the braid.

Referring again to FIG. 7, it can be seen how the longitudinal extension or contraction $\delta L$ of a braid of initial length $L_0$ to a length L leads to a corresponding contraction or relaxation of the diameter $d_b$ by an amount $\delta_{db}$ equal to $d_{b0}$-$d_b$. It can also be seen how, for a same fiber length B and a same longitudinal contraction or extension L, the initial braid angle $a_0$ plays an important role, offering a large contraction in FIG. 7a compared to FIG. 7b.

The braid angle can be chosen so as to provide a suitable variation of $d_b$ for a corresponding variation of $\delta L$ depending on the envisioned application. This choice may be made depending on the size of the elongate member to be manipulated, the speed, precision and effort of radial contraction and expansion and the speed, precision and effort of longitudinal extension or relaxation.

As the number of turns N does not vary if only the distance between the first end 204 and the second end 205 is varied, and $d_{b0}$ and $L_0$ are fixed for a particular application, equation (5) provides a simple means of regulating the length L relative to $L_0$ and therefore to control the diameter $d_b$. Equation 5 clearly shows how the braid diameter $d_b$ can be caused to decrease to less than its equilibrium state diameter $d_{b0}$.

It is noted that for values of a approaching 0 or 90 degrees the braid may stop functioning as a braid and the equations 1 to 5 may no longer hold. For example, the equations 1 to 5 may not be applicable for values of a less than 5 degrees or greater than 85 degrees.

When the braid diameter $d_b$ is equal to the diameter of an elongate member located in the braid, contact will occur between the surface of the elongate member and the inner surface of the braid, which can prevent a further decrease of braid diameter according to equation (5). At this point the braid may still contract but the contraction may be much less than that predicted by equation 5. The contraction may then be determined by the properties, for example the compliancy, of the elongate member contained in the braid.

As the braid further extends, the contraction will continue and cause a distributed gripping force upon the elongate member 240. The intensity of the gripping force can be regulated by adjusting the degree of longitudinal contraction appropriately, by controlling the spacing of the first and second ends 204, 205 of the braid 201.

This ability to provide a distributed and controllable gripping force means that the gripper according to embodiments of the present invention is ideally suited for gripping and manipulation of fragile tubular structures such as cables, ropes, optical fibers or other fragile elongated bodies such as endoscopes, catheters, guidance sheaths, guidewires or combinations thereof.

Figure 9:
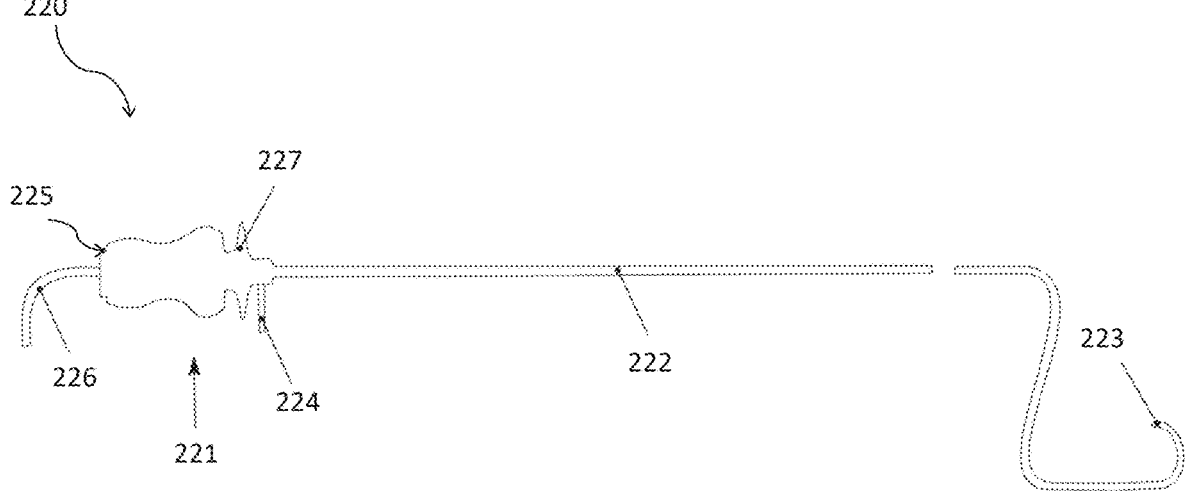
FIG. 9 illustrates a catheter as an example of an elongate member which can be manipulated by a gripper according to embodiments of the present invention.

Referring to FIG. 9, a catheter 220 as an example of an elongate member which can be manipulated by a gripper according to embodiments of the present invention is shown. The catheter 220 comprises a handle portion 221, a tube portion 222, and a tip portion 223. The tube portion 222 connects the handle portion 221 and the tip portion 223. The handle portion 221 is typically located at the proximal end of the catheter 220, whereby proximal refers to the end closest to the operating clinician or drive system and whereby distal refers to the end furthest from to the operating clinician or drive system. The tip portion 223 is located at the distal end of the tube portion 222. The handle portion 221 may include an irrigation port 224 for introducing water or other fluids, for example for irrigation of an operating site close to the catheter tip 223, to lubricate the catheter, or to ease insertion or retraction of the catheter 220 in a patient. The handle portion 221 may also include a back port 225 through which one or more wires or cables 226 may enter the handle portion 221. Cables 226 may supply power to the catheter 220 and/or may provide a connection for, for example, transmitting (and/or receiving) signals or energy, or relaying data from one or more transducers (not shown) which may be provided on the catheter 220.

The handle portion 221 may include actuators to control the behaviour of the catheter 220. For example the handle portion 221 may include a front flange (not shown) and a back flange (not shown) that may be squeezed together or pulled apart such that an inner cylinder and an outer cylinder (not shown) slide back and forth with respect to each other. This relative motion could be transferred through a pull-wire, a pair of concentric tubes or other means towards the distal tip of the catheter and could induce a motion of the said distal tip 223 such that the pose of the distal tip 223 can be controlled by the configuration of the handle 221.

Figure 10:
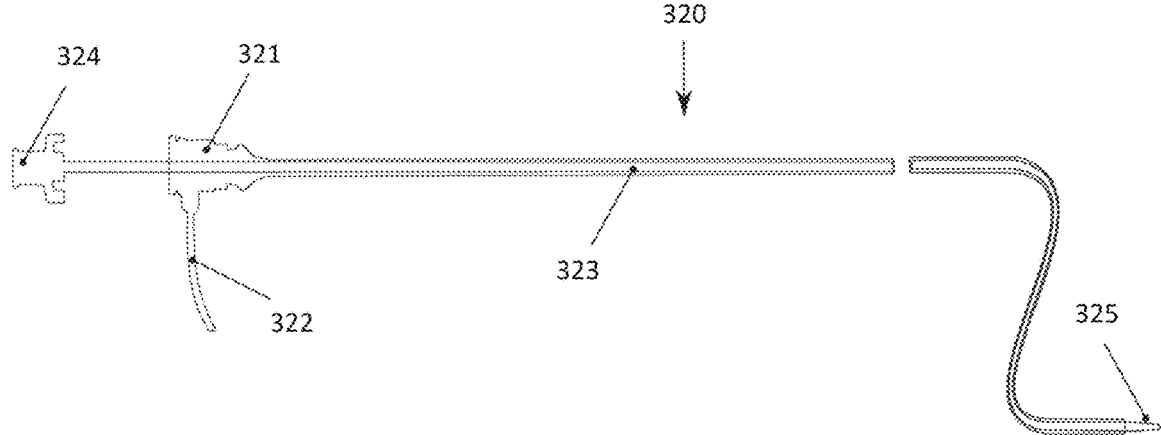
FIG. 10 illustrates a guidance sheath as an example of an elongate member capable of being manipulated by a gripper according to embodiments of the present invention.

Referring to FIG. 10, a guidance sheath 320 as an example of an elongate member capable of being manipulated by a gripper according to embodiments of the present invention is shown. The guidance sheath 320 has a proximal portion 321 with irrigation port 322 and a tube portion 323 that extends distally. The guidance sheath comprises a handle portion 324 such that the proximal portion 321 is between the tube portion 323 and the handle portion 324. The tube portion 323 can be inserted into a patient for example through a blood vessel to provide guidance to tools that may be inserted into the patient through the guidance sheath 320. The guidance sheath 320 comprises a dilator tip portion 325 at the distal end of the tube portion 323.

After being placed in the patient, the guidance sheath 320 may provide guidance up to a target anatomic site for tools that may be exchanged through the tube of the guidance sheath 320. The guidance sheath 320 can also shield the vessel from the passage of said tools.

Embodiments of the present invention allow to steer the guidance sheath 320 when introduced through the sleeve or to steer the dilator tip 325 when the sleeve is engaging with the dilator at the surface located between the handle 324 and the proximal portion 321. Embodiments of the present invention comprising a plurality of sleeves allow to steer the guidance sheath 320 and the sheath 320 and dilator tip portion 325 separately or jointly.

Figure 11:
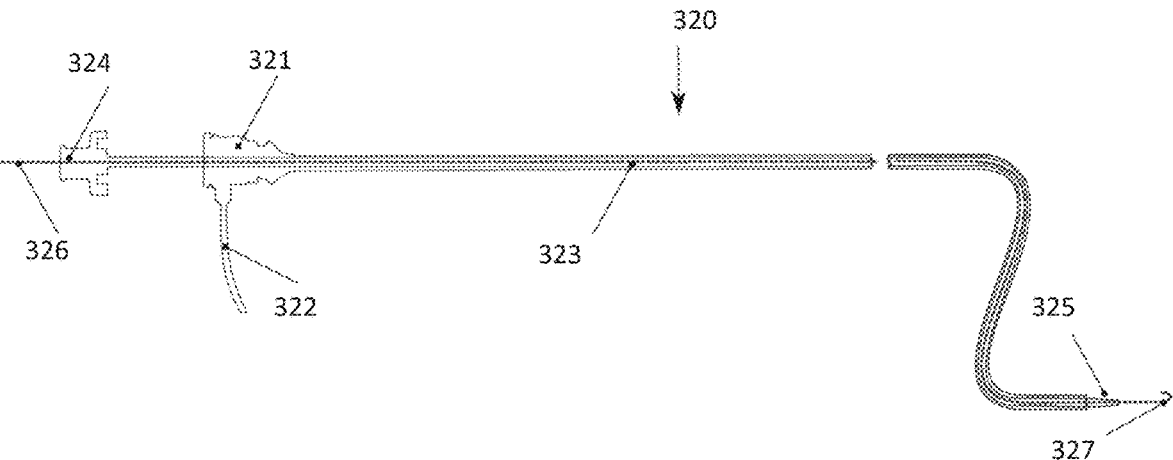
FIG. 11 illustrates a guidewire as an example of an elongate member capable of being manipulated by a gripper according to embodiments of the present invention.

The present invention is modular. A plurality of grippers can be employed to drive a plurality of elongate members, or to drive different parts of an elongate member. Referring to FIG. 11, additionally to a guidance sheath 320 and a dilator 325, a guidewire 326 may be introduced into a patient. Embodiments of the present invention allow to steer the guidewire 326 and the tip of the guidewire 327 by engaging the sleeve at the guidewire at the side proximal to the handle of the dilator 324.

Figure 12:
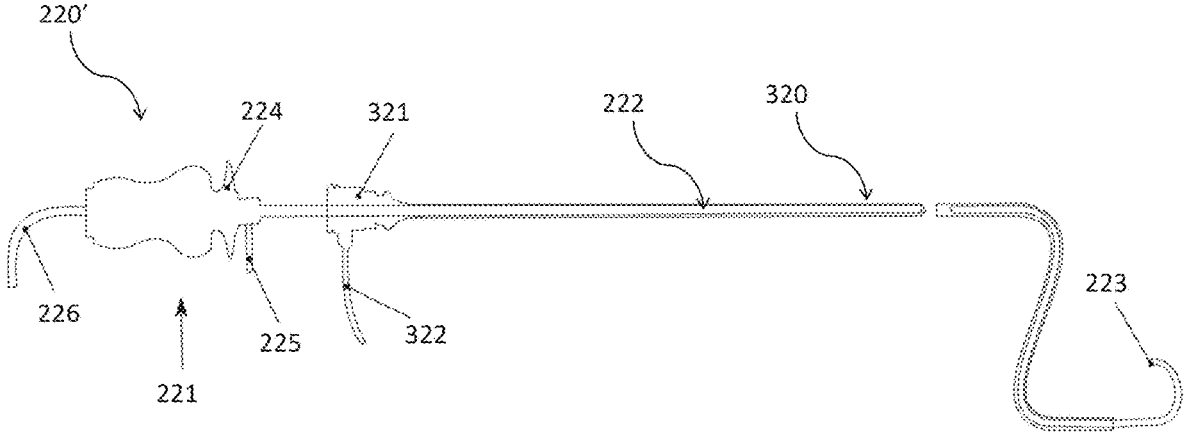
FIG. 12 illustrates a modified catheter as an example of an elongate member which can be manipulated by a gripper according to embodiments of the present invention.

Referring to FIG. 12, a modified catheter 220' is shown which is an elongate member capable of being manipulated by a gripper according to embodiments of the present invention. The modified catheter 220' comprises a handle portion 221, a tube portion 222, and a tip portion 223. The tube portion 222 connects the handle portion 221 and the tip portion 223. The handle portion 221 comprises a flange 224 for steering the tip portion 223. The modified catheter 220' comprises an irrigation port 225 at the handle 221. The modified catheter 220' may comprise a cable 226 for connecting the tip portion 223 of the catheter 220' to the proximal handle portion 221. Upon displacement of the flange 224, the cable would be pulled or released such that the tip portion 223 deforms or deflects.

Such a catheter with a distal steering section could be steered directly by means of a preferred embodiment of the invention capable of gripping the catheter at a location that is more proximal to a guidance sheath 320 if included along the catheter body or at the handle portion 221. Alternatively it could be steered jointly with the guidance sheath 320.

Embodiments of the invention allow to steer an elongate member over a full targeted insertion stroke, that is, manual steering of the elongate member may be carried out in addition to translation or steering of the elongate member by the gripper. In some embodiments the gripper may steer an elongate member over a shorter range, for example steering the elongate member only over a portion of the targeted stroke. For example, in the case of steering catheters, guidewires or sheaths a clinician may wish to introduce the catheters, guidewires or sheaths manually up to a certain point, for example up to the heart, after which the catheter, guidewire or sheath may be coupled to a gripper according to embodiments of the presented invention for steering over a limited range or area with increased control and precision.

Figure 13:
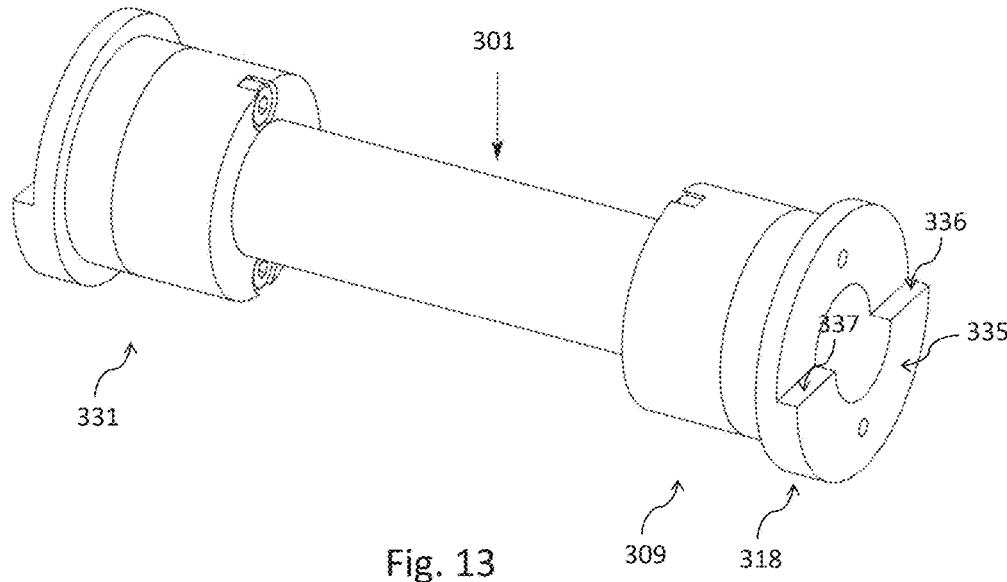
FIG. 13 is a perspective view of a sleeve which may be comprised in a gripper according to embodiments of the present invention which is couplable to collars at each end.
Figure 14A:
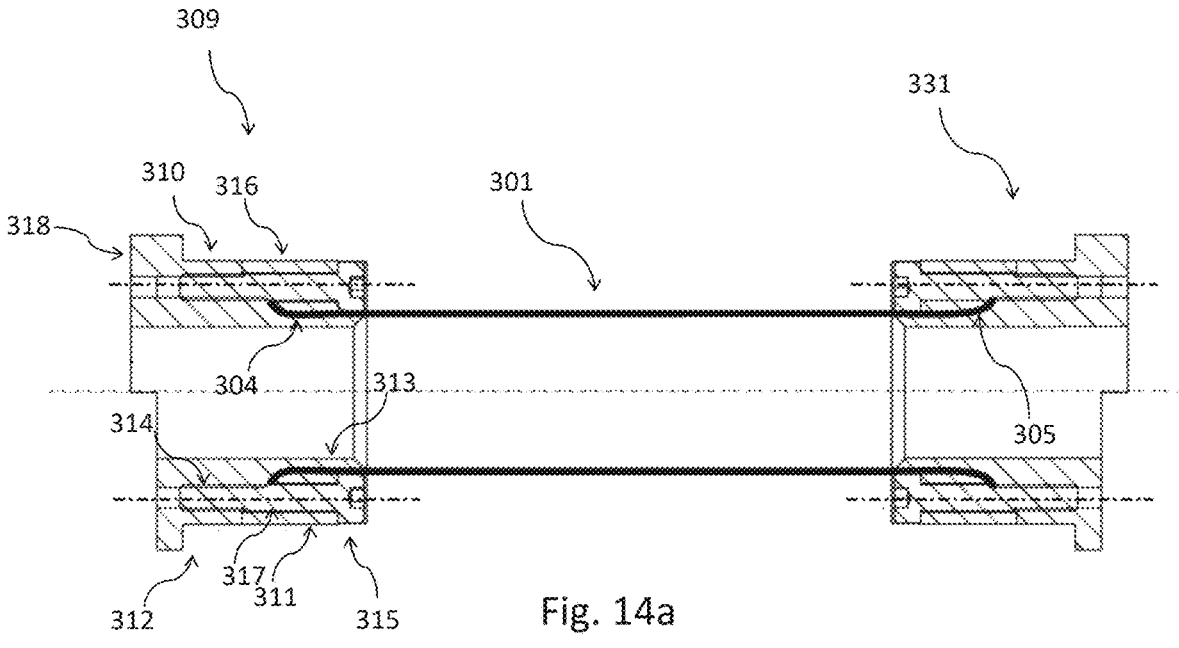
FIG. 14a is a cross-sectional view of the sleeve of FIG. 13.
Figure 14B:
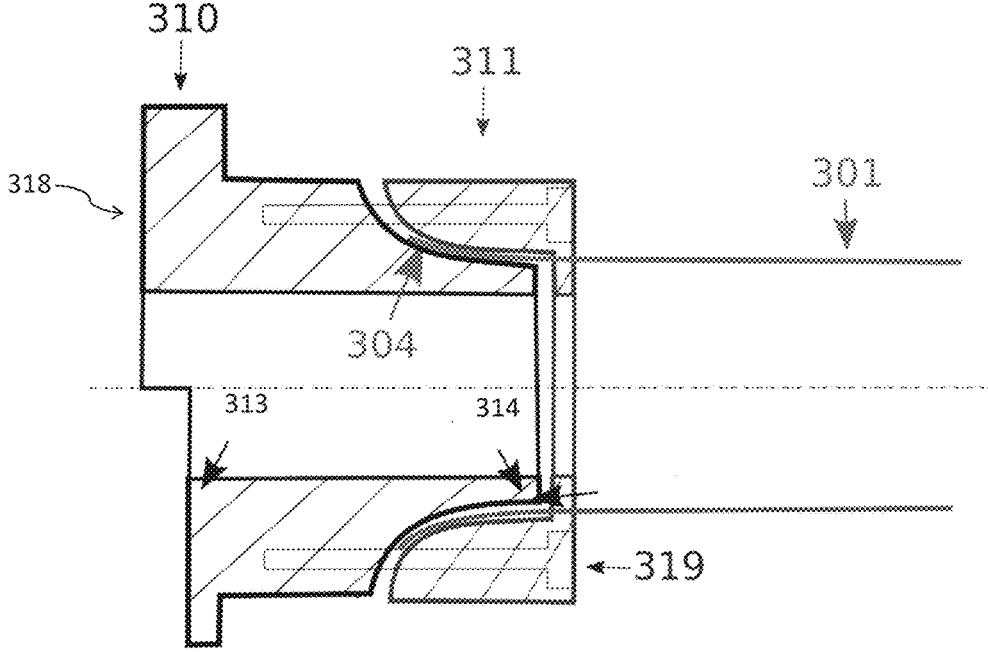
FIG. 14b is a detailed cross-sectional view of one end of the sleeve of FIG. 13.

Referring to FIGS. 13, 14a, and 14b, a sleeve 301 which may be comprised in a gripper according to embodiments of the present invention is shown. The sleeve 301 has a generally tubular shape and extends between a first end 304 and a second, opposite end 305.

The first end 304 of the sleeve 301 is couplable to a first collar 309. The first collar 309 comprises a receiving portion 310 and a fixing portion 311. The receiving portion 310 is generally tubular in shape with a constant inner diameter and extends between a first end 312 and a second end 313. The receiving portion 310 has a first outer diameter at the first end 312 which is constant over a first length and then decreases over a second length to a second outer diameter, which is less than the first outer diameter, at the second end 313. The receiving portion has at least one hole 314 for receiving a fixing element, the hole 314 extending parallel to the axis of the receiving portion. The receiving portion comprises an end portion 318 at the first end 312 having an outer diameter greater than the first outer diameter so as to form a shoulder at the first end 312.

The fixing portion 311 is generally tubular in shape with a constant outer diameter and extends between a first end 315 and a second end 316. The fixing portion 311 has a first inner diameter at the first end 315 which is constant over a length $l_3$ and then increases over a length $l_4$ to a second inner diameter at the second end 316 which is greater than the first inner diameter. The fixing portion has at least one hole 317 for receiving a fixing element, the hole 317 extending parallel to the axis of the fixing portion 311.

The first end 304 of the sleeve 301 can be assembled in the first collar 309 as follows. The first end 304 of the sleeve 301 is fitted over the second end 313 of the receiving portion 310. The fixing portion 311 is slid over the first end 304 of the sleeve such that the first end 304 of the sleeve is held between the second end 313 of the receiving portion 310 and the fixing portion 311. The fixing portion 311 and the receiving portion 310 are positioned such that the holes 314 and 317 are aligned. A screw or bolt 319 is inserted through the holes 314 and 316 and secured.

It will be understood that a second collar 331 may be provided having essentially the same form and construction as the first collar 309. The second end 305 can be assembled into the second collar 331 in a similar manner to the assembly of the first end in the first collar 309.

The end portion 318 of the first collar 309 also comprises a shoulder portion 335 extending from the end portion and having a semi-tubular shape, such that contact faces 336 and 337 are provided perpendicular to the sleeve axis. The end portion 318 can help to allow clamping of the sleeve 301 in a clamping element as will be described in further detail hereinafter. The end portion 318 can also help to allow efficient transfer of twists and wrenches between the clamping element and the sleeve.

The configuration shown in FIGS. 13 and 14 has an advantage that the collars can be re-used and allow easy exchange or replacement of the sleeve 301. This can help ensure integrity and repeatable behavior of the sleeve.

It will be understood that alternative methods for connecting the sleeve to the clamping elements can be implemented that realize similar efficient transfer of twists and wrenches.

Different type of connectors or collars may be used that can be re-used or replaced each time. In an alternative preferred embodiment the connectors or collars may form an integral non-separable part of the sleeve such that they can be disposed of together with the sleeve after each use. Alternatively the connectors may be re-used, cleaned and possibly sterilized together with the sleeve after each use. The combination of connectors and sleeves may for example be 3d-printed together for single or multiple use.

It may be understood that one function of the collars is to rigidly clamp the sleeve at its ends such that the deformation of the sleeve takes place preferentially in between the collars 309, 331 and not within the collars where the sleeve is sandwiched between the receiver portion 310 and the fixing portion 311 for the first collar 309, and the corresponding portions of the second collar 331. Preferably, neither deformation nor slip of the sleeve takes place within the collars 309, 331.

The collars 309, 331 are generally tubular in shape and have a cylindrical lumen through which an elongate member can pass. Referring again to FIG. 14, it can be seen that the second end 314 of the inner tubular portion 312 has a rounded end such that an elongate member that is passed through the sleeve does not encounter sharp edges that may damage the elongate member. In some preferred embodiments all edges of the collars are rounded so as to remove sharp edges.

In some embodiments the receiving portion 310 has a conical outer surface and the fixing portion 311 has an inner lumen which is conical in shape. This configuration of conical shapes can allows a stable and reliable fixation of the sleeve free from slip by simply tightening the bolts 319. Removal of the sleeve is also simplified.

The bolts 319 may be conveniently passed through natural or widened holes of the braid 301 or through hand-made holes in that braid or through holes in any generic sleeve that is held by the collars 309 and 331.

Although a braided sleeve has been described, the sleeve 301 may also comprise a spring, a hose or any other stretchable fabric or structure. The sleeve 301 may comprise a single open-ended cylindrical surface or it may comprise a plurality of stretchable portions that together form a generally closed cylindrical surface.

In some embodiments, a cross-section of the sleeve does not form an entirely closed contour. In some embodiments, a surface of the sleeve does not form an entirely closed cylindrical surface. The sleeve may also contain one or more holes or one or more slots that may be aligned parallel to the sleeve axis. The slots or holes may be arranged around the circumference of the sleeve and/or along the sleeve axis, for example in a spiral configuration.

A sleeve comprising a non-closed surface may be used advantageously to provide access to the inside region of the sleeve, for example to introduce an elongate member to the sleeve from the side, to introduce lubrication, or to provide a visual connection to the inside region of the sleeve through which a sensor could for example detect the presence, the state, position or any other relevant feature of the inner surface of the sleeve.

Where a displacement of the first end of the sleeve relative to the second end of the sleeve is mentioned, it will be understood that such a displacement is not limited to a displacement along an axis that is parallel to the sleeve axis, and displacement may also comprise of any variation in pose such as a three-dimensional translation, a twist, a change in relative orientation or any arbitrary combination of translation and relative orientation.

A sleeve comprised in a gripper according to embodiments of the present invention may be provided with additional materials or components having different functions.

For example, a sleeve comprising a braid which can provide strength and contractile behaviour may be provided surrounded by a material such as silicone which can provide watertight closure or a sterile barrier between the interior of the sleeve and the exterior of the sleeve.

Figure 15:
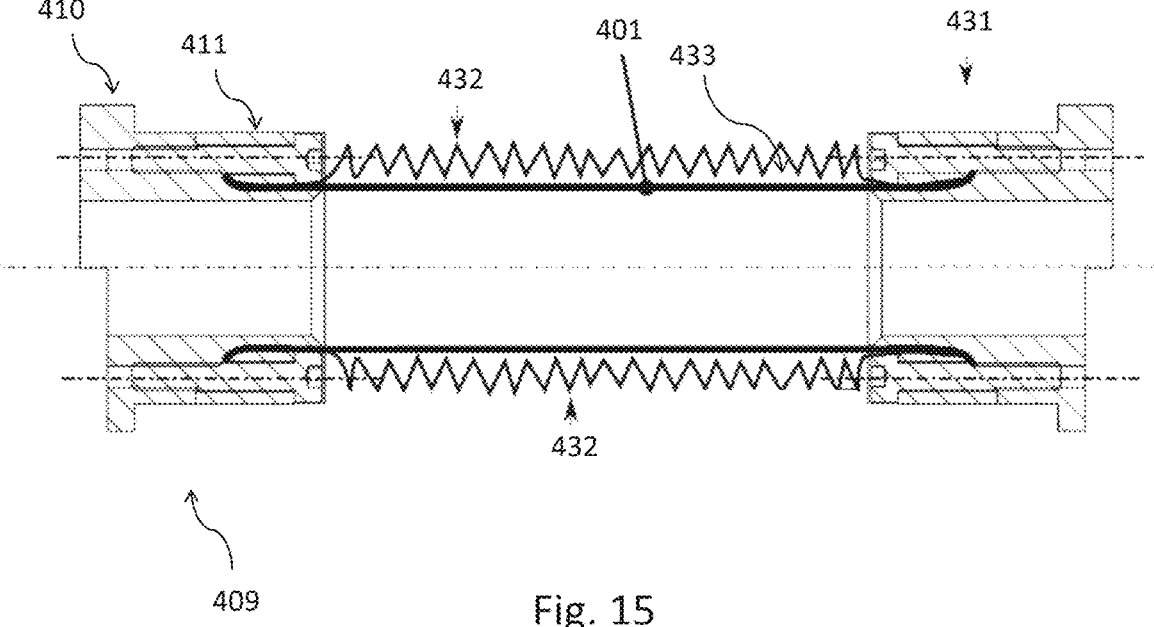
FIG. 15 is a cross-sectional view of a sleeve which may be comprised in a gripper according to embodiments of the present invention and a bellow.

For example, referring to FIG. 15, a sleeve 401 is shown. The sleeve 401 is fixed within collars 409, 431 in a similar manner to the sleeve 301 of FIG. 14. The collars 409, 431 have a similar construction to the collars 309, 331 of FIG. 14. The sleeve 401 is provided with a bellow 432.

The bellow 432 has a generally tubular shape. The bellow 432 is arranged coaxially with and surrounding the sleeve 401. The ends of the bellow 432 are fixed in the collars 409, 431 in the same manner as the sleeve 401. For example, one end of the bellow 432 is fixed in the first collar 409 between the fixing portion 411 and the receiving portion 410 in the same way as the first end of the sleeve 401 is fixed.

The bellow 432 is preferably arranged so as to provide negligible interference with the normal contractile and relaxational behaviour of the sleeve 401. The bellow 432 may have for example a concertina shape. The bellow 432 may for example provide a chamber 433 between the bellow 432 and the sleeve 401. The chamber 433 may contain for example a gas, liquid or micro-organism. For medical applications the bellow 432 may for example help to provide a sterile barrier between the inner region of the sleeve 401 and the space external to the bellow 432.

A sleeve comprised in a gripper according to embodiments of the present invention may comprise a synthetic material, for example nylon, polyethylene, aramids or acrylics of natural fabrics such as from linen, hemp, cotton. A sleeve comprised in a gripper according to embodiments of the present invention may comprise a metallic material, for example in a metallic braid configuration with or without additional coating material(s). For example a sleeve comprised in a gripper according to embodiments of the present invention may comprise a metallic braid impregnated with silicone which can help to provide soft contact with a fragile elongate member to be manipulated.

In some embodiments the sleeve may comprise a plurality of materials or composite materials such as optical fibers with a surrounding cladding.

In some embodiments the sleeve may comprise fibers having a sensing functionality. For example, one or more of the fibers may comprise a smart material having a property which changes in dependence upon the length or configuration of the fiber. For example, a piezoresistive material has a resistance which changes depending on the strain the material experiences. Such a behaviour could be used for example to measure a contractile state of the sleeve, which may then be used for control or safety purpose. Other examples according to the present invention include materials capable of reacting to or detecting contact pressure, temperature or any other relevant variable which may then be used to improve performance or reliability of the gripper.

In some embodiments the sleeve may comprise a smart material capable of deformation upon application of pressure, voltage, current or another trigger. Such a sleeve may be configured to realize both a gripping and actuation feature in a compact space. For example the sleeve may comprise fibers of a shape memory alloy (SMA) capable of changing length when exposed to a change in temperature. By sending a current through the fibers comprising such a sleeve, the temperature of the fibers can be increased and the length of the fibers can be changed.

A sleeve comprising such smart materials may allow to provide a gripping force whilst minimizing or keeping unchanged the distance between the sleeve ends. This can be advantageous in applications wherein large displacements of the sleeve ends are not desirable.

Figure 16:
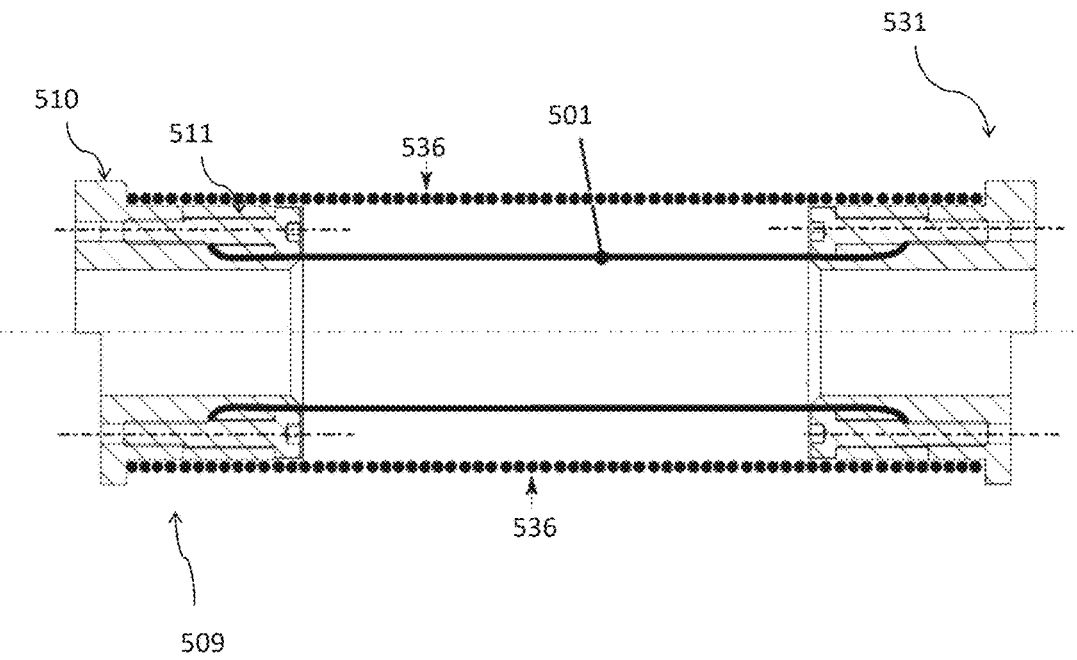
FIG. 16 is a cross-sectional view of a sleeve which may be comprised in a gripper according to embodiments of the present invention and a spring arranged coaxially with the sleeve.

Referring to FIG. 16, a sleeve 501 may be provided with a spring 536. The spring 536 is arranged coaxially with and surrounding the sleeve 501 and is fixed between the first collar 509 and the second collar 531, the first and second collars having the same configuration as the first collar 309 and the second collar 331 respectively. The spring extends between a first end fixed at an outer surface of the first collar 509 and a second end fixed at an outer surface of the second collar 531. However, other means or positions for mounting a spring-like structure between the first collar 509 and the second collar 531 are possible.

The spring 536 may provide an aligning function which can simplify coaxial alignment of the first collar 509 and the second collar 531. The spring 536 may be configured to maintain the sleeve in a particular state in the absence of actuation. For example, the spring 536 may be configured to maintain the sleeve in a minimal energy state when the sleeve is not under tension from displacement of the collars 509, 531.

The spring 536 may be configured such that a state of minimal energy of the sleeve 501 corresponds to a state wherein the sleeve 501 is fully contracted with respect to its state when not provided as fixed or tensioned in the collars 509, 531.

The spring 536 may be configured such that a state of minimal energy of the sleeve 501 corresponds to a state wherein the sleeve 501 is fully extended with respect to its state when not provided as fixed or tensioned in the collars 509, 531.

The spring 536 may be configured such that a state of minimal energy of the sleeve 501 corresponds to a state wherein the sleeve 501 is in a different preferred state between a fully contracted or fully extended state with respect to its state when not provided as fixed or tensioned in the collars 509, 531.

In some embodiments the spring 536 can therefore allow to fix the sleeve in a state of radial extension which can help to simplifying the introduction and removal of an elongate member into the sleeve, for example upon loss of power.

In some embodiments the spring 536 can allow to fix the sleeve in a state of radial contraction such that additional means are required to open the sleeve for receiving or removing an elongate member. Such a configuration can allow to lock the elongate member within the sleeve such that upon removal or loss of power to the gripper the elongate member can be fixed in the sleeve 501.

The amount of pre-tension and the choice of the preferential neutral position of the spring 536 may be tailored to adjust the intensity of the gripping force, to affect the speed at which contraction or extension takes place in the presence or absence of an external source of actuation. The chosen configuration of the spring can allow to create a 'fail-safe' sleeve capable of holding the elongate member in a safe condition upon removal or loss of power. The safe condition may be that the elongate member is free to move within the sleeve, is prevented from motion, or any other preferred state between.

The stiffness of the spring 536 is one factor which determines the resistance to efforts to bring the sleeve 501 into a state different from the minimal energy state in which the spring 536 normally maintains the sleeve 501. The pretension and chosen neutral position of the spring 536 may be chosen to complement an effort provided by an external actuation mechanism such that the external effort required to reach a particular extended, contracted or intermediate state of the sleeve can be dynamically reduced.

For example, where an external actuator such as an shape-memory-allow is known to have a relatively fast response time when changing to an excited state, for example a relatively fast contraction time upon heating, the return of the actuator to a non-excited state may require cooling which—if not done actively—is typically slower than the time to reach the excited state. The spring 536 may thus allow to support the external actuation during the non-excited phase. The spring 536 may also be configured to further increase the intensity of the response or damp the response during either the excited or non-excited phase.

Figure 17:
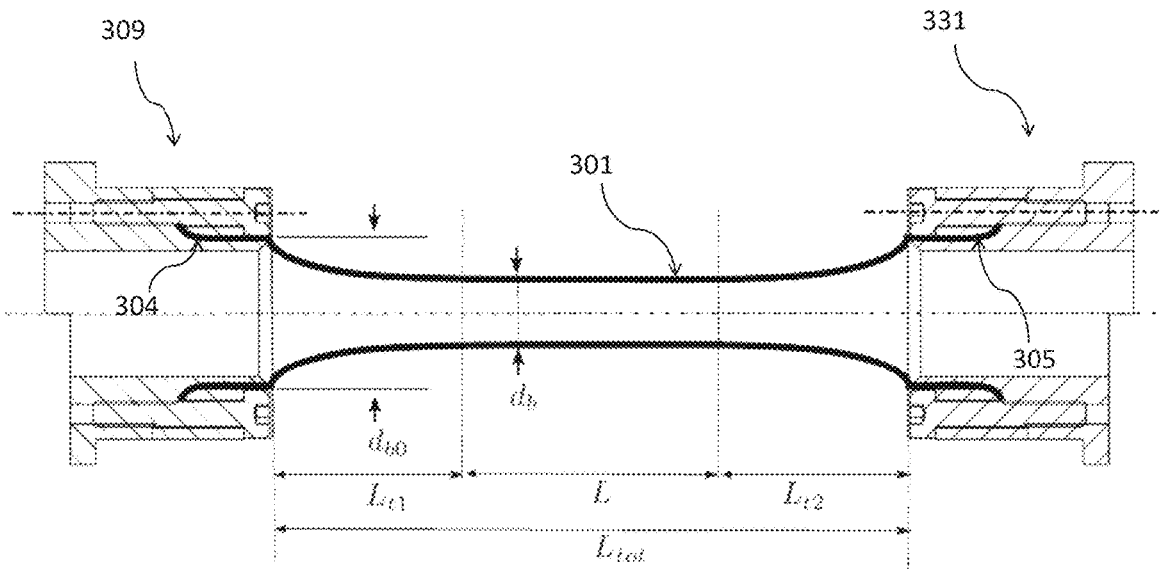
FIG. 17 is a cross-sectional view of the sleeve of FIG. 13 in an extended state.

Referring to FIG. 17, a cross-sectional view of FIG. 14 is shown wherein the sleeve 301 is in an extended state. The distance $L_{tot}$ between the first collar 309 and the second collar 331 is greater than the distance between the first collar 309 and the second collar 331 in an equilibrium state of the sleeve 301, for example when no tension is applied to the sleeve 301.

It is seen that the distance $L_{tot}$ includes a portion L over which the sleeve 301 has an approximately constant cross section which, in the case that the cross section is circular, can be characterized by a diameter $d_b$. The distance $L_{tot}$ also includes a first transition region of length $L_{t1}$ adjacent to the first end 304 of the sleeve 301 and a second transition region of length $L_{t2}$ adjacent to the second end 305 of the sleeve

301. The region of approximately constant cross section is between the first and the second transition regions. In the first and the second transition regions, the cross-section of the sleeve 301 gradually changes from an initial cross section adjacent to the first and the second ends respectively, having a diameter $d_{b0}$, to a cross-section with diameter $d_b$.

Preferably the total length of the first and second transition regions $L_{t1}+L_{t2}$ remains approximately equal to $L_t$ as the length L over which the cross section is approximately constant varies.

The variation of cross-sectional shape can be influenced by the presence or absence of an elongate member or other structure present within the sleeve 301. In general, but not necessarily, towards the centre of the structure 222 a deviation from an initial diameter $d_{b0}$ may be more pronounced leading to a more intense grip or stress distribution towards the center of 222.

In general, but not necessarily, as the amount of extension $L_{tot}$, increases so will the amplitude of deviation from $d_{b0}$ and so will the length of the length of the region L. Depending on the properties of the structure 222, of the properties of an elongate member which may be held by the sleeve, and of the sort of actuation applied to the sleeve, the length of region L may change faster or slower than the corresponding change in $L_{tot}$.

Likewise also the transition regions and lengths $L_{t1}$ and $L_{t2}$ may change. It can be understood that when the transition regions grow too short, the stress in the sleeve may grow too large up to a level that may cause permanent damage to the sleeve. Also at other points in the structure 222 stresses may grow large as $L_{tot}$ increases.

In some embodiments the spring 536 (FIG. 16) can help to prevent excessive extension of the sleeve 501 and increase of $L_{tot}$. Other mechanical means such as mechanical stops may be provided with the sleeve to help prevent excessive extension or contraction of the sleeve 301. In some embodiments, one or more sensors may be provided with the sleeve configured to monitor extension and compression of the sleeve. A gripper according to embodiments of the present invention may comprise a control element configured to receive measurements from such sensors and to control the position or orientation of the clamping elements so as to compensate for excessive extension or compression.

Sharp edges of components such as the collars 309, 331 may be rounded off to help reduce local stress concentrations on the sleeve 301. In some embodiments it may be advantageous to build in locations which are structurally weaker such that upon excessive stresses failure would preferentially take place at such location.

Embodiments of the present invention are capable of manipulating elongate members having a cross-section which is not required to be circular in shape. Embodiments of the present invention are capable of manipulating elongate members having a cross-section which varies in shape and/or size along the length of the elongate member.

Figure 18:
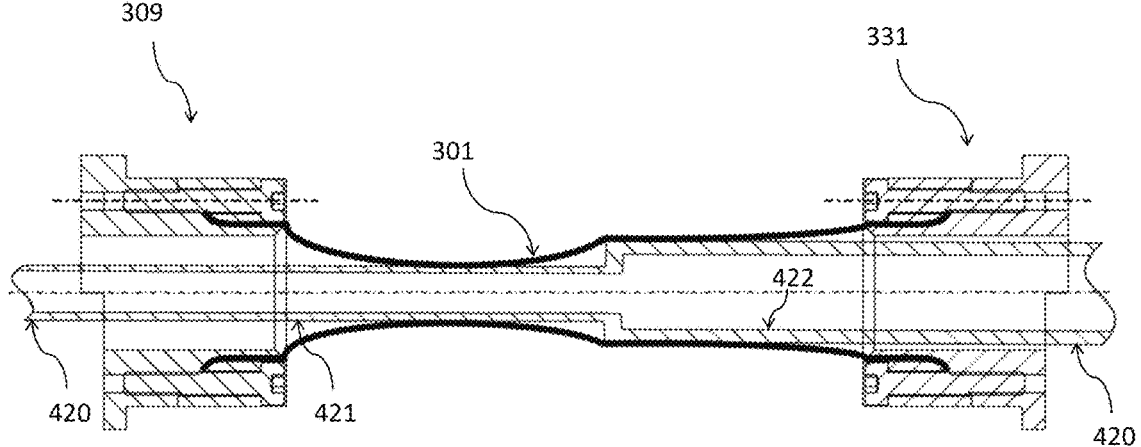
FIG. 18 is a cross-sectional view of a sleeve which may be comprised in a gripper according to embodiments of the present invention and an elongate member held by the sleeve, the elongate member having first and second portions with different diameters.

Referring to FIG. 18, a gripper comprising a sleeve 301 according to embodiments of the present invention is capable of manipulating an elongate member 420 comprising a first portion 421 having a first cross-section and a second portion 422 having a second, different cross-section. The transition between the first portion 421 and the second portion 422 may be continuous or discrete.

It will be appreciated that a gripper according to embodiments of the present invention is capable of manipulating an elongate member having more than two sections of different cross-section, for example different shapes and/or widths of the cross section.

Such an elongate member may comprise a combination of multiple structures that are concentric. One or more of the concentric structures may be at least partially contained within another of the concentric structures. For example, an elongate member capable of being manipulated by a gripper according to embodiments of the present invention may comprise an assembly of a catheter and a catheter sheath, an assembly of a guidewire and a catheter, or other similar combinations of multiple tubular structures.

Figure 19:
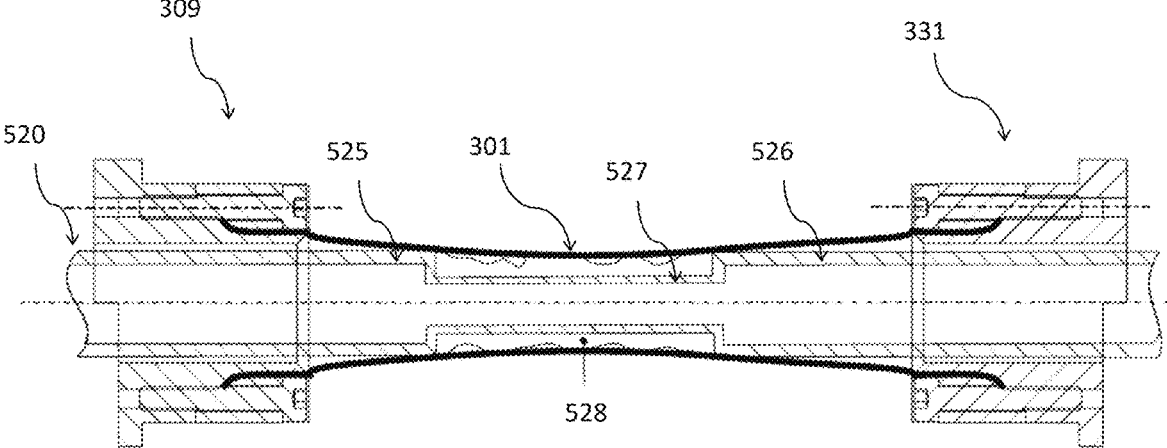
FIG. 19 is a cross-sectional view of a sleeve which may be comprised in a gripper according to embodiments of the present invention and an elongate member held by the sleeve, the elongate member having first and second portions with different diameters and compliances.

Embodiments of the present invention allow to manipulate an elongate member having mechanical properties which vary along the length of the elongate member. Referring to FIG. 19, an elongate member 520 is gripped by a sleeve 301 which may be comprised in a gripper according to embodiments of the present invention. The elongate member 520 comprises first and second end portions 525, 526 respectively and a central portion 527 between the first and second end portions 525, 526. The central portion 527 has a diameter which is less than the diameters of the first and second end portions 525, 526. The elongate member 520 comprises a balloon 528 comprising a material having a compliance which is greater than that of the central portion 527 and the first and second end portions 525, 526. Whereas under normal conditions the cross-section may be constant for this elongate member along its length, upon applying external pressure such as e.g. when gripping the structure with a gripper, due to its larger compliancy the cross-section at the central portion 527 may deform differently from the first and second end portions 525, 526 resulting in a tubular structure with variable cross-sections.

It is an advantage of embodiments of the present inventions that an elongate member having varying mechanical properties and/or cross section along its length can be gripped and manipulated. As the sleeve is capable of conforming to the surface of the elongate member, the gripping force can be distributed over the contact length of the sleeve and the elongate member, which can help to reducing local stresses.

For example, in some applications wherein it may be considered too risky to introduce sophisticated catheters with embarked balloons or stents in certain robotic drivers such as those making use of rollers, belts or compact grippers on linear guides, embodiments of the present invention allow the manipulation of such fragile elongate members safely and reliably without compromising the integrity of the elongate member.

Embodiments of the present invention allow to use a single gripper for manipulation of a plurality of elongate members having different geometric properties. For example, a gripper may allow the manipulation of elongate members having a diameter $d_c$ within the range according to equation 7:

$$d_c \in \{d_{min}, d_{cmax}\} \tag{7}$$

wherein the elongate member diameter $d_c$ satisfies equation 8:

$$d_b \leq d_c \text{ for } L \geq L_{min} \tag{8}$$

such that the sleeve is capable of gripping the elongate member over a distance L greater than a minimum distance $L_{min}$. The minimum distance $L_{min}$ can be chosen so as to provide a minimum length over which the elongate member is to be gripped in order to provide a reliable grip withstanding loads which may be applied to the elongate member.

In embodiments of the present invention the range of diameters according to equation 7 for a particular gripper can be altered without requiring alteration of the external geometry of the collars 309, 331. For example, a fixing element 311 with a smaller inner diameter and a receiving element 310 having an inner portion with a smaller inner diameter can allow to accommodate for example a sleeve having a smaller diameter in an equilibrium state. This can allow exchange of the sleeve without requiring adjustment of an external actuation system used to drive the gripper or modification of the clamping elements 102, 103 configured to receive the sleeve.

It is an advantage of embodiments of the present invention that the sleeve 301 and the connector pieces 310, 311 of the collar 309 and corresponding components of the collar 331 can be adjusted such that the range of diameters $d_c$ according to equation (7) can be adjusted without alteration of the external geometry of the collars 309, 331. This is particularly advantageous as it becomes possible to simply exchange the gripping sleeve 301 without requiring altering an external actuation system for driving the gripper and thus elongate member. In some embodiments different collars having different inner diameters and thus capable of coupling to sleeves of different diameters can be used with the same gripper for example by changing the inner diameter of the collars and keeping the outer diameter the same.

Embodiments of the present invention allow to manipulate an elongate member having a cross-section of one or more different shapes such as ellipsoidal, rectangular, squared, hexagonal, octogonal or any other cross-sectional shape that can be gripped by the sleeve which is preferably but not necessarily a cylindrical sleeve.

Figures 20A, 20B, 20C, 20D, 20E, 21:
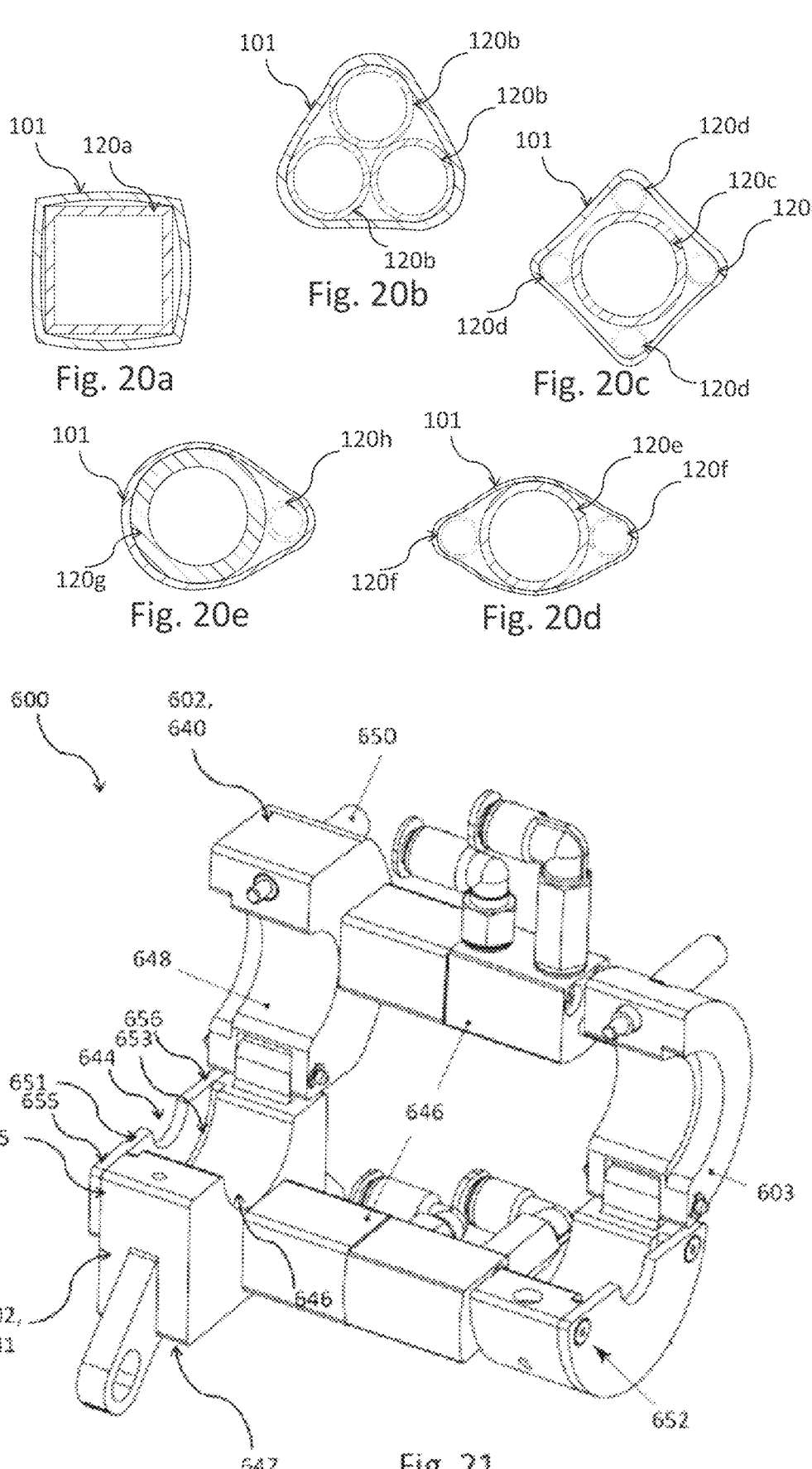
FIGS. 20a-20e, illustrates various combinations of elongate members capable of being manipulated by a sleeve which may be comprised in a gripper according to embodiments of the present invention.
FIG. 21 is a perspective view of a gripper according to embodiments of the present invention without a sleeve and in an open configuration.

Referring to FIG. 20a-e, a sleeve 101 comprised in a gripper according to embodiments of the present invention is capable of conforming to the surface of one or more elongate members having cross-sections which may be circular or non-circular. The configurations of FIG. 20 are examples only and other combinations and cross-sections of elongate members are possible. Referring to FIG. 20a, the sleeve 101 is capable of gripping an elongate member 120a having a square cross-section. Referring to FIG. 20b, the sleeve 101 is capable of gripping a bundle of three elongate members 120b each having an equal circular cross section and arranged in a triangular configuration. Referring to FIG. 20c, the sleeve 101 is capable of gripping a central elongate member 120c having a circular cross section with a first diameter along with four peripheral elongate members 120d each having a circular cross section with a second diameter less than the first diameter and arranged in a diamond configuration around the circumference of the central elongate member 120c. Referring to FIG. 20d, the sleeve 101 is capable of gripping a central elongate member 120e having a circular cross section with a third diameter along with two outer elongate members 120f each having a circular cross section with a fourth diameter less than the third diameter and arranged at diametrically opposite points at the circumference of the central elongate member 120e. Referring to FIG. 20e, the sleeve 101 is capable of gripping a main elongate member 120g having a circular cross section with a fifth diameter along with an adjacent elongate member 120h having a circular cross section with a sixth diameter less than the fifth diameter and arranged adjacent to the main elongate member 120g.

It is an advantage of embodiments of the present invention that multiple elongate members can be simultaneously manipulated. When referring to equations 7 and 8 for multiple elongate members or elongate members having a non-circular cross-section, the diameter $d_c$ is defined as the diameter of the smallest circle circumscribing the cross-section of the elongate member or set of elongate members.

The degree of grip of the elongate member by the sleeve can be controlled by controlling the length L, for example between a minimum and maximum length, by controlling the spacing and/or orientation of the clamping elements 102, 103. The minimum and maximum lengths may be determined experimentally dependent on the elongate member to be driven and the requirements of a particular application.

Preferably the gripper is capable of rapid and controlled switching between a free state with length $L=L_{free}$ in which the elongate member is free to move within the sleeve and a fixed state with length $L_{fix}$ in which the elongate member is fixed with respect to the gripper. In the fixed state there is preferably no or minimal slip between the elongate member and the sleeve.

The gripping state of the gripper can then be specified in dependence upon the length L according to the following equations. The gripping state is fixed when equation 9 is satisfied:

$$\forall L \geq L_{fix} \qquad (9)$$

The gripping state is free when equation 10 is satisfied:

$$\forall L \leq L_{free} \qquad (10)$$

and the state is between a free and a fixed state when equation 11 is satisfied:

$$L \in \{L_{free}, L_{fix}\} \qquad (11)$$

It can be understood that during the transition from free to fixed state and vice versa, somewhere within the interval of equation (11) the transition in state will occur.

In some embodiments it can be helpful to establish accurately at which point the gripping state changes or how L can be controlled to provide a specific gripping force, allow a certain level of slip or control the gripping pressure upon the elongate member. In other embodiments a specific gripping force may not be required and it may be sufficient to know the boundaries of equations (9) and (10) beyond which one can expect that the elongate member is free to move or is fixed.

In some embodiments the transition between a free state and a fixed state may be required to be as rapid as possible and it may be preferably that the sleeve spends a relatively short amount of time in the region defined by equation (11) wherein the gripping state may be uncertain.

It is an advantage of embodiments of the present invention that simple coupling and decoupling of the sleeve to the clamping elements is enabled.

Figure 22:
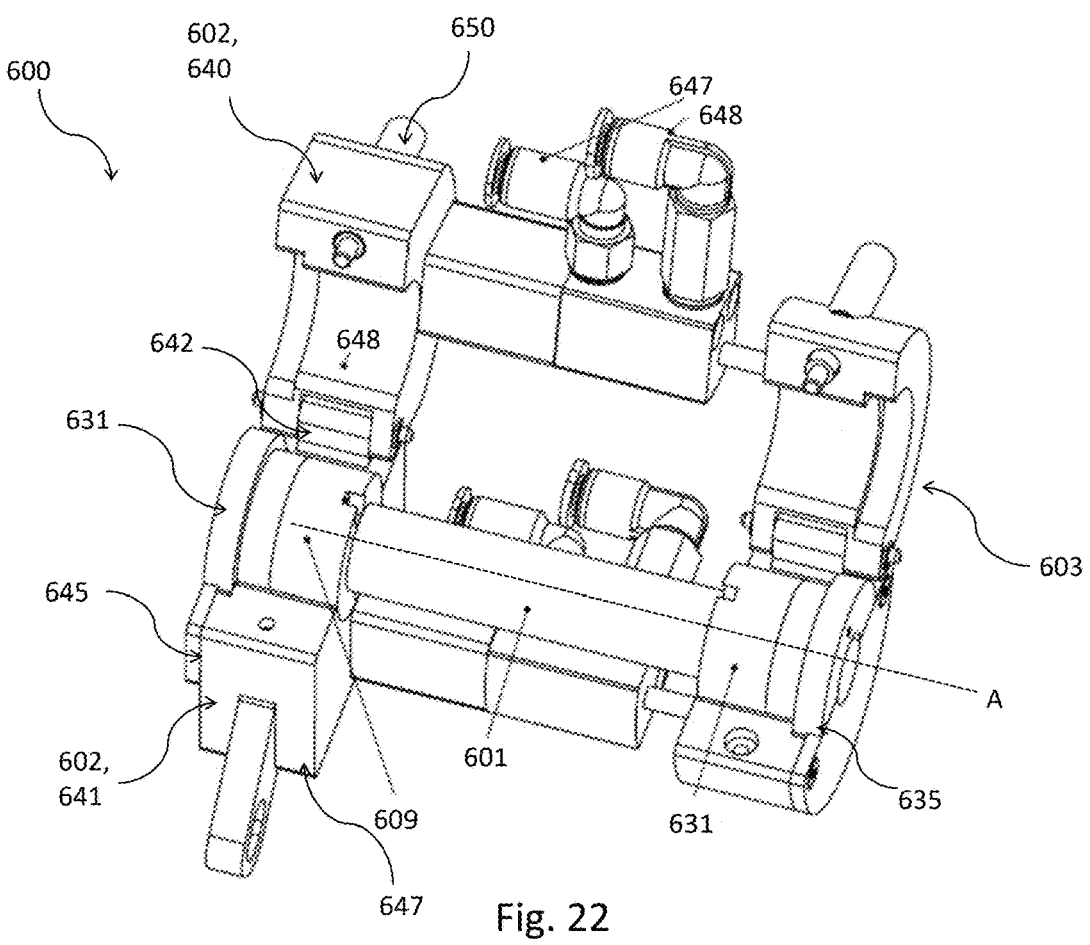
FIG. 22 is a perspective view of a gripper according to embodiments of the present invention with a sleeve and in an open configuration.
Figure 23:
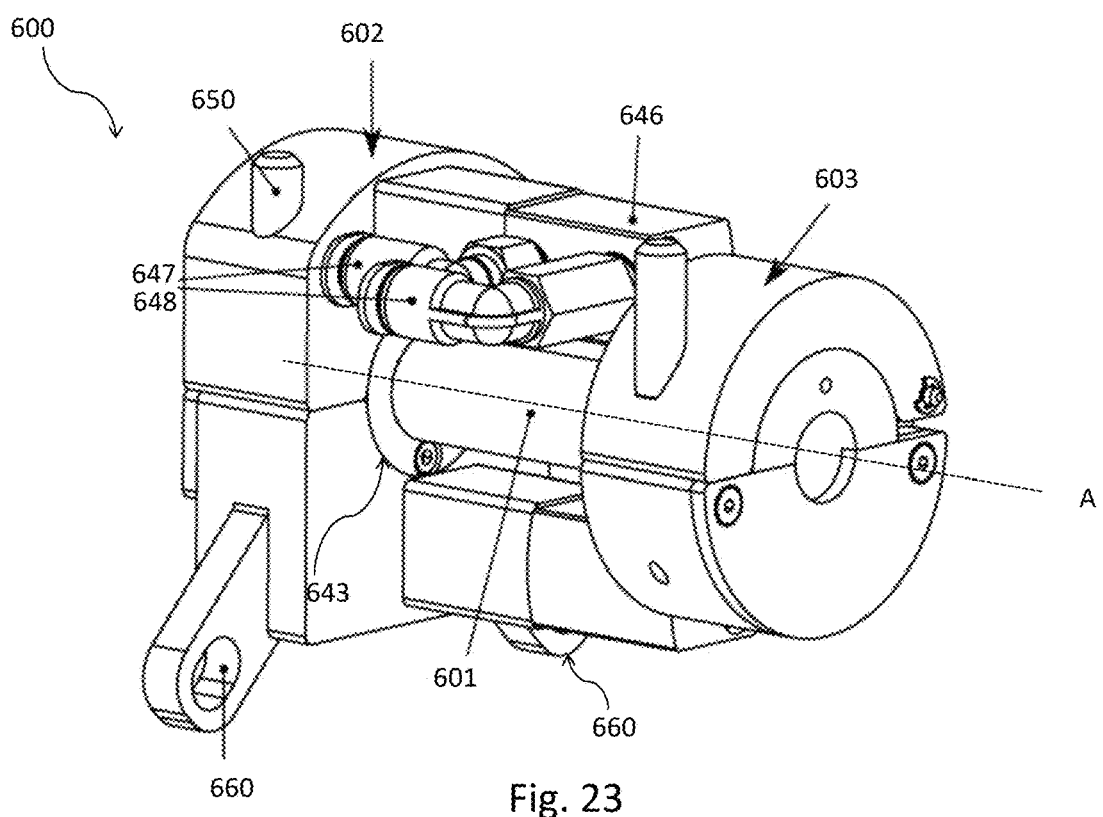
FIG. 23 is a perspective view of a gripper according to embodiments of the present invention with a sleeve and in a closed configuration.

Referring to FIGS. 21, 22 and 23 a gripper 600 according to embodiments of the present invention comprises a sleeve 601, a first clamping element 602, and a second clamping element 603. The sleeve 301 extends between a first end 604 and a second end 605. The first clamping element 602 is configured to receive and removably couple to the first end 604 of the sleeve 601. The second clamping element 603 is configured to receive and removably couple to the second end 605 of the sleeve 601.

Figure 24:
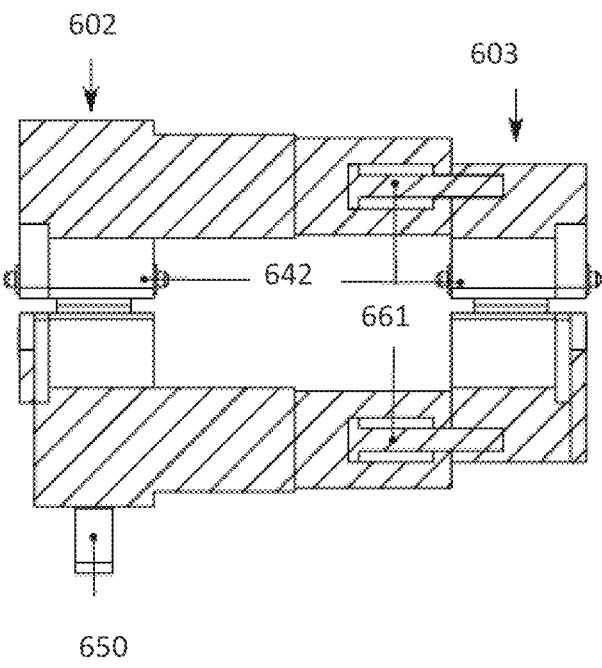
FIG. 24 is a cross-sectional side view of a gripper according to embodiments of the present invention without a sleeve.
Figure 25:
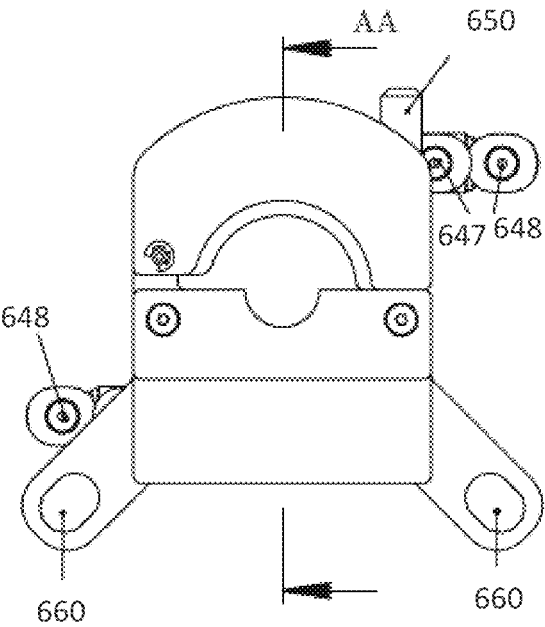
FIG. 25 is an end view of a gripper according to embodiments of the present invention without a sleeve.
Figure 26:
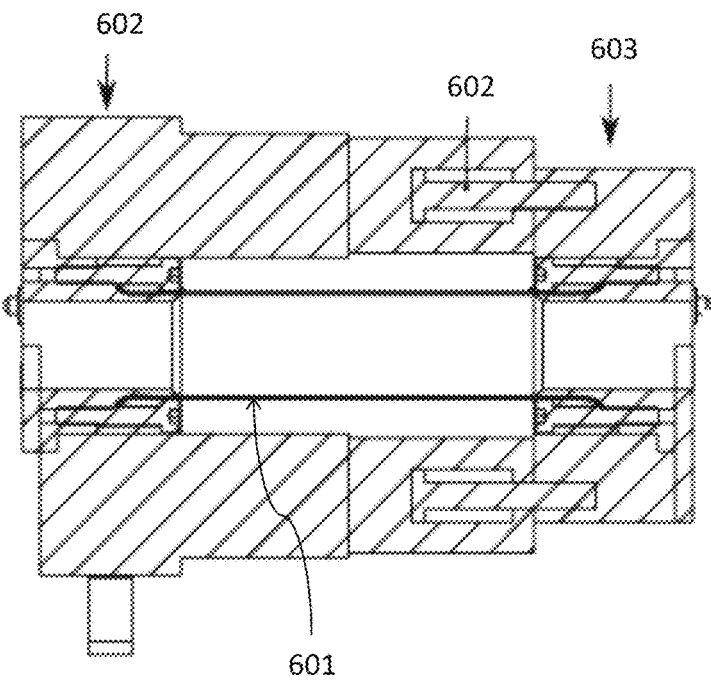
FIG. 26 is a cross-sectional view of a gripper according to embodiments of the present invention with a sleeve.
Figure 27:
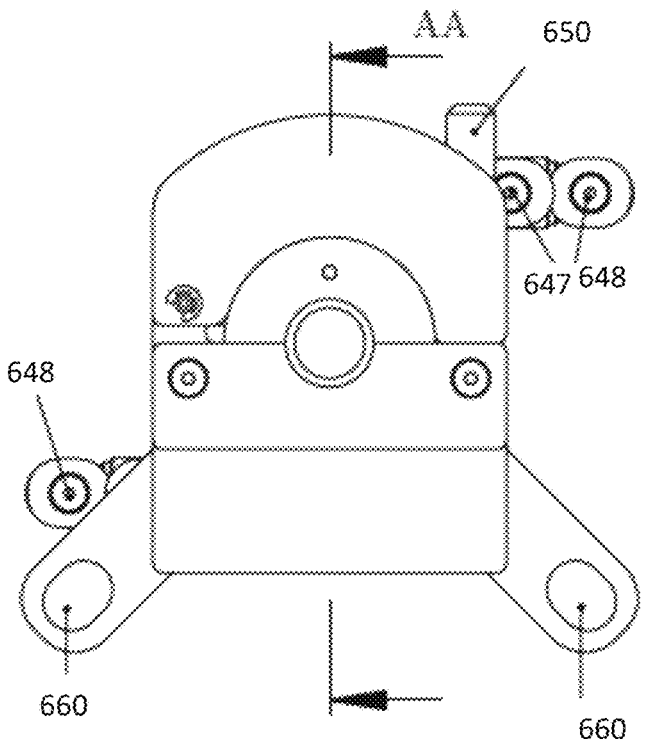
FIG. 27 is an end view of a gripper according to embodiments of the present invention with a sleeve.

A side and end projection of the gripper without the sleeve are shown in FIGS. 24 and 25 respectively. A side and end projection of the gripper including the sleeve 601 are shown in FIGS. 26 and 27 respectively.

Referring in particular to FIG. 21, the first and second clamping elements 602, 603 are shown without the sleeve 601 in an open configuration for receiving a sleeve 601 (FIG. 22).

The first clamping element 602 has a generally tubular form comprising a first half-tubular portion 640, and a second half-tubular portion 641 coupled to the first half-tubular portion 640. The first half-tubular portion 640 and the second half-tubular portion 641 each have a form such as that created by slicing a tube through a plane including the central axis of the tube. The first and second half-tubular portions 640, 641 are coupled by a hinge connection 642 such that in a closed configuration (FIG. 23) the first clamping element has the form of a tube with a central aperture 643 extending between a first opening 644 at a first end 645 of the first clamping element 602 and a second opening 646 at a second end 647 opposite the first end 645 of the first clamping element 602. The central aperture 643 has an interior surface 648. In an open configuration (FIGS. 21 and 22), sideways access is provided to the interior of the clamping element 602; that is, the interior surface 648 of the aperture 643 can be accessed not only in a longitudinal direction through the first and second openings 644, 646 of the clamping element 602 but also in a radial direction.

The first clamping element 602 can be secured in a closed configuration by tightening fixation screw 650 located opposite the hinge connection 642 and configured to couple the first and second half-tubular portions 640, 641 so as to form a tube shape.

The first clamping element 602 comprises a cover portion 651 which is fixed at the first end 645 of the first clamping element 602, for example using bolts 652 (shown in FIG. 21 as for the second clamping element 603). The cover portion 651 has a semi-circular shape with a semi-circular cut-out and is arranged such that the semi-circular cut-out is aligned with the sleeve axis. The first and second half-tubular portions 640, 641 each have a lip at an end adjacent to the cover portion 651 such that a radially extending recess 653 is formed between the cover portion 651 and the first and second half-tubular portions 640, 641. The recess 653 can receive an end portion 631 of a collar 609 attached to the sleeve 601 as described hereinbefore with reference to FIG. 13.

The second clamping element 603 is configured in a similar manner to the first clamping element 602.

The first and second clamping elements 602, 603 can be secured in a closed configuration by tightening fixation screws 650.

In this manner a sleeve 601 can be fixed to first and second clamping elements 602, 603. The separation of the first and second ends of the sleeve 601 can be changed by changing the separation of the first and second clamping elements 602, 603.

The distance between the first and second clamping elements 602, 603 can be controlled for example by using a pair of pneumatic pistons 646. The pistons 646 are configured to provide a force for extending the sleeve as well as the guidance to move both clamps and connector ends along a linear translational direction that is parallel to the sleeve's longitudinal axis.

The pistons 646 are each provided with a two-way air supply through inlets 647 and outlets 648. The pistons 646 provide a compact drive system for controlling the sleeve length L. Preferably the pneumatic pistons 646 are lightweight as compared to the motor and very fast so as to allow rapid switching between fixed and release state, for example less than 50 ms.

In some embodiments, the pistons 646 can be provided with a pressure release valve (not shown). This can allow to establish an upper limit on the force that can be applied to the sleeve through driving of the clamping elements 602, 603 by the pistons 646. For example, the pressure release valve may activate if air pressure in the air supplied through the inlet valve exceeds a specified level. In some embodiments, the pistons 646 comprise MRI-compatible materials.

Other methods for clamping the sleeve and driving the clamping elements are possible within the scope of the present invention. For example, in some embodiments the clamping elements are driven by a drive system comprising one or more solenoids, one or more voice-coil motors, a rack-and-pinion transmission, a lead-screw, a linear capstan together with conventional rotary electromagnetic actuators, or other linear actuators such as artificial muscles or linear electromagnetic motors.

In embodiments of the present invention, in addition to allowing control of the spacing of the first and second ends of the sleeve 601, the gripper is 600 capable of controlling the orientation of the sleeve about the sleeve axis A.

The semi-circular cover portion 651 of the first clamping element, and a similar cover portion of the second clamping element, co-operates with the non-axisymmetric shoulder portions 635 in the collars 609, 631 such as the shoulder portions 635 (FIG. 13) allow to lock the sleeve 601 within the clamping elements such that the sleeve 601 cannot rotate relative to clamping elements about the sleeve axis. That is, the faces 636, 637 of the collar 609, as shown in more detail in FIG. 13, are arranged in contact with faces 655, 656 of the cover portion 651 which are planar faces parallel to the sleeve axis, thus preventing the collar 609, and therefore the sleeve, from rotating with respect to the clamping element. By controlling the orientation of the gripper about the sleeve axis it is therefore possible to also control the orientation of the sleeve and, when in a gripping state, the orientation of an elongate member gripped by the sleeve.

Referring in particular to FIG. 23, the gripper 600 may comprise a pair of connectors 660 for connecting the gripper 600 to a drive system (not shown) which may be configured to control the pose, twist, acceleration or jerk of the gripper system 200 or that may impart a wrench upon the gripper system 200.

Where the 'pose' of the elongate member is referred to this corresponds to its 3-dimensional position and 3-dimensional orientation in space and where this pose can be defined at the level where the elongate member is gripped. This point may not necessarily be the centre of the sleeve in the longitudinal direction, for example in the case of a varying diameter of the elongate member. Also at this location the 'twist' or 3-dimensional translational velocity and 3-dimensional rotational velocity can be controlled via the gripper. The same holds for the acceleration and the jerk at the level of the gripper.

An elongate member may be in some embodiments a deformable rather than a rigid body which may mean that changes in pose, twist, acceleration and jerk may be only partially transferred to parts of the elongate member not held by the gripper. Embodiments of the present invention can be positioned in close vicinity to the location on the elongate member which is desired to be controlled with high precision or at high bandwidths and speeds.

Where a 'wrench' is referred to it is meant a 3-dimensional force component and a 3-dimensional torque component.

Embodiments of the present invention may comprise one or more force and/or torque sensors on or adjacent to the collars 609, 631 for measuring the wrench applied to the elongate member. Embodiments of the present invention allow to then estimate the wrench applied by the elongate member on an external body. For example, the elongate member may comprise a catheter, and embodiments of the present invention allow to control the force and the torque applied by the catheter upon a vessel structure.

This can help to prevent accidents or damage such as tissue damage, dislocation of plaques or piercing the vessels, the heart or other crucial organs. The measured force or torque may be used to provide haptic feedback or visual feedback to an operator or control system, which can then limit the intensity of forces, torques, speeds, accelerations, jerks or other parameters of the elongate member.

As the sleeve is not infinitely rigid, a discrepancy may exist between the motion of the gripper 600 and the motion of an elongate member under manipulation. If the elongate member is not securely gripped or the applied wrench is excessively large, slip may develop between the elongate member and the sleeve.

The gripping action of the sleeve in some embodiments may not be immediate. While L is adjusted between $L_{free}$ and $L_{fix}$ and vice versa, the elongate member may not be held completely fixed with respect to the gripper and friction between the elongate member and the moving sleeve can give rise to a wrench being applied to the elongate member, which can cause unintended motion of the elongate member during this transition period.

Embodiments of the present invention allow to reduce the effect of such non-ideal behavior such that desired poses, twists, wrenches, accelerations or jerks can be transmitted to the elongate member with reduced discrepancy, for example by reducing the contraction/extension speed or using multiple grippers.

Figure 28B:
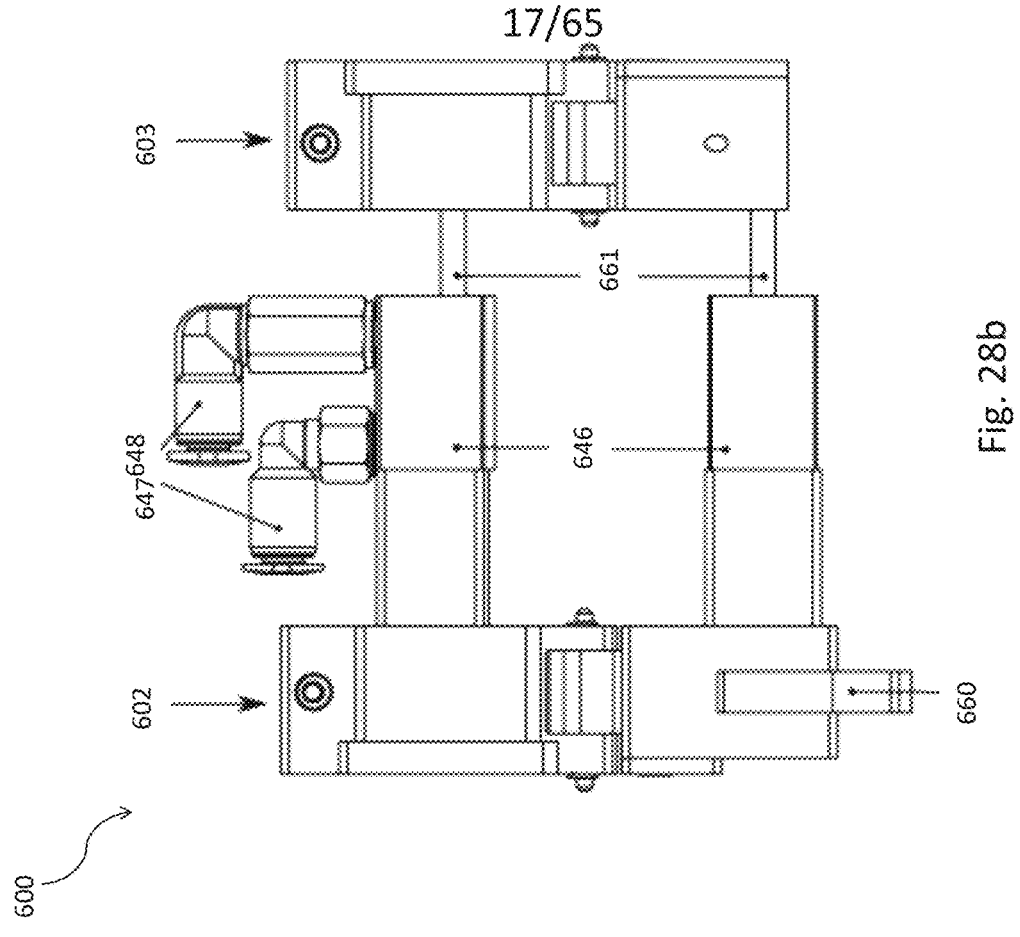
FIG. 28b is a cross-sectional view of a gripper according to embodiments of the present invention with a sleeve in an extended configuration.
Figure 28A:
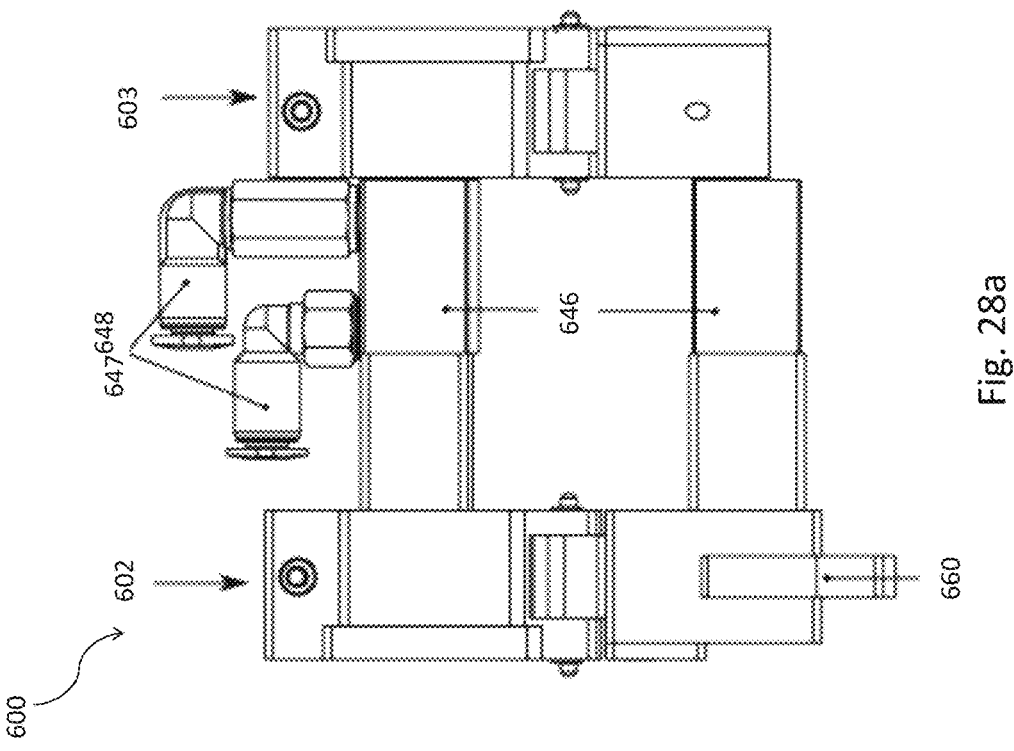
FIG. 28a is a cross-sectional view of a gripper according to embodiments of the present invention with a sleeve in a non-extended configuration.

Referring to FIGS. 28a and 28b, the working of the pistons 646 is shown in more detail. FIG. 28a shows the gripper 600 without the sleeve in a retracted state. FIG. 28b shows the gripper 600 without the sleeve in an extended state and shows piston rods 661 which connect the pistons 646 to the second clamping element 603 and allow translation of the second clamping element 603 with respect to the first clamping element 602.

In the following paragraphs a preferred embodiment to realize such propulsion or retraction motion is explained. However, it is obvious that the described method may be exchanged with other methods belonging to the state-of-the-art for providing linear motion along a certain axis.

Figure 29:
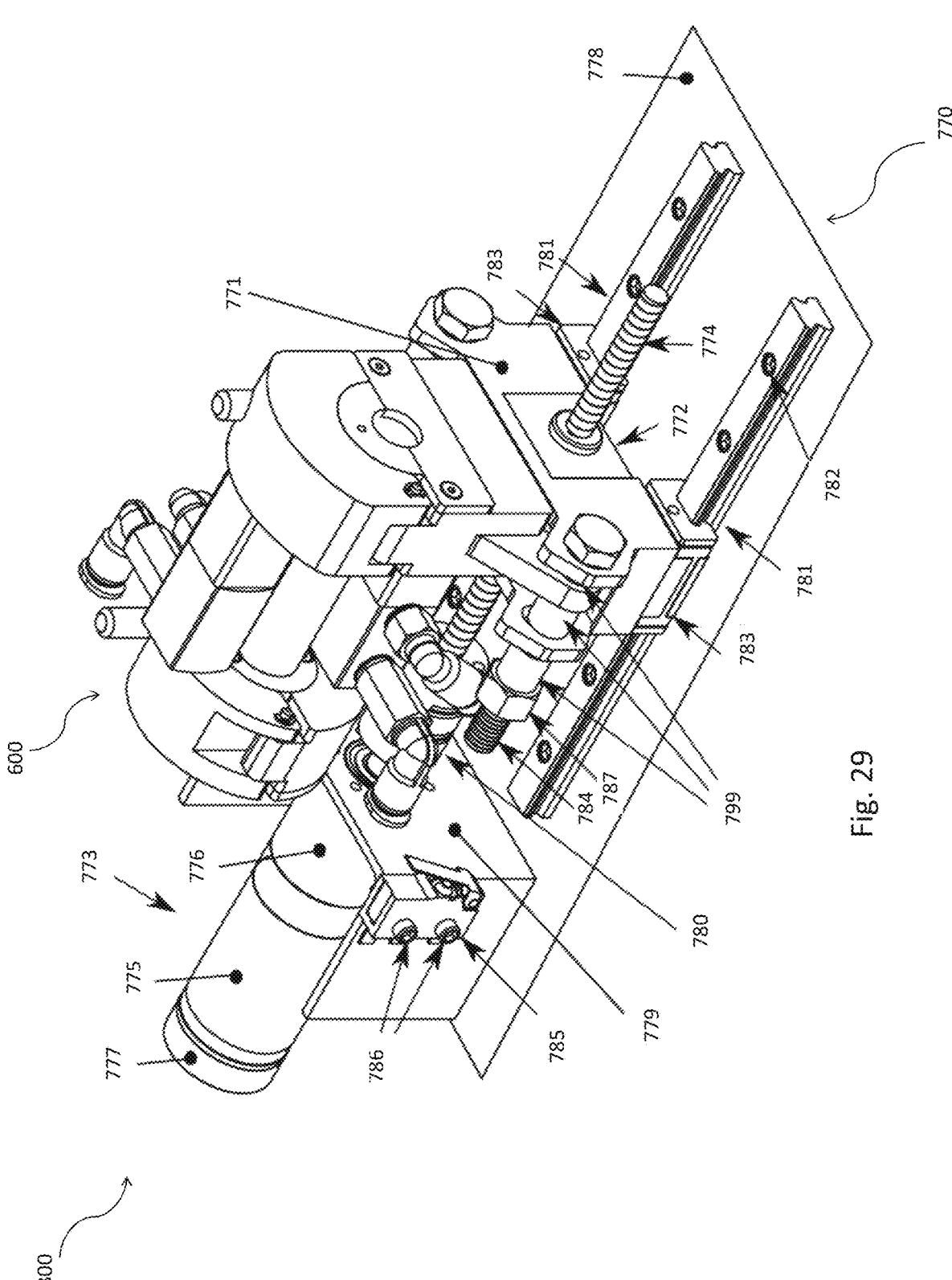
FIG. 29 is a perspective view of a device according to embodiments of the present invention.

Referring to FIG. 29, a gripper 600 according to embodiments of the present invention may be mounted on a spindle drive 770 to form a device 800 for manipulating an elongate member.

The device 800 comprises a mounting piece 771 for connecting the gripper 600 to the spindle drive 770. The mounting piece 771 houses a spindle nut 772 which is configured to be driven by a motor assembly 773 capable of rotating the spindle 774.

The motor assembly 773 comprises a rotary electromotor 775 with an optional reduction mechanism 776 and position sensor such as an encoder 777 to measure the motor's position. The motor assembly 773 is attached to a base plate 778 by means of a mounting bracket 779.

The output motor axis may be coupled through a coupling piece 780 to the spindle 774 which is configured to drive the nut 772, and with it the gripper mounting piece 771 and thus the gripper 600. This allows translation of the gripper 600.

The device 800 comprises a base plate 778 and a pair of guide rails 781 fixed to the base plate 778 by fixation bolts

782 in such a manner that the guide rails 781 are aligned parallel to each other and form a linear guide so as to constrain the motion of the mounting piece 771 to a translational motion along the sleeve axis.

The device 800 comprises a pair of sliders 783 attached to the mounting piece 771 and co-operating with the guide rails 781 so as to allow motion of the mounting piece 771 along the rails 781.

The device 800 comprises an end-stop screw 784 disposed on the mounting piece 771 and an end-stop sensor 785 disposed on the mounting bracket 779. The end-stop sensor 785 is bolted through a pair of connecting bolts 786 to the mounting bracket 779. The end-stop sensor 785 is configured to detect when the mounting piece 771 is within a certain distance of the mounting bracket 779 such that motion of the mounting piece 771 in a direction towards the mounting bracket 779 can then be limited so as to avoid collision with the mounting bracket 779.

The end-stop sensor 785 could be for example a contact switch configured to switch off the electromotor 775 upon contact with the end-stop screw 784. The end-stop sensor 785 or an additional sensor disposed on the mounting piece 771 may be used to establish a reference position of the mounting piece 771, thus allowing the absolute pose of the gripper 600 with respect to the base plate 778 to be established.

The motion of the mounting piece 771 in a direction away from the mounting bracket 779 can be limited by the end of the spindle 774. The spindle 774 may comprise a mechanical end-stop (not shown) for preventing motion of the mounting piece 771 in a direction away from the mounting bracket 779 beyond a certain point.

To finetune the end-of-stroke and parallel alignment of the gripper 600, which can reduce the need for high tolerance manufacturing, a number of distance spacers 799 (FIG. 29) can be used to fix the gripper 600 to the mounting piece 771. The nuts 787 are used to fix the gripper at both sides of the assembly.

The linear position of the gripper relative to the mounting bracket 779 may be calculated by combining the rotational displacement of the electromotor 775 as measured by the encoder 777 with the lead of the spindle drive 774. By counting the number of encoder-pulses and multiplying this with the lead divided by the total number of encoder-pulses per revolution one obtains an estimate for a linear displacement of the gripper 600.

The propulsion or retraction force that is delivered by the motor 775 upon the gripper 600 may be estimated by modeling the relation between motor current and driving force and by modeling the friction, viscous or inertial components present in the transmission system (including reduction, spindle-drive and linear guides).

Additionally or alternatively, the propulsion or retraction force may be directly measured by integrating a one-dimensional load cell that is sensitive to forces in the longitudinal direction. For example such a sensor may be disposed in the mounting piece 771 for the gripper 600.

Other methods of measuring the linear displacement or the actuation force are possible within the scope of the present invention. For example a magnetic or optical linear encoder may be mounted along the track of a guide rail 781 and a detector may be provided at the mounting piece 771.

From differentiation of the position one may derive through differentiation the associated velocity or acceleration of the gripper 600, which may be used advantageously to improve the dynamic behaviour of the system through feedback control or to follow trajectories with improved precision through feed-forward or feedback control schemes.

The device 800 may comprise additional or alternative sensors for directly measuring the velocity or acceleration of the gripper, for example an accelerator mounted on the gripper 600 or a velocity sensor such as a Hall sensor or gyroscope mounted on the motor 775 or gripper 600.

Whereas the abovementioned measurement approaches and other methods known within the state-of-the-art can measure the position, velocity, acceleration or jerk of the gripper with good accuracy they do not directly measure the position, velocity, acceleration or jerk of the elongate member itself. If slip or deformation due to the compliance of the elongate member occurs, the gripper position, velocity, acceleration or jerk may only approximately correspond to the position, velocity, acceleration or jerk of the elongate member. The device 800 may in some embodiments comprise one or more sensors for directly measuring the translational position of the elongate member.

For example, a pair of passive rollers may be used at the proximal or distal side of the device 800 and aligned with the elongate member such that the elongate member passes through the pair of passive rollers. An encoder or similar sensor may be mounted on one or both of the rollers. By measuring the number of revolutions of the rollers using the encoder or similar sensor the translational movement of the elongate member can be directly measured. The pair of rollers are preferably set up such that they are in constant contact with the elongate member, but as they are passive and do not need to drive the elongate member, the pre-load that is needed to ensure contact is maintained is relatively low such that the elongate member is not easily damaged by the passive rollers.

In another embodiment optical sensors can be directed to the elongate member to measure the optical flow and estimate the velocity based on this information. Particular visual, magnetic or other patterns could be made on the surface of the elongate member which could be detected by such a contact-less sensor leading to an incremental or absolute estimate of the pose of the elongate member. The sensor can for example measure distance between the collars 309, 331 by using a camera to estimate optical flow and then the distance based on this measurement. In some embodiments, a laser distance sensor for example as used in an optical coherence tomography device can be used.

Linear translation of the gripper 600 need not be effected by the spindle drive 770 and other configurations are possible in accordance with embodiments of the present invention. For example pneumatic or hydraulic pistons or artificial muscles may be positioned so as to drive the gripper 600 in a direction parallel to the sleeve axis; linear electromagnetic actuators, solenoids or voice-coil actuators may be employed in a direct drive approach or making use of an intermediate transmission system. Rotary actuators may also be used in any known combination such as via a rack-and-pinion or a capstan to transfer rotatory motion of the actuator to a linear translation of the gripper.

The device 800 may have particular advantages in applications with tight constraints on the overall size of the drive systems or where a simple system with few components is required. Whereas the device 800 allows very precise positioning of the elongate member, the stroke that can be reached without re-gripping is limited to the length of the employed spindle. That is, the distance through which the elongate member can be translated in a single longitudinal movement without release and re-grip of the elongate member by the sleeve is limited to the length of the spindle.

In some applications a relatively long spindle may be chosen in order to increase the available stroke length. In some applications a relatively short stroke length is sufficient. For example the elongate member may first be manipulated manually by an operator to provide rough positioning towards the area of interest and subsequently the gripper 600 may be used when enhanced positioning precision or force control might be needed. For example, a catheter may be inserted up to the heart chamber by a clinician and then the gripper 600 or device 800 may be used the robotic driver to allow precise and dynamic control of the elongate member in contact with the heart.

In some applications it may be acceptable to release the elongate member from the gripper intermittently and to reposition the spindle drive actuation stage 771 to the beginning of its stroke, regrip, and continue with the next stroke. In such embodiments a stabilization device for holding the elongate member steady during a regripping phase may be used. Such a device may be a traditional clamping mechanism or it may be also a sleeve-based clamping mechanism.

Embodiments of the present invention allow to provide smooth dynamic manipulation of the elongate member without limitations on the stroke length or loss of control during a regripping phase.

Figure 30:
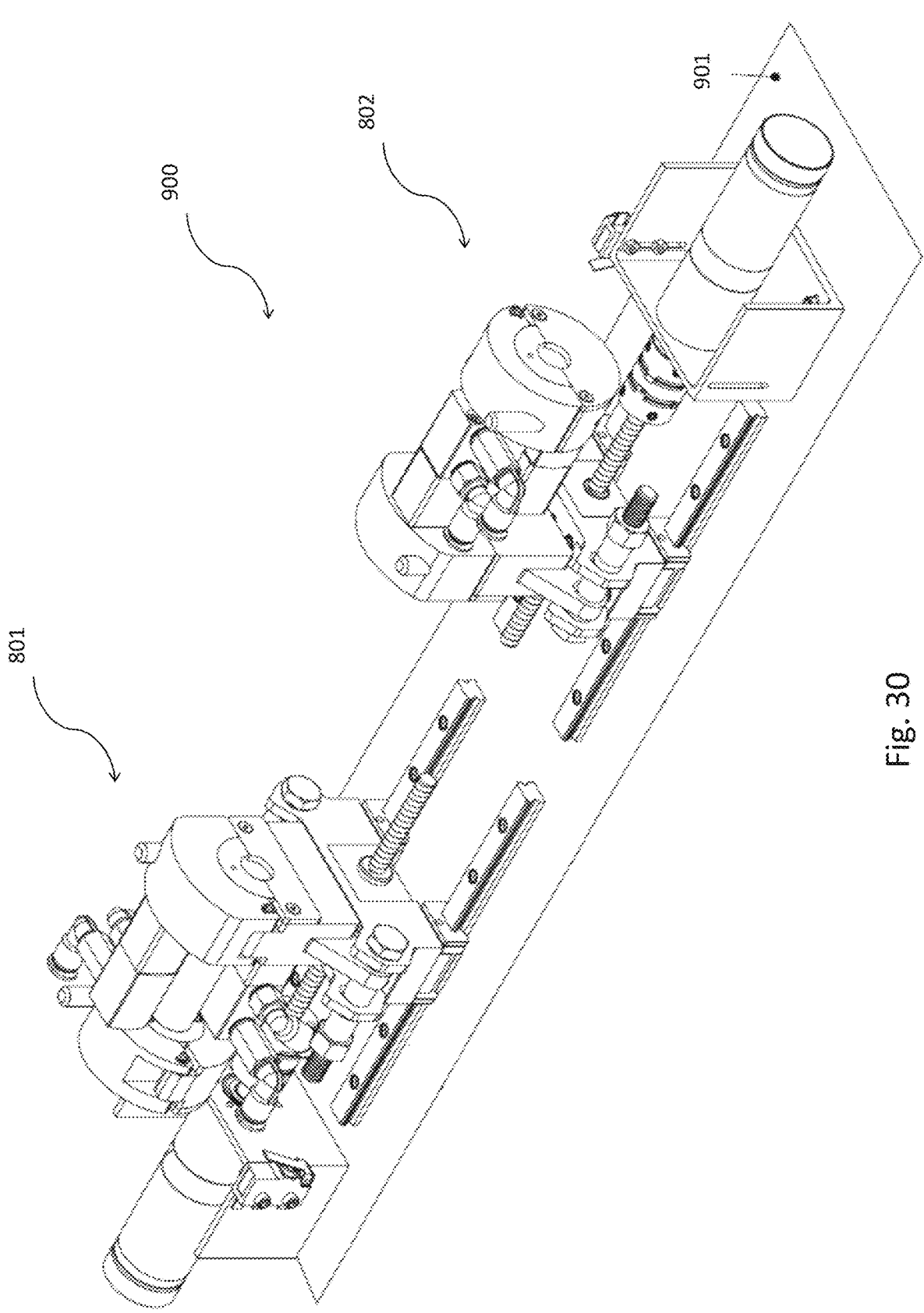
FIG. 30 is a perspective view of apparatus according to embodiments of the present invention comprising two devices of FIG. 29.

Referring to FIG. 30, apparatus 900 according to embodiments of the present invention comprises a first device 801 and a second device 802, the first and second devices 801, 802 being of the form of the device 800 of FIG. 29.

The apparatus 900 comprises a base plate 901. The first device 801 and the second device 802 are mounted on the base plate 901 such that their gripper axes are co-axial. The first device and the second device are positioned such that their respective spindle drives are facing towards each other, that is, if the motor comprised in each device 801, 802 is driven in a forward direction, the grippers comprised in each device 801, 802 will move closer to each other. Embodiments of the present invention allow for other relative configurations of the devices 801, 802 so as to allow unrestricted passage of an elongate member along the axes of the sleeves comprised in each device 801, 802.

Embodiments of the present invention allow to reduce a period during which the position of an elongate member may be less certain, for example when not constrained by at least one of the pair of grippers or where both grippers are in their transition period.

Figure 31:
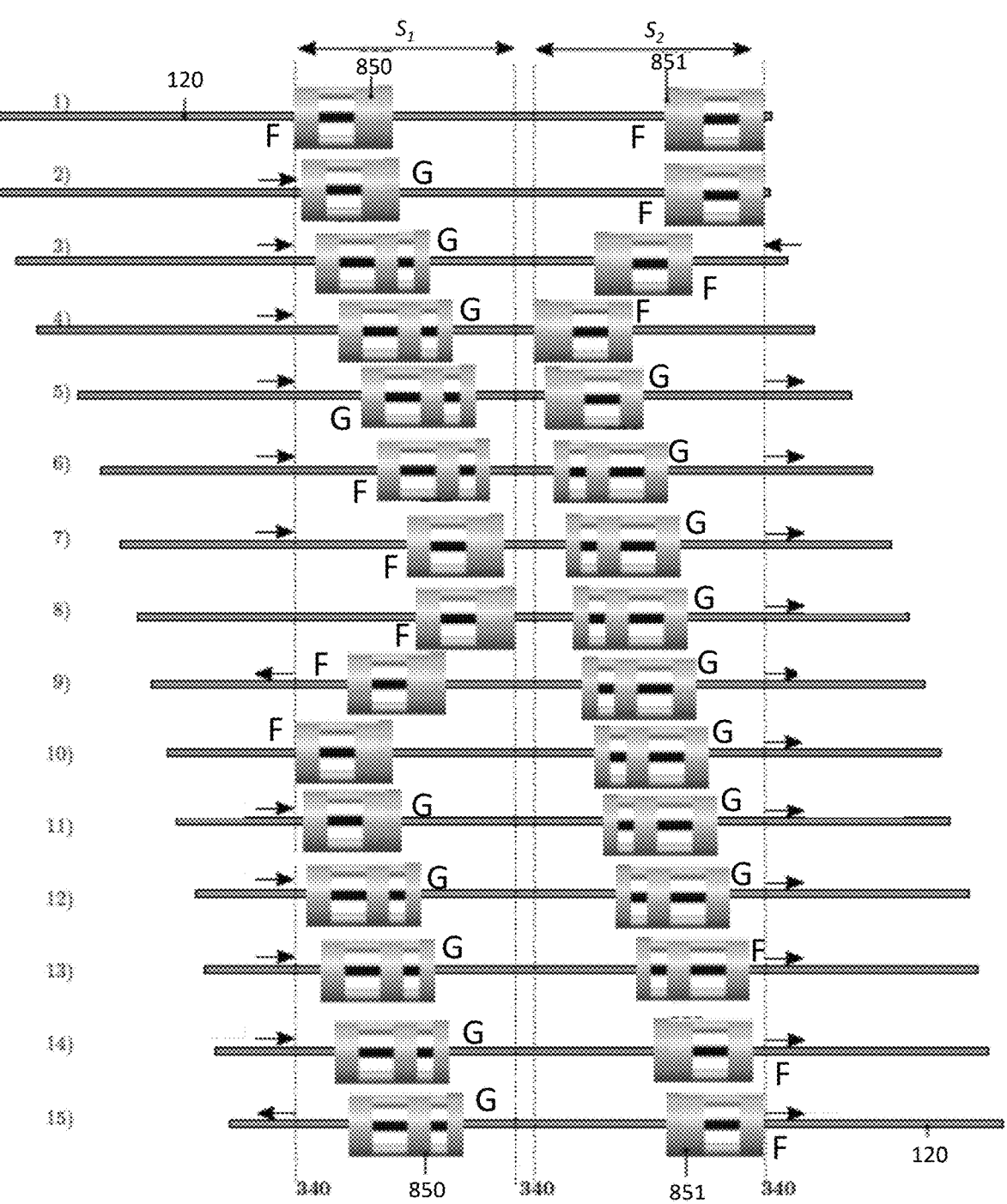
FIG. 31 illustrates a gripping and actuation sequence which may be performed by the apparatus of FIG. 30 for manipulating an elongate member.

Referring to FIG. 31, a gripping and actuation sequence is shown which allows unlimited stroke length and provides controllability of the elongate member over complex motion trajectories. In particular the gripping and actuation sequence allows to establish movement of the elongate member at constant velocity over an unlimited stroke with only a limited deviation of the speed during regripping of the grippers, where this deviation is typically well below deviations that would take place if the elongate member were to be driven by a human operator.

FIG. 31 is an example of a sequence for driving an elongate member 120 at constant velocity v towards the right of the drawing, which will for convenience but without limitation of the invention be referred to as the distal side of the apparatus 900. The sequence may be employed by a first gripper 850 and a second gripper 851 coaxial with the first gripper 850, such as those comprised in apparatus 900. The first gripper 850 is closest to the left, or proximal, side of FIG. 31 and the second gripper 851 is closest to the right, or distal side of FIG. 31. The first gripper 850 and the second gripper 851 have respective strokes $S_1, S_2$ through which they can move, for example using a spindle drive, the strokes each having a proximal and a distal end.

In FIG. 31 a gripper in a release or free state is marked with "F" and a gripper in a gripping state is marked as "G". In the release state an elongate member is free to move through the respective gripper. In a gripping state an elongate member is gripped by the respective gripper and can be translated and manipulated by the gripper. Each row of FIG. 31 depicts a stage in the gripping and actuation sequence which proceeds as follows:

Stage 1

The first gripper 850 is positioned at the proximal end of its stroke and the second gripper 851 is positioned at the distal end of its stroke. Both grippers are in the release state and separated at maximal distance from each other.

Stage 2

The first gripper 850 starts moving towards the distal side with a velocity approaching v. The second gripper 851 moves with speed av with a≥1 (for example a=1.5) towards the proximal side.

Stage 3

When the first gripper reaches speed v the first gripper changes to the gripping state and grasps the elongate member which then also starts to move with velocity v to the distal side. The second gripper remains in the release state and allows unhindered passage of the elongate member through the second gripper.

Stage 4

While the first gripper is still moving with constant speed v to the distal side, the second gripper decelerates as it reaches and stops at the proximal end of its stroke.

Stage 5

The second gripper changes its direction of motion towards the distal end and starts accelerating to speed v. The first gripper is still moving with speed v to the distal side.

Stage 6

When the second gripper reaches velocity v it initiates a gripping action. As gripping may not be instantaneous during the gripping transition period, there may exist at least in some parts of the second gripper a relative velocity difference between the speed of the second gripper's sleeve and the speed of the elongate member. This deviation in speed is at least partially damped by the action of the first sleeve which is still in a griping state and tries to move the elongate member with constant speed v towards the distal side. During a brief period both grippers hold the elongate member gripped and move with speed v towards the distal side.

Stage 7

The first gripper releases the grip upon the elongate member and starts to decelerate once the grip is released. The first gripper is in the release state at the end of stage 7.

Stage 8

The first gripper stops at the distal end of its stroke and reverses its direction of motion.

Stage 9

The first gripper moves back towards the proximal end of its stroke with a velocity av.

Stage 10

While the second gripper is still moving towards the distal end of its stroke with constant velocity v, the first gripper decelerates and reaches the proximal end of its stroke.

Stage 11

The first gripper now reverses direction and starts to move with a speed approaching v towards the distal end of its stroke. The second gripper is still moving the elongate member with speed v towards the distal side.

Stage 12

As soon as the first gripper reaches speed v it changes to a gripping state and grips the elongate member.

Stage 13

During a brief period of time both grippers grip the elongate member and move it at the same speed v towards the distal side.

Stage 14

The second gripper now releases the elongate member and starts to decelerate.

Stage 15

As the second gripper reaches the distal end of its stroke its direction of motion is reversed and it moves with speed av towards the proximal end of its stroke. The cycle then returns to stage 2.

EXPERIMENTS

The sequence of FIG. 31 was implemented in the system of FIG. 30 for an elongate member representing a "dummy" catheter having a diameter of 4 mm. A cable-guide sleeve with a length of 40 mm and diameter of 6.5 mm was used as a gripper sleeve.

The effect of actuation of the grippers, to move from a gripping state to a release state and vice versa, on catheter tip motion was investigated. An ideal response would be an instantaneous grip with no uncontrolled motion of the tip upon gripping and releasing. The catheter was introduced in a sleeve based gripper in released state and a laser distance sensor was positioned co-axial with the catheter for measuring the relative displacement of the catheter tip. The catheter tip motion during gripping and releasing was measured.

Figure 32:
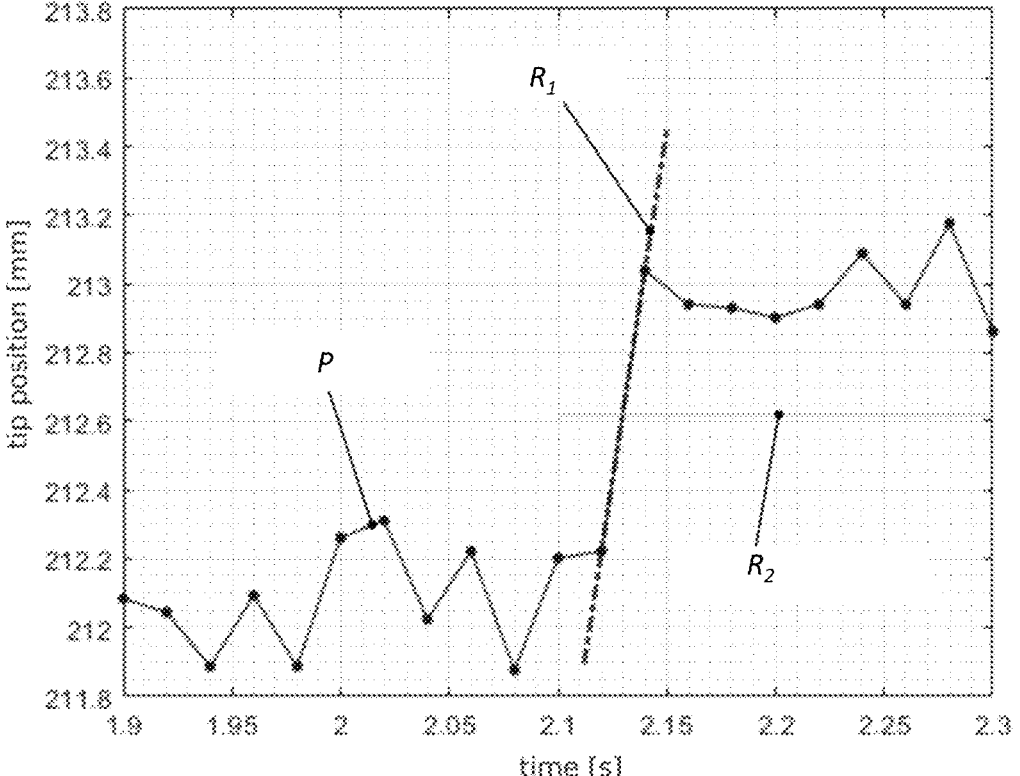
FIG. 32 is a plot of catheter tip position as a function of time for actuation of a catheter by apparatus according to embodiments of the present invention.

Referring to FIG. 32, the catheter tip position is shown as a function of time t. The data are labelled P. At t=2.12 seconds a relatively large change in the catheter tip position can be seen between a first position and a second position, and a distance of approximately 1 mm is moved when the catheter body is gripped. The dashed line $R_1$ in FIG. 32 shows a rise line corresponding to this large change in catheter tip position. A time constant $\tau$ can be calculated as being the time taken for the catheter tip to move from the first position through a distance which is 63% of the distance between the first position and the second position (denoted by the line $R_2$). The rise time or time constant can be seen to be approximately 15 ms.

An investigation of the effects of sleeve extension/retraction on the catheter's tip position were made with a maximum pressure of 5 bar applied to the piston. The sleeve configurations tested are set out in Table 1. When a sleeve is extending or retracting this action takes place between points of full extension and full retraction. Here, sleeve 2 is closer to the free end of the catheter tip than sleeve 1.

TABLE 1

| Sleeve configurations | |
| --- | --- |
| sleeve configuration | Configuration |
| 1 | sleeve 1 fully extended, sleeve 2 extending |
| 2 | sleeve 1 fully extended, sleeve 2 retracting |
| 3 | sleeve 2 fully extended, sleeve 1 extending |
| 4 | sleeve 2 fully extended, sleeve 1 retracting |

Figure 33B:
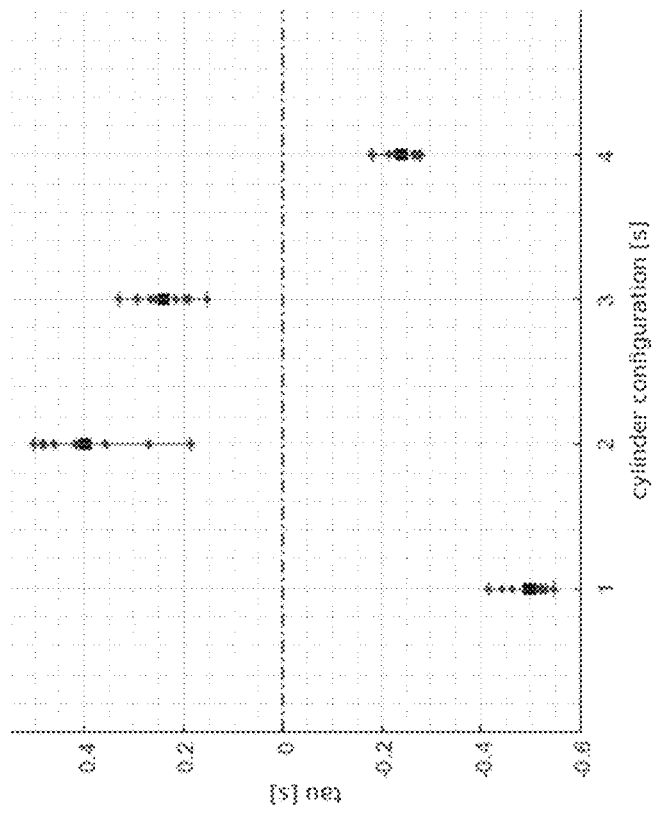
FIG. 33b is a plot of time constants for sleeve configurations as set out in Table 1.
Figure 33A:
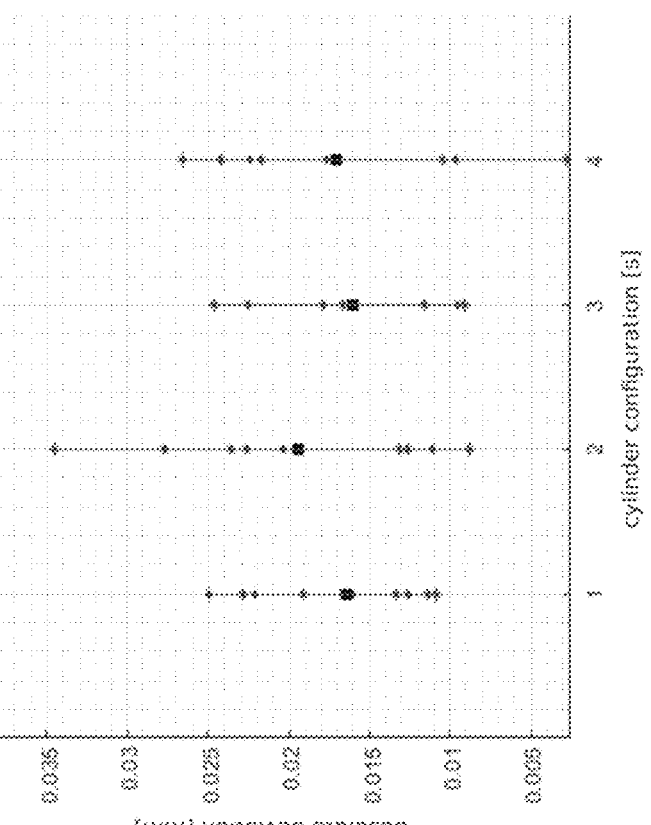
FIG. 33a is a plot of catheter tip deviation for sleeve configurations as set out in Table 1.

Referring to FIG. 33a, the tip deviation is shown for the sleeve configurations of Table 1. Referring to FIG. 33b, the time constant is shown for the sleeve configurations of Table 1. When sleeve 2 is fully extended (configurations 3 and 4), the tip deviation is much lower than when sleeve 1 is fully extended. This is thought to be because sleeve 2 is closer to the free end of the catheter tip than sleeve 1, and when fully extended sleeve 2 can allow for a minimal possible tip deviation. This can be taken into account when devising a control strategy for the sleeve extension/retraction.

The effects of external forces on the catheter were also investigated. The sleeve's compliance (mm/N) gives an indication on the amount of sleeve extension achieved per unit force applied to the sleeve ends. The relationship between the sleeve's extension and the applied force may be nonlinear. Furthermore, in some embodiments the sleeve may not extend at all until a certain force threshold is reached.

Figure 34:
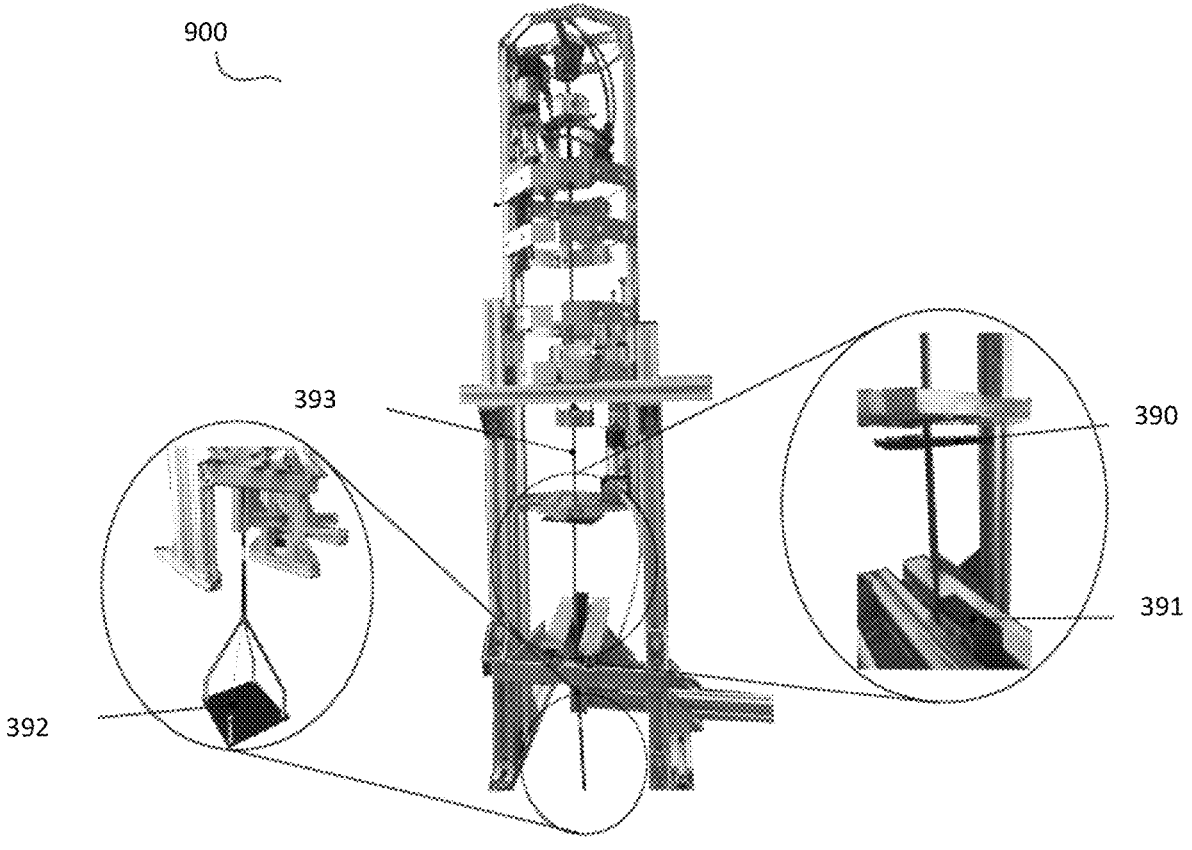
FIG. 34 illustrates an experimental setup for measuring catheter tip displacement effectuated by apparatus according to embodiments of the present invention.

To measure the catheter tip deviation relative to applied loads, the entire catheter driver setup 900 is held vertically as shown in FIG. 34. A plate 390 is placed as horizontal as possible and is positioned above a laser sensor 391. The end tip of a catheter 393 clamped in the catheter driver setup 900 is connected to another plate 392 where cumulative weights will be added. When weights are added to the bottom plate, any deviation encountered by the catheter's tip will be measured by the laser sensor to the top plate.

Each sleeve is first tested separately to measure the independent weight effects, then both sleeves are tested concurrently. The maximum allowable load before slippage for each sleeve configuration was determined. The measurements were performed for each distinct weight added onto the lower plate. Table 2 summarises the results.

TABLE 2

| added weight and applied forces for sleeve configurations | | |
| --- | --- | --- |
| sleeve configuration | Maximum added weight in grams | Maximum force in Newton |
| sleeve 1 only | 1100 | 10.8 |
| sleeve 2 only | 1528 | 15.0 |
| sleeve 1 and 2 | 2638 | 25.9 |

Figure 35A:
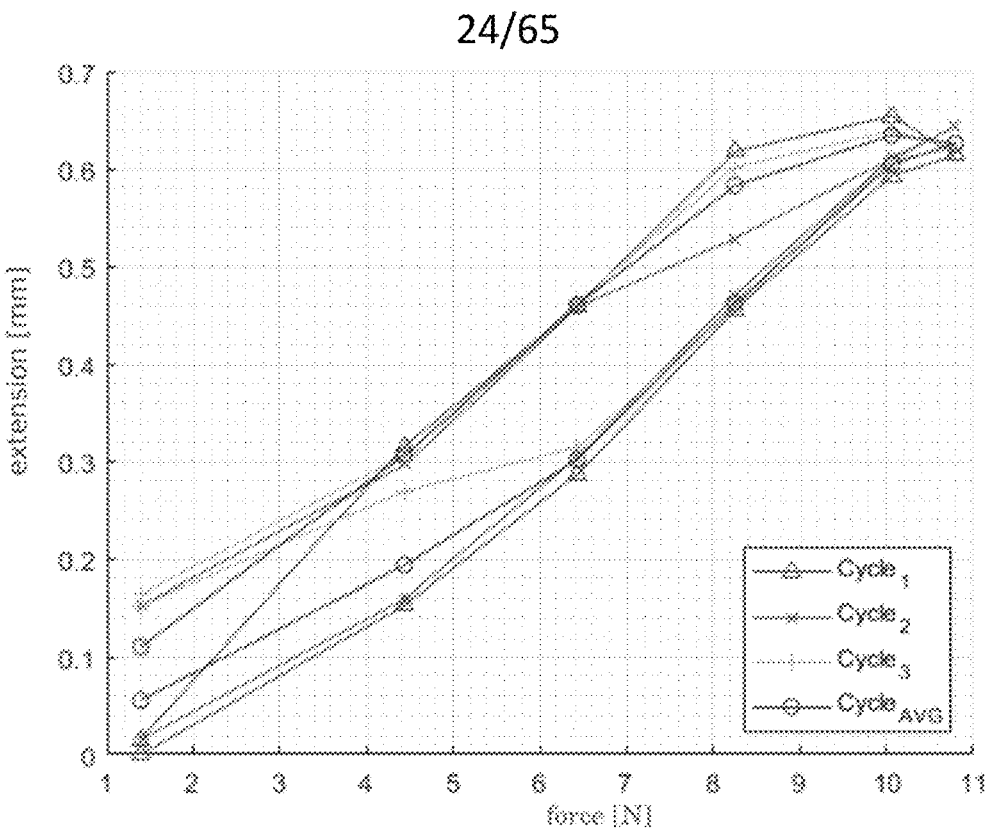
FIG. 35a is a plot of plate deviation as a function of added weight for the setup of FIG. 34 comprising a first sleeve only.
Figure 35B:
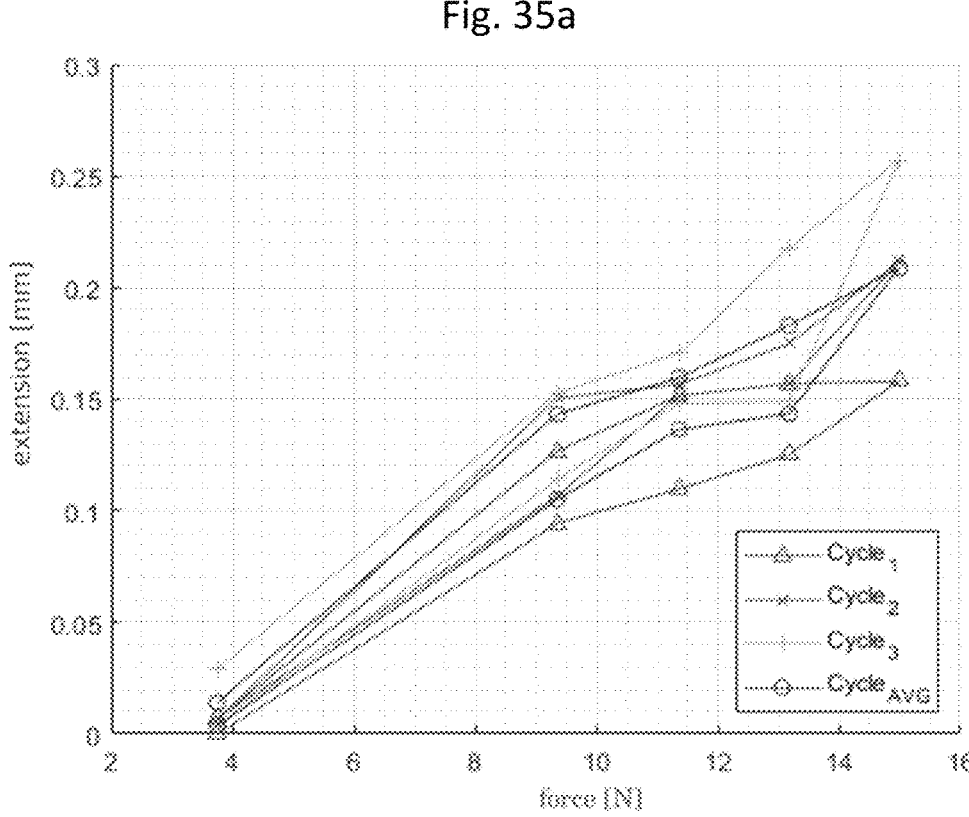
FIG. 35b is a plot of plate deviation as a function of added weight for the setup of FIG. 34 comprising a second sleeve only.
Figure 35C:
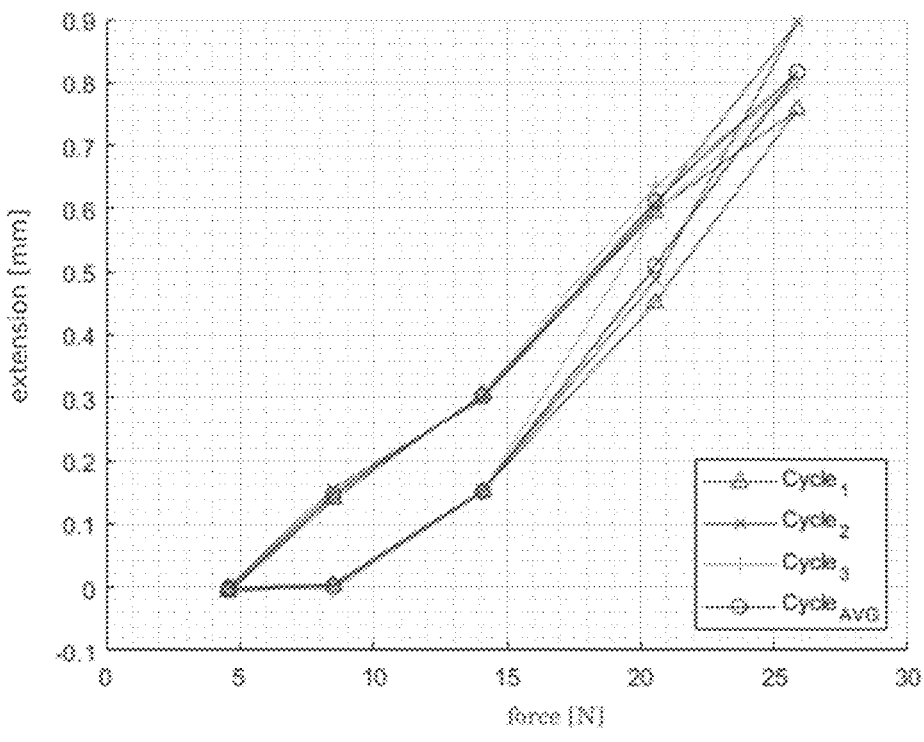
FIG. 35c is a plot of plate deviation as a function of added weight for the setup of FIG. 34 comprising a first sleeve and a second sleeve.

Weights were gradually added to the bottom plate of the setup shown in FIG. 34 up to the maximum allowable weight. Once the maximum allowable weight is reached, the weights are then gradually removed. The procedure is then repeated for two more cycles resulting in three cycles in total. The plate deviation is measured for each added weight. FIG. 35a shows the results for sleeve 1 only, FIG. 35b for sleeve 2 only, and FIG. 35c for sleeves 1 and 2 combined. It can be seen that the sleeves exhibit hysteresis behavior. The behavior of the sleeves can therefore be considered to be repeatable with added forces. The average hysteresis curve is used to compute the compliance slopes by calculating the slope of a line connecting the maximum and minimum points of the hysteresis. Table 3 shows the results for the sleeve compliances.

TABLE 2

| Sleeve compliances | | | |
| --- | --- | --- | --- |
| sleeve configuration | Slope 1 [mm/N] | Slope 2 [mm/N] | Slope AVG [mm/N] |
| sleeve 1 only | 0.0638 | 0.0577 | 0.0608 |
| sleeve 2 only | 0.0171 | 0.0172 | 0.0172 |
| sleeve 1 and 2 | 0.0399 | 0.0386 | 0.0393 |

Figure 36A:
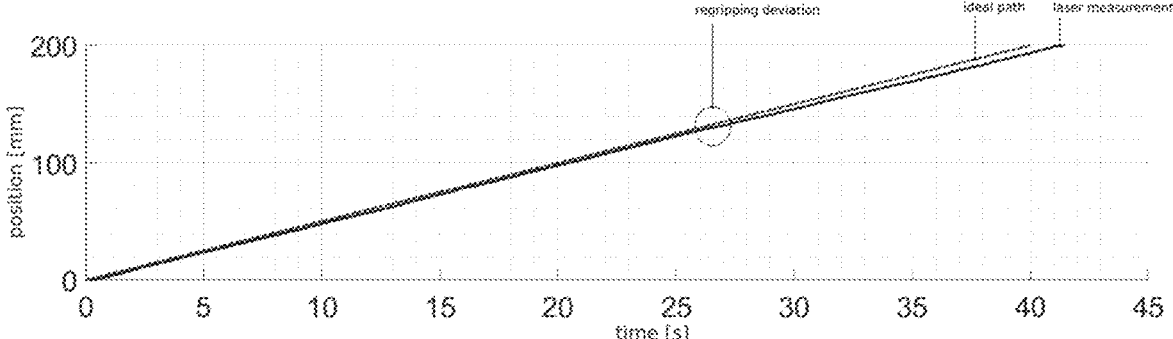
FIG. 36a is a plot of calculated and measured catheter tip position for a catheter actuated by apparatus as shown in FIG. 34.
Figure 36B:
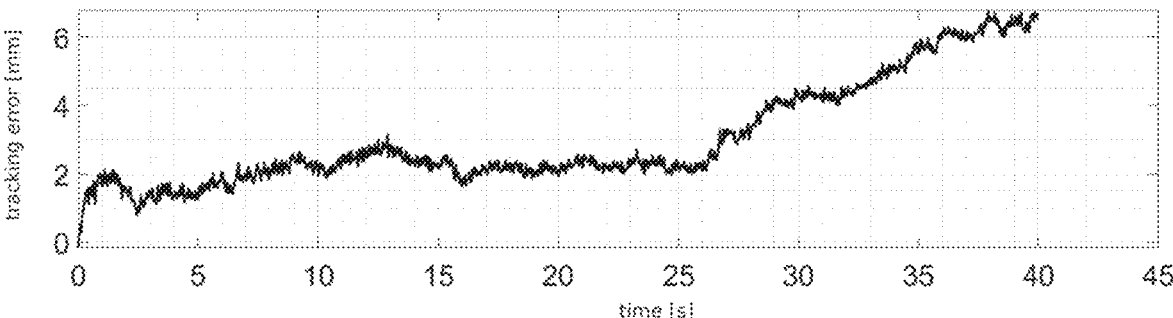
Figure 38:
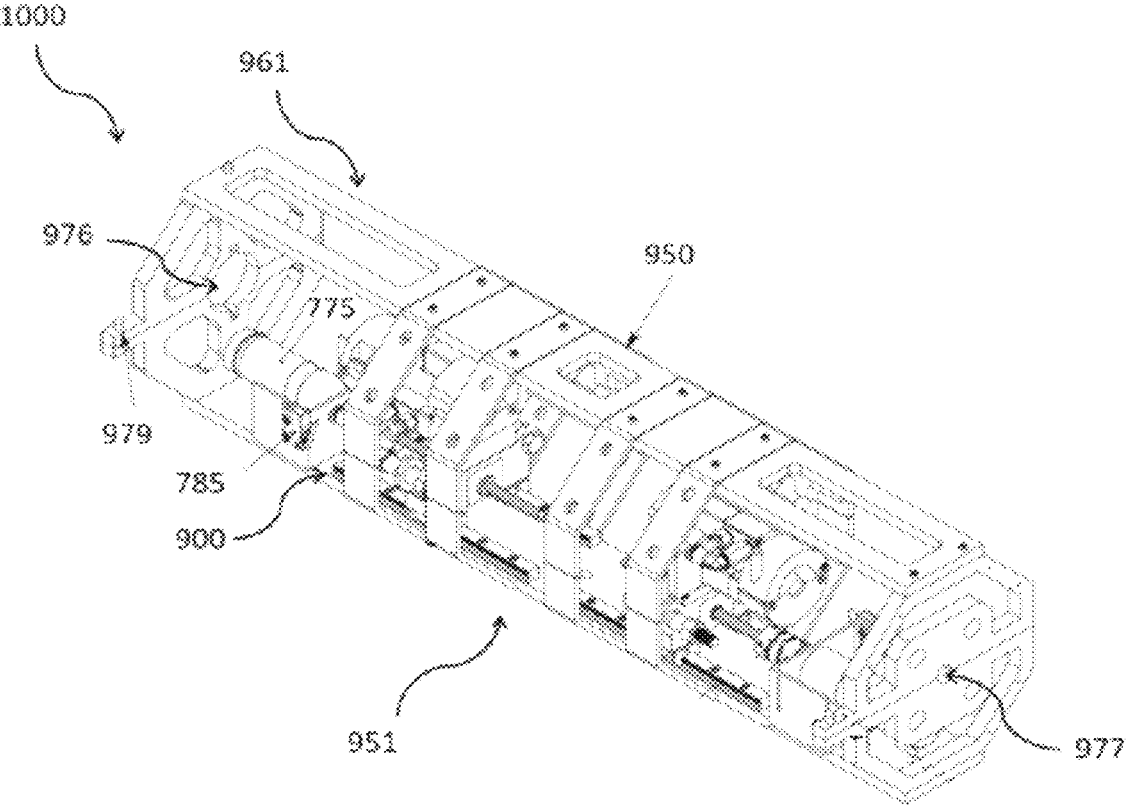
FIG. 38 is a perspective view of apparatus according to embodiments of the present invention in a closed configuration.

The translation mechanism was tested using a catheter driver 1000 as shown in FIG. 38. A laser sensor (Baumer, OADM 13U6475/S35A) with an accuracy of around 40 microns was used to measure the distance between the catheter tip and the sensor (position ground truth). A targeted travel range of 200 mm for the catheter tip was set. Each gripper has a stroke of 70 mm, meaning that about 3 cycles are required to cause the catheter tip to travel 200 mm. The measured position is shown in FIG. 36a and the tracking error is shown in FIG. 36b. In FIG. 36a, two lines are shown: one showing the ideal path, being the value of the distance that needs to be reached ideally, and one showing the measured path which, because of regripping error, is slightly displaced from the ideal path. A proper linear increase in position over time can be seen from these FIGS. In addition, the tracking error between the ideal path (at the desired speed=5 mm/s) and the actual traveled path shows reasonable deviation. There are no evident peaks or jumps in position when the gripping/ungripping action occurs between cycles at t=25 s (as indicated in FIG. 36a). This is due to the fact that the transition between grippers only occurs when both grippers are gripped and moving at the same speed (dynamic re-gripping). The position error at the end of the cycles was less than 0.1 mm indicating the driver's high positional accuracy.

Figures 37A, 37B, 37C:
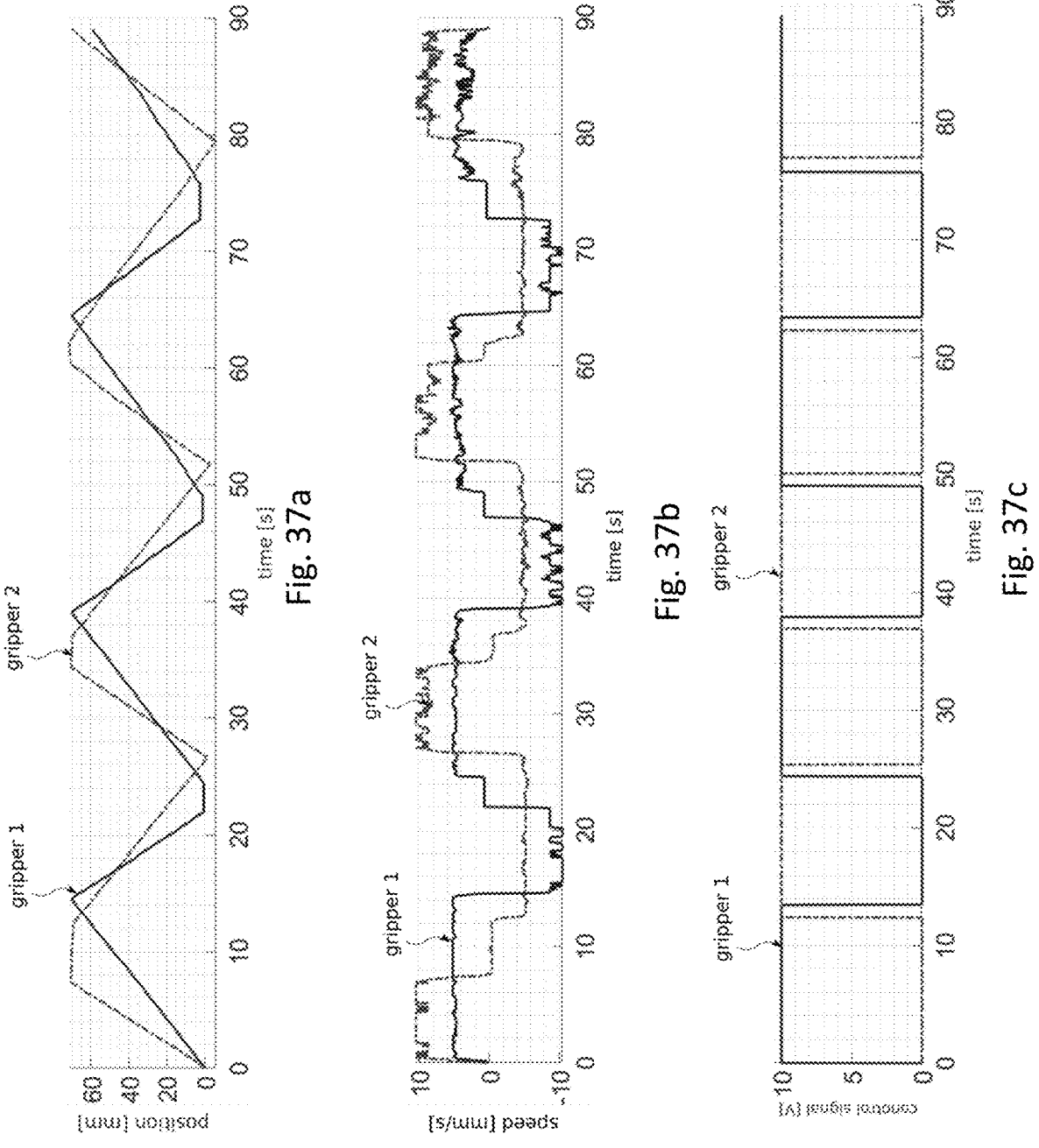
FIG. 37a is a plot of the position of first and second sleeves as a function of time, illustrating advantages of embodiments of the present invention.
FIG. 37b is a plot of the speed of first and second sleeves as a function of time, illustrating advantages of embodiments of the present invention.
FIG. 37c is a plot of corresponding electrovalve signals provided to first and second sleeves as a function of time, illustrating advantages of embodiments of the present invention.

FIG. 37a shows the position measurements of the individual grippers as measured by the encoders with respect to time. The speed of the grippers is shown in FIG. 37b. FIG. 37c shows the corresponding electrovalve control signals to indicate when the sleeves are in a gripping state. In this case, a position setpoint of 420 mm was set (this corresponds to 6 cycles), this being the position to which the catheter is to be translated assuming that the catheter starts at a position 0 mm. The experiment illustrates the behaviour of each gripper during a regripping process following the scheme of FIG. 31.

FIGS. 37a and 37b shows that a gripper in a gripping or fixed state arrives at a desired position at a later time than a gripper in an ungripped or free state. This slower speed of gripper 1 between 0 and 10 second allows the gripper to be ready for a next gripping. Indeed, the regripping is noticeable between 10 and 20 seconds (FIG. 37b). Once the gripper 2 reaches the desired velocity, the gripping is activated for gripper 2 and releasing is noticed for the gripper 1. The same pattern is reproduced by the gripper 1.

It is understood that further improvement of performance can be achieved e.g. by changing components and control strategies. The presented results can be seen as a lower bound on achievable performance.

The drive systems based on one or a combination of grippers according to embodiments of the present invention, and linear actuation systems such as the device 800 and the apparatus 900, provide a means for steering an elongate member along a direction that coincides with the longitudinal axis or at least a part of the longitudinal axis of the elongate member. By adding a second drive and transmission system configured to provide a rotational motion, it becomes possible to rotate the elongate member about its longitudinal axis as well as to translate it along that longitudinal axis.

Figure 39:
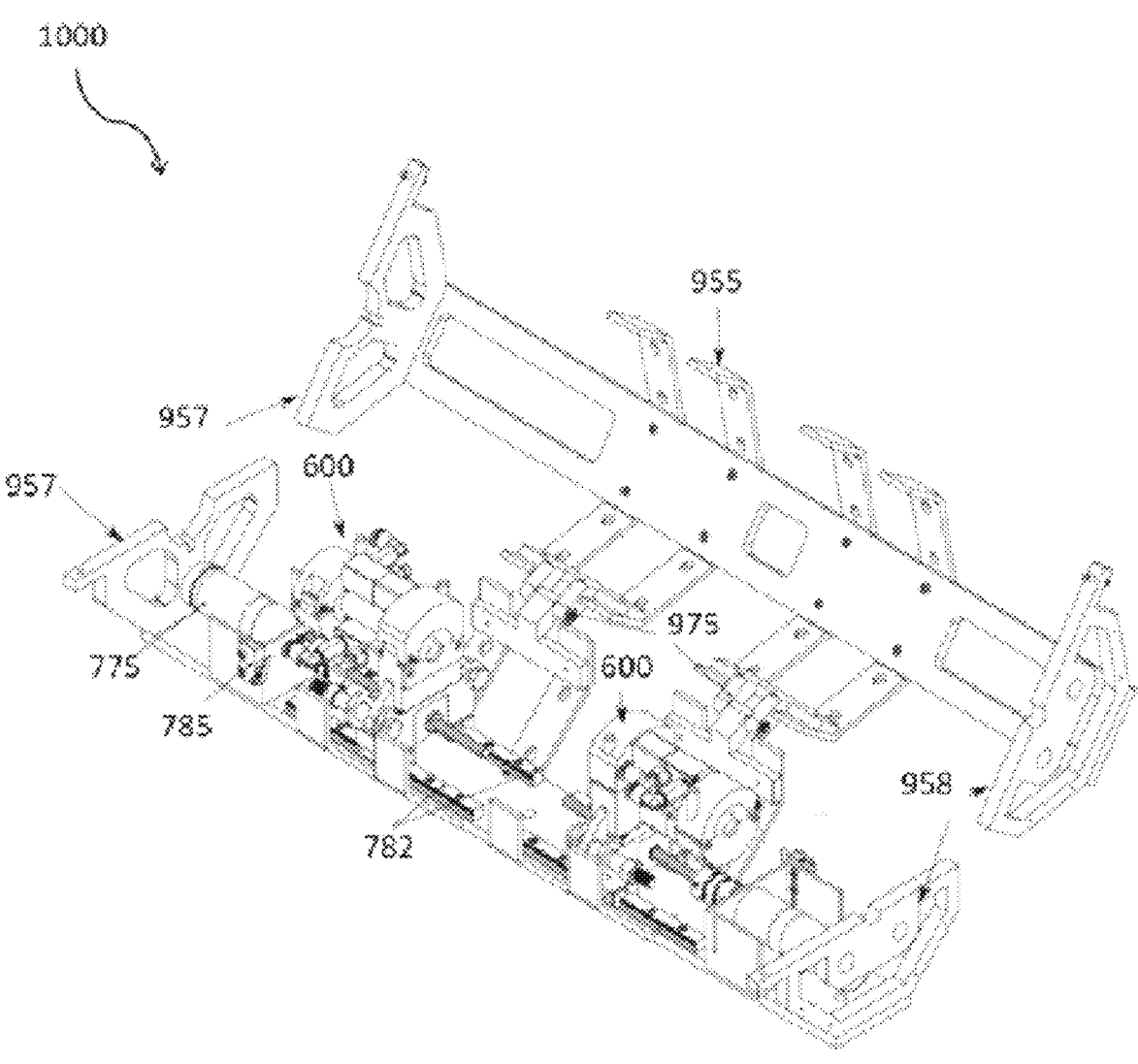
FIG. 39 is a perspective view of apparatus according to embodiments of the present invention in an open configuration wherein grippers comprised in the apparatus are in a closed configuration.
Figure 40:
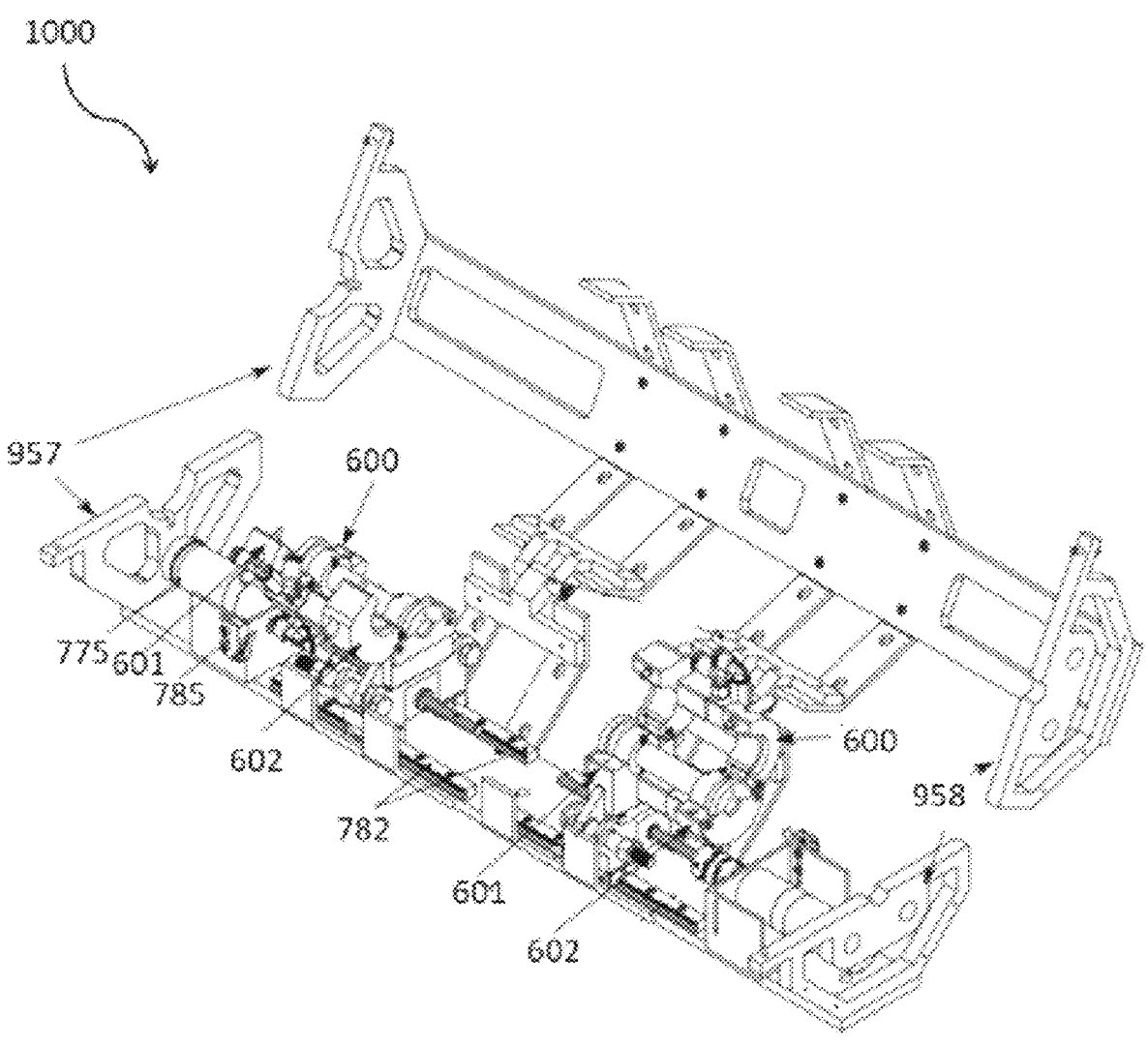
FIG. 40 is a perspective view of apparatus according to embodiments of the present invention in an open configuration wherein grippers comprised in the apparatus are in an open configuration.

Referring to FIGS. 38 to 40, apparatus 1000 according to embodiments of the present invention comprises apparatus 900 as described previously in relation to FIG. 30 and an axisymmetric frame 950. The frame 950, also shown in FIGS. 39 and 40, comprises a first section 951 and a second section 961. The first section 951 comprises a longitudinally extending portion 952 having a first, or proximal, end 953 and a second, or distal, end 954. The first section 951 comprises rib portions 955 arranged between the first and second ends 953, 954 and extending from each side of the longitudinal portion 952.

The first section 951 comprises a first end portion 957 at the first end 953 and a second end portion 958 at the second end 954 which each take the form of a half-octagon cut so as to bisect two opposite sides of the octagon. The first end portion 957 comprises a semi-circular cutout 959 at the midpoint of its long edge. The second end portion 958 comprises a semi-circular cutout 960 at the midpoint of its long edge.

The second section 961 comprises a longitudinally extending portion 962 having a first, or proximal, end 963 and a second, or distal, end 964. The second section 961 comprises rib portions 965 arranged between the first and second ends 963, 964 and extending from each side of the longitudinal portion 962.

The second section 961 comprises a first end portion 967 at the first end 963 and a second end portion 968 at the second end 964 which each take the form of a half-octagon cut so as to bisect two opposite sides of the octagon. The first end portion 967 comprises a semi-circular cutout 969 at the midpoint of its long edge. The second end portion 968 comprises a semi-circular cutout 970 at the midpoint of its long edge.

Figure 41:
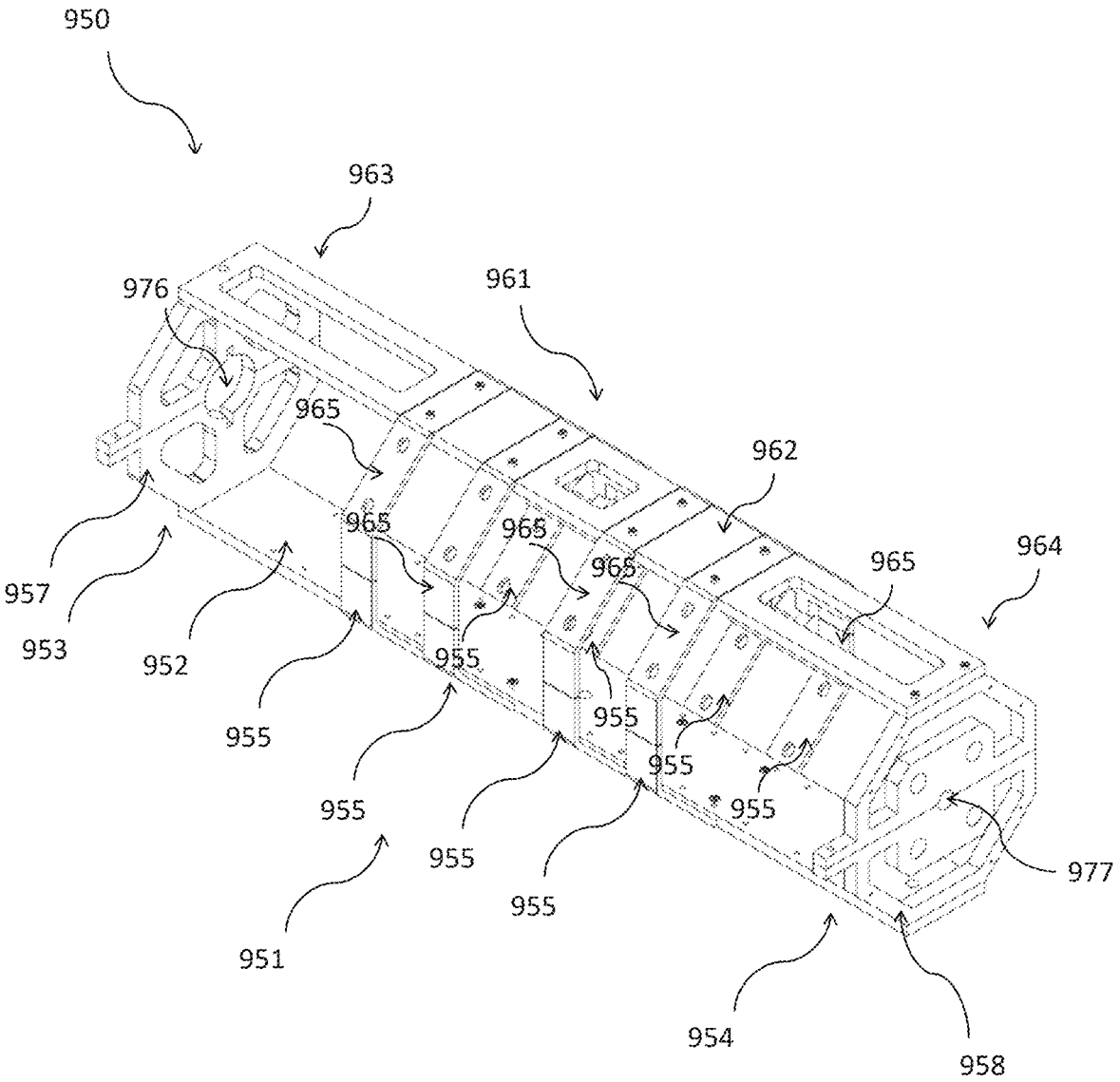
FIG. 41 is a perspective view of a frame comprised in apparatus according to embodiments of the present invention in a closed configuration.
Figure 42:
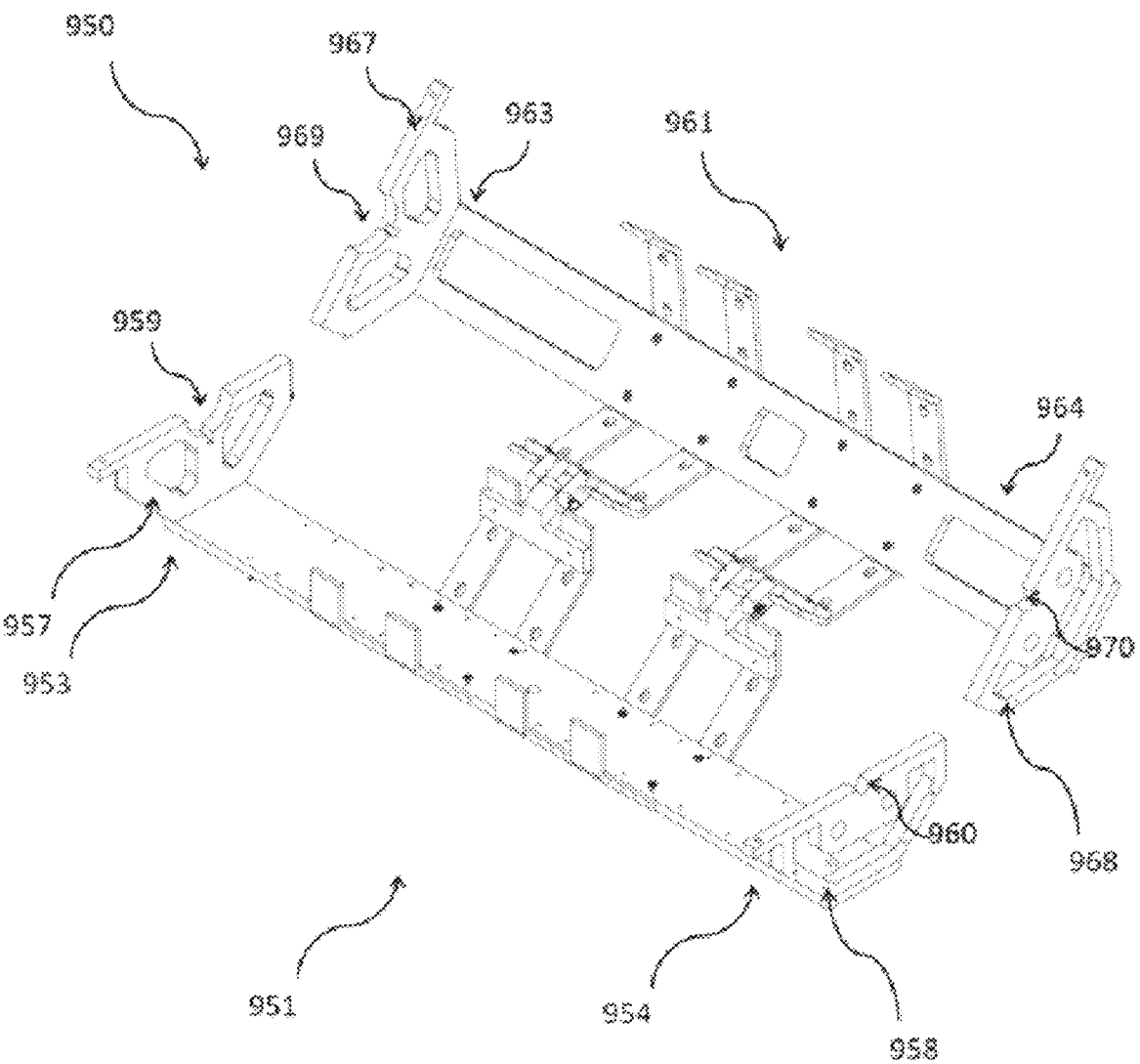
FIG. 42 is a perspective view of a frame comprised in apparatus according to embodiments of the present invention in an open configuration.

The rib portions 955 along one side of the first section 951 are coupled to the rib portions 965 along one side of the second section 961 by hinge connections 975. The first section 951 and the second section 961 can thus be placed in an open configuration (FIG. 42) and a closed open configuration (FIG. 41). In the closed configuration the end portions of the first and second sections cooperate so as to form a first circular aperture 976 at the first end and a second circular aperture 977 at the second end. The first and second circular apertures in the closed configuration are aligned with the axes of the grippers (FIG. 38).

Apparatus 900 can be arranged in the frame 950 for example by bolting the base plate 778 to the first section 951. The frame 950 can be fixed in a closed configuration by tightening thumb screws 979 configured to couple end portion 957 to end portion 967, and end portion 958 to end portion 968.

The end portions 957, 958, 967, 968 may comprise one or more additional holes or slots which can have one or more functions such as cable or tubing routing and weight reduction.

Referring to FIG. 40, the apparatus 1000 is shown with the grippers in an open configuration. This allows an elongate member to be introduced to the apparatus 1000 from the side, that is, not along the gripper axis. For example, an operator can access first and second clamping elements of a gripper, open them, and insert the elongate member together with the sleeves that are preferably already slid over the elongate member.

Figure 43:
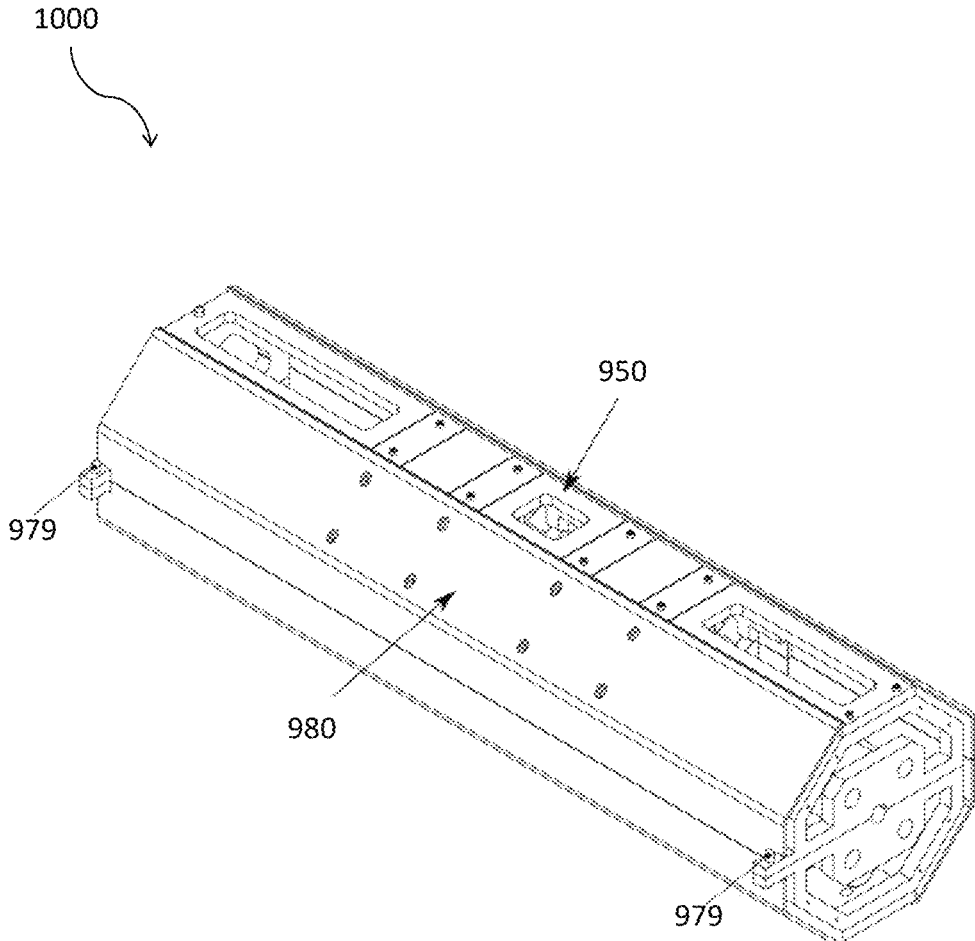
FIG. 43 is a perspective view of a frame comprised in apparatus according to embodiments of the present invention in a closed configuration and comprising cover portions.

Referring to FIG. 43, the apparatus 1000 may comprise a cover 980 that is connected to the frame 950 to protect the apparatus 900.

By rotating the entire apparatus 1000 about its longitudinal axis also any elongate member that is clamped by one or more sleeve-based grippers comprised in the apparatus 900 would rotate about its axis. Different mechanisms to rotate the apparatus 1000 can be envisioned.

Mechanisms could be based on a structure like a cradle where the apparatus 1000 is hinged and supported at both sides and a drive system that is mounted on the cradle-base is used to rock or more specifically rotate the apparatus in the cradle. This approach provides a stable support for the cage, but may lead to larger structures and may also restrict somehow the range-of-motion as it may be more difficult to allow large and multiple revolutions.

Figure 44:
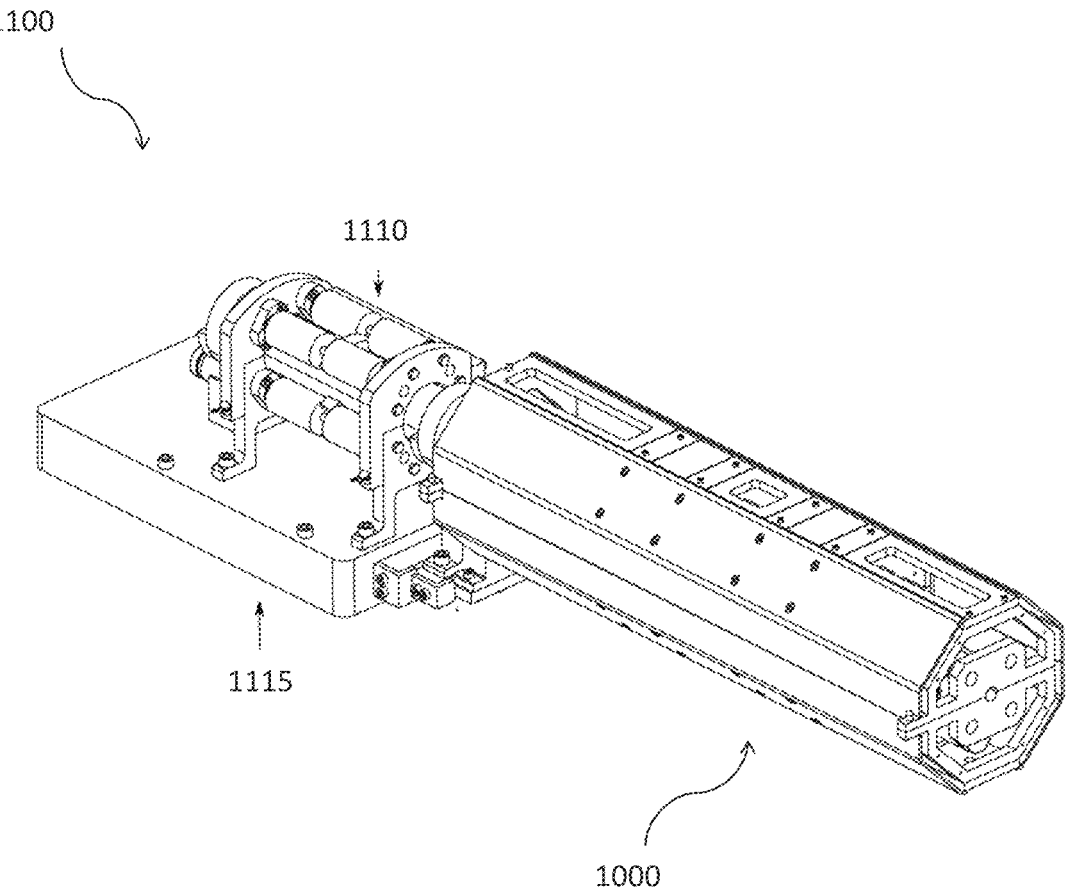
FIG. 44 is a perspective view of a combined drive system according to embodiments of the present invention.

Mechanisms could also have only a support at a single side, a preferred embodiment of which is shown in FIG. 44. FIG. 44 shows a combined drive system 1100 comprising apparatus 1000 which is clamped into a rotary module 1110 which is mounted to a base plate 1115.

The axis of rotation of the rotary module 1110 is co-axial with the axis of rotation of the drive system, such as the spindle drive 770, that is responsible for the linear actuation of the apparatus 1000. The linear module 1000 is connected with the drive shaft to the rotary module 1110.

The combined drive system 1100 is thus capable of both translation and rotation of an elongate member held in grippers comprised in the apparatus 900.

Figure 45:
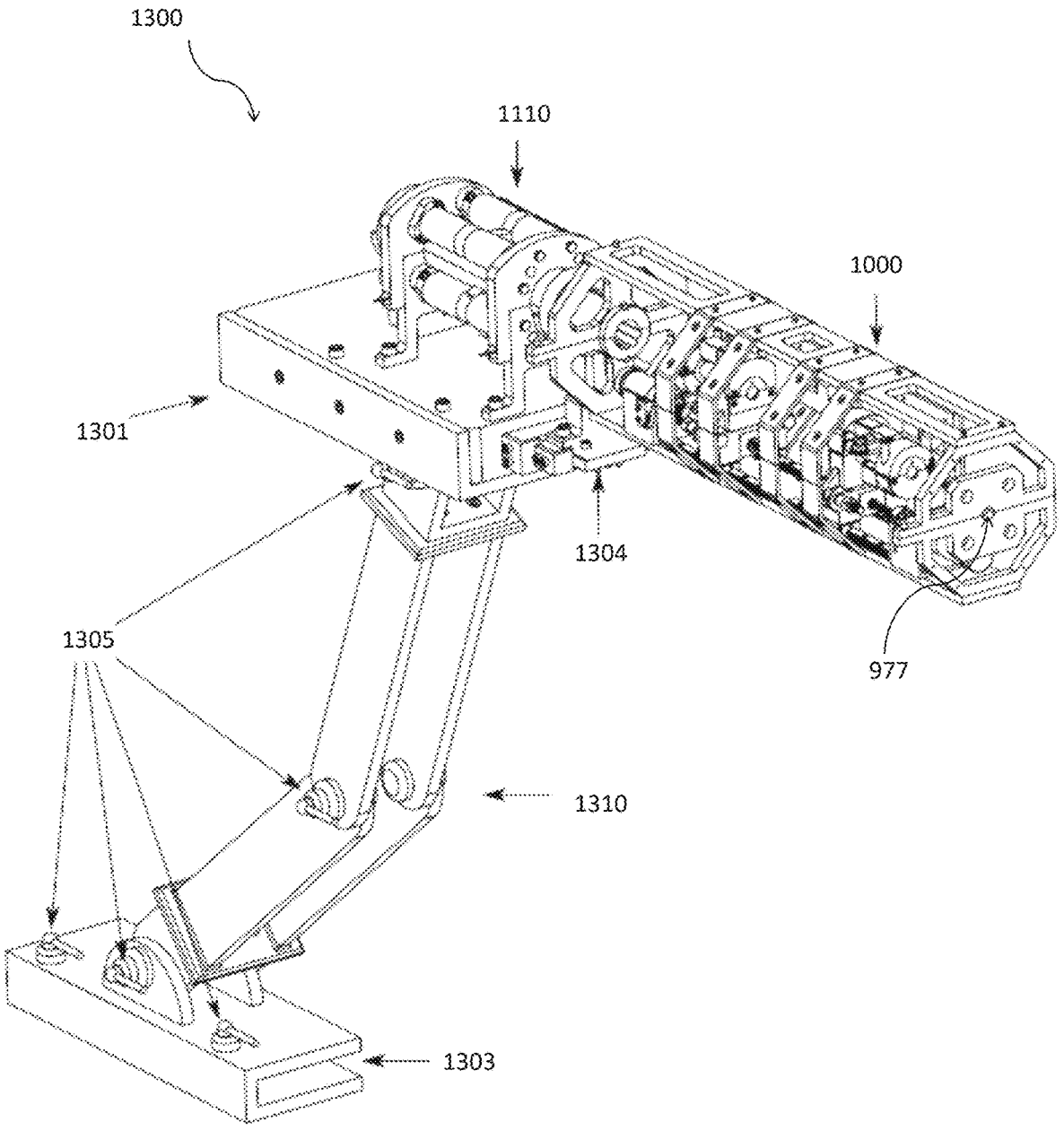
FIG. 45 is a perspective view of a composite apparatus according to embodiments of the present invention.

Referring to FIG. 45, a composite apparatus 1300 comprises the combined drive system 1100 mounted on a mechanical or a robotic arm 1310 which can allow positioning and maintaining the position of the drive system with respect to a patient.

The composite apparatus 1300 comprises a base plate 1301 mounted on the mechanical or robotic clamping arm 1310. The arm 1310 can be clamped to an operating table (not shown) using an operating table clamp 1303 at the opposite end of the arm 1310 to the base plate 1301. The base plate 1301 supports the combined drive system 1100.

The position and inclination of the drive system 1100 relative to the operating table, and the fixation of the arm 1310 to the operating table, is done by tightening a plurality of clamping screws 1305 at hinge points in the arm 1310 and on the table clamp 1303. Different kind of screws or fixation mechanisms may be used including mechanisms that are pneumatically, hydraulically locked or that are locked by other means and that can fix one or multiple screws or locations at the same time.

Preferably the mechanical or robotic arm 1310 can be positioned easily, swiftly, robustly and accurately so that users can safely and easily bring the structure in an optimal configuration for operation. For example in the case of catheter-based operation this would mean that the operator can easily align the exit of the system, for example the aperture 977, with the incision into the patient.

In some embodiments it may be desired to align the drive system 1100 prior to intervention and then to introduce an elongate member to the drive system 1100. In the preferred embodiment of FIG. 45 and if placement or exchanges needs to be fast and smooth this means that it is necessary to open up both the rotary module 1110 and the translational actuation apparatus 1000 to place the elongate member.

Insertion of the elongate member along the shared longitudinal axis of the rotary module 1110 and translational actuation apparatus 1000 can be considered if it is impossible or impractical to open either of the rotary module 1110 or the translational apparatus 1000, but this may be a difficult process especially if the elongate member is somewhat deformable and tolerances are tight.

A preferred embodiment of the present invention allows opening both the rotary module 1110 and translational actuation apparatus 1000. However, in order to safely and reliably open either of both structures an additional support structure may be needed to stabilize and support these components when opened. The composite apparatus 1300 of FIG. 45 includes a telescopic support arm 1304 integrated in the base plate 1301 which can be extracted and fixed to translational actuation apparatus 1000 to support the latter when inserting, exchanging or extracting an elongate member. Other support means are possible.

Referring to FIGS. 46 to 49, a rotary module 1110 is shown in more detail.

Figure 46:
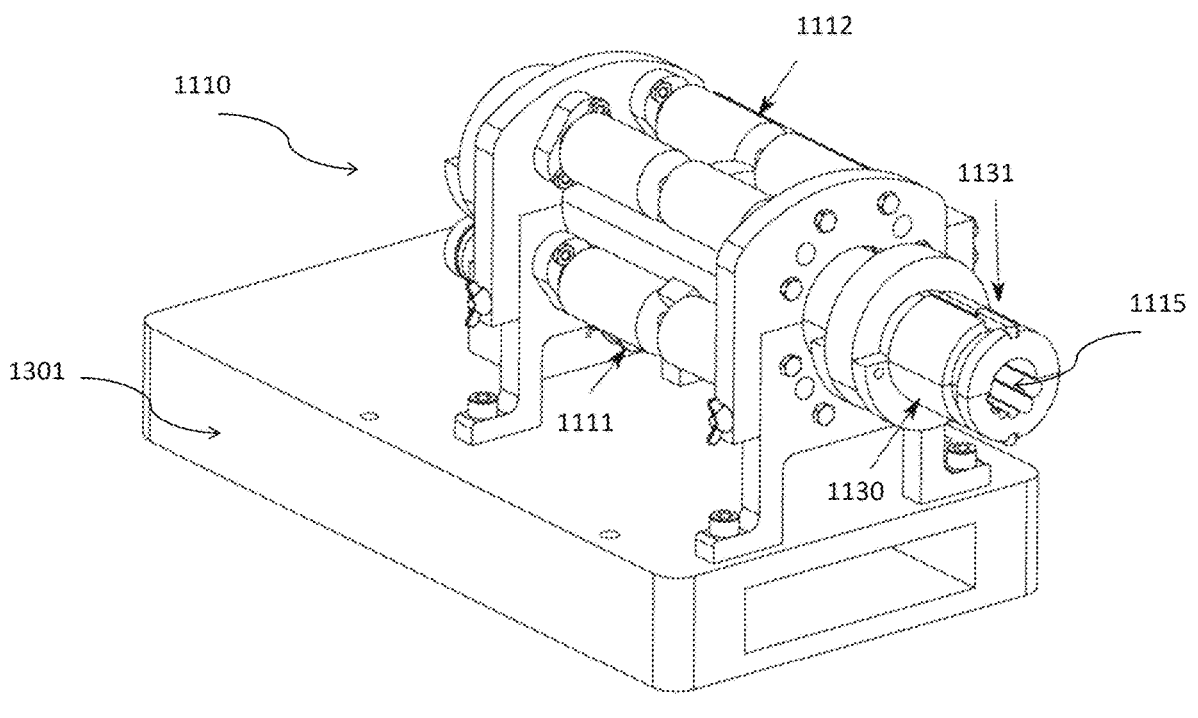
FIG. 46 is a perspective view of a rotary drive module which may be comprised in systems or apparatus according to embodiments of the present invention.

The rotary module 1110 comprises a first frame 1111 and a second frame 1112. The first frame is configured to be fixed to the base plate 1301 of the composite apparatus 1300. The second frame 1112 is connected to the first frame 1111 through a pair of hinges 1113. The hinges 1113 allow the rotary module to be moved between an open state (FIGS. 48 and 49) and a closed state (FIG. 46).

In the closed state an aperture 1115 is provided between the first frame 1111 and the second frame 1112 through which an elongate member can pass.

The first frame 1111 carries a set of four rollers 1115 mounted on two axes 1116 and the second frame 1112 carries a set of four rollers 1117 mounted on two axes 1118. Each axis is supported by a pair of bearings 1119 that are fixed at the sides of the frames 1111 and 1112. One pair of axes is connected via a timing-belt 1119 and pulley 1123 to the outgoing axis of a motor-reductor combination 1120 which is supported by a housing 1121 fixed to the base plate 1301.

By loosening a pair of knurled thumb screws 1122 the frame can be opened.

Figure 50:
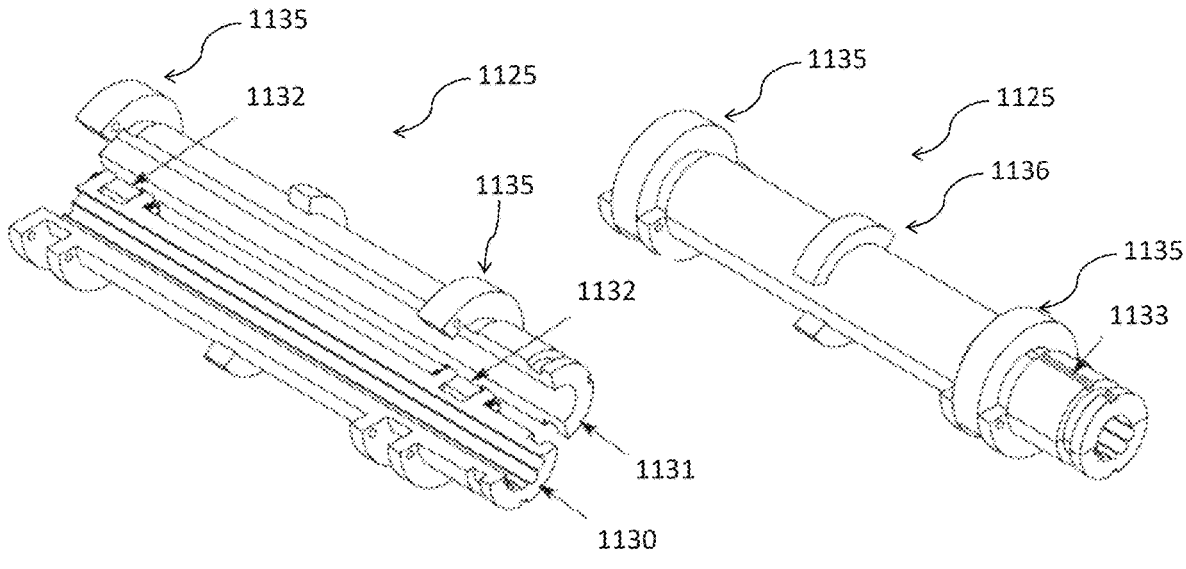
FIG. 50 is a perspective view of a rotary drive shaft which may be comprised in a rotary drive module, as can be used in an embodiment of the present invention.

The rotary module 1110 comprises a drive shaft or rotary shaft 1125 which can be mounted between the sets of rollers. Referring to FIG. 50, the drive shaft 1125 is shown for connecting a rotary module 1110 to translation actuation apparatus 1000. The rotary shaft 1125 is configured to pass through the center of the rotational module 1110 up to the first end portions 957, 967 of the frame 950 of the translational actuation apparatus 1000.

Figure 49:
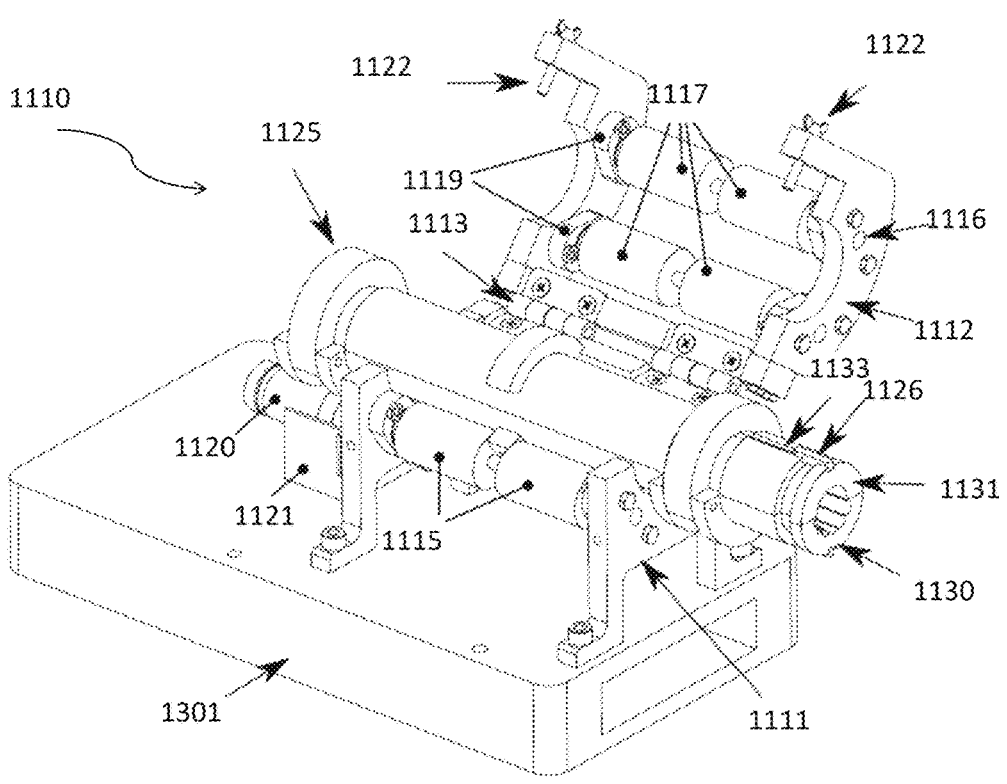
FIG. 49 is a perspective view of the rotary drive module of FIG. 46 in an open configuration with a rotary drive shaft.

The hollow rotary shaft 1125 has two grooves or key seats 1133 along its outer surface in longitudinal direction for receiving a pair of alignment keys 1126 (FIG. 49). A radial slot at the distal extremity of the hollow shaft 1125 is of the same thickness as the first end portions 957, 967 which are configured to fit in this slot. This fit ensures that when the frame 950 is in a closed configuration, the hollow rotary shaft is locked in a longitudinal direction with respect to the frame 950. The pair of keys 1126, key seats 1133 and key ways in respectively the hollow shaft 1125 and the aperture 977 in the apparatus 1000 ensure that there is minimal relative rotational motion possible between the shaft and the frame 950 such that when the shaft 1125 spins or rotates about its axis also the frame 950 will spin or rotate about its longitudinal axis.

Figure 51:
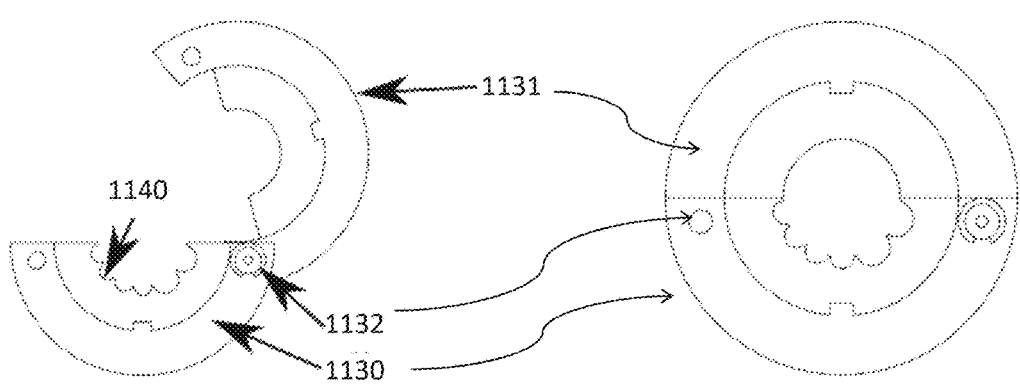
FIG. 51 is a cross-sectional view of a rotary drive shaft which may be comprised in a rotary drive module showing cable routing cutouts, as can be used in an embodiment of the present invention.

The rotary shaft 1125 is hollow as it allows an elongate member to pass through. The rotary shaft 1125 may also allow electronic signal cables, pneumatic supply or other power lines necessary for operating actuators and sensors of the apparatus 1000 to pass through. Referring to FIG. 51, in one preferred embodiment of the shaft 1125 a series of longitudinal slots 1140 are provided in the inner wall of the hollow shaft 1125 to route all 'permanent' cables (sensor, electronic signal and power), whereas space is left in the centre of the hollow shaft to pass the elongate member.

The rotary shaft 1125 preferably comprises a plurality of components, that is, is not formed of a single piece, such that the shaft 1125 itself can be opened and closed along its longitudinal axis. This property makes it possible to introduce or extract an elongate member from the side.

Referring to FIG. 50, the rotary drive shaft 1125 preferably comprises two half shafts 1130, 1131, which are connected by a pair of hinges 1132. At the distal end a pair of key seatings 1133 are prepared for aligning via a pair of keys 107 1126 to the apparatus 1000.

Each half shaft 1130, 1131 comprises a collar 1135 at each end of the shaft part. This collar can constrain the drive shaft 1125 and the parts connected to it in axial direction such that there is no relative displacement of the frame 950 with respect to the base plate 1301 in the longitudinal direction. The shaft 1125 also comprises a central collar 1136 located between the end collars 1135.

The shaft 1125 may comprise a proximal clamp 1137 and a distal clamp 1138 to open and close the rotational drive shaft 1125. The rotational drive shaft 1125 can be inserted in a rotational drive unit 1110 when the drive unit 1110 is in an open configuration.

Referring again to FIGS. 46 and 49, by closing the frame and tightening the knurled thumb screws 1122 the drive shaft 1125 is constrained by the set of rollers 1115, 1117, which may be made from a material with relatively large static friction coefficient. When the rollers 1115, 1117 are actuated then due to friction the drive shaft 1125 will also start to rotate typically at the same speed.

Figure 47:
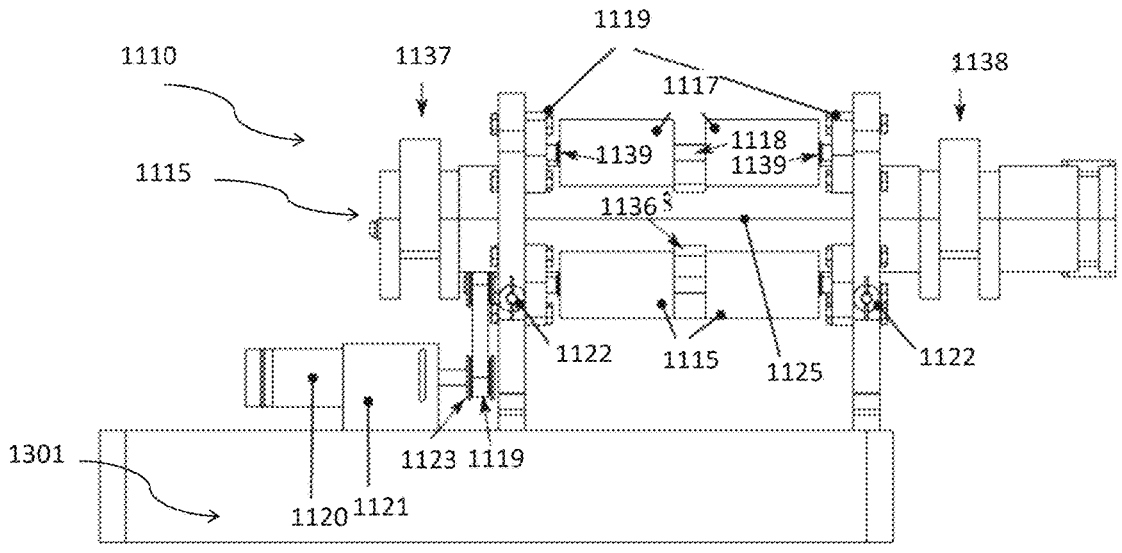
FIG. 47 is a cross-sectional side view of the rotary drive module of FIG. 46.
Figure 48:
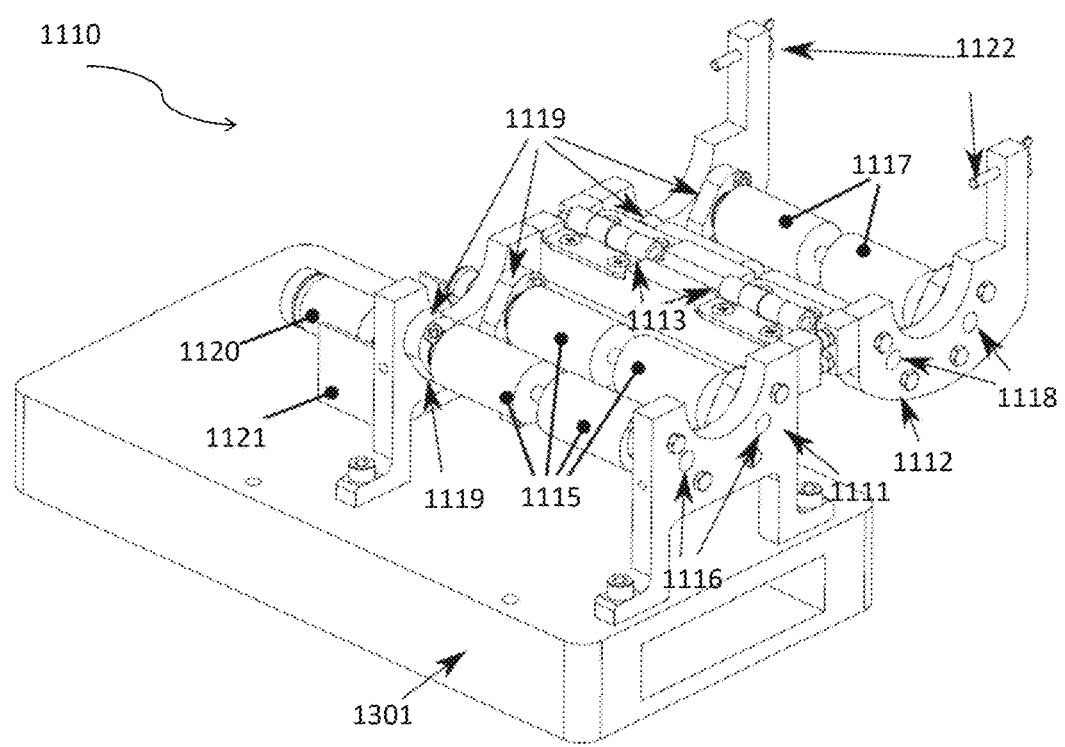
FIG. 48 is a perspective view of the rotary drive module of FIG. 46 in an open configuration without a rotary drive shaft.

Referring to FIG. 47, from the side view it can be seen how the central collar 1136 of the rotary drive shaft 1125 is positioned tightly between proximal and distal sets of rollers 1115, 1117. The position of the rollers themselves is axially constrained by a number of circlips 1139. This allows the rotary shaft 1125 to be prevented from moving axially as the rollers are prevented from moving axially.

One advantage of this configuration is that it prevents the apparatus 1000 from sliding out of the rotary module 1110 if the rotary module were to be positioned at an inclination with respect to the horizontal plane.

The displacement caused by the rotary motor 1120 is passed through the different rollers 1115, 1117 and the alignment key 1126 towards the translational apparatus 1000 that will reorient accordingly.

Referring again to FIG. 45, a telescopic support arm 1304 integrated into the base plate 1301 can be extracted and fixed to translational actuation apparatus 1000 to support the latter when inserting, exchanging or extracting an elongate member.

Figure 52A:
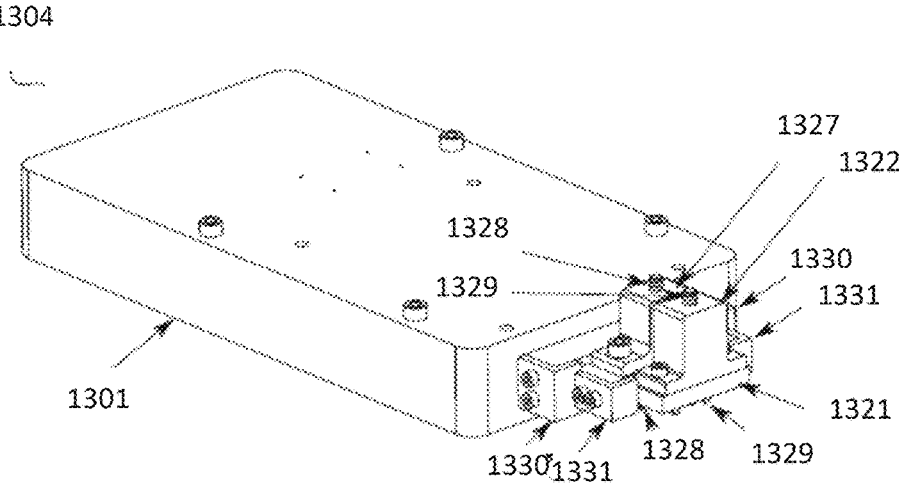
FIG. 52a is a perspective view of a support arm which may be comprised in systems or apparatus according to embodiments of the present invention, in a closed configuration.
Figure 52B:
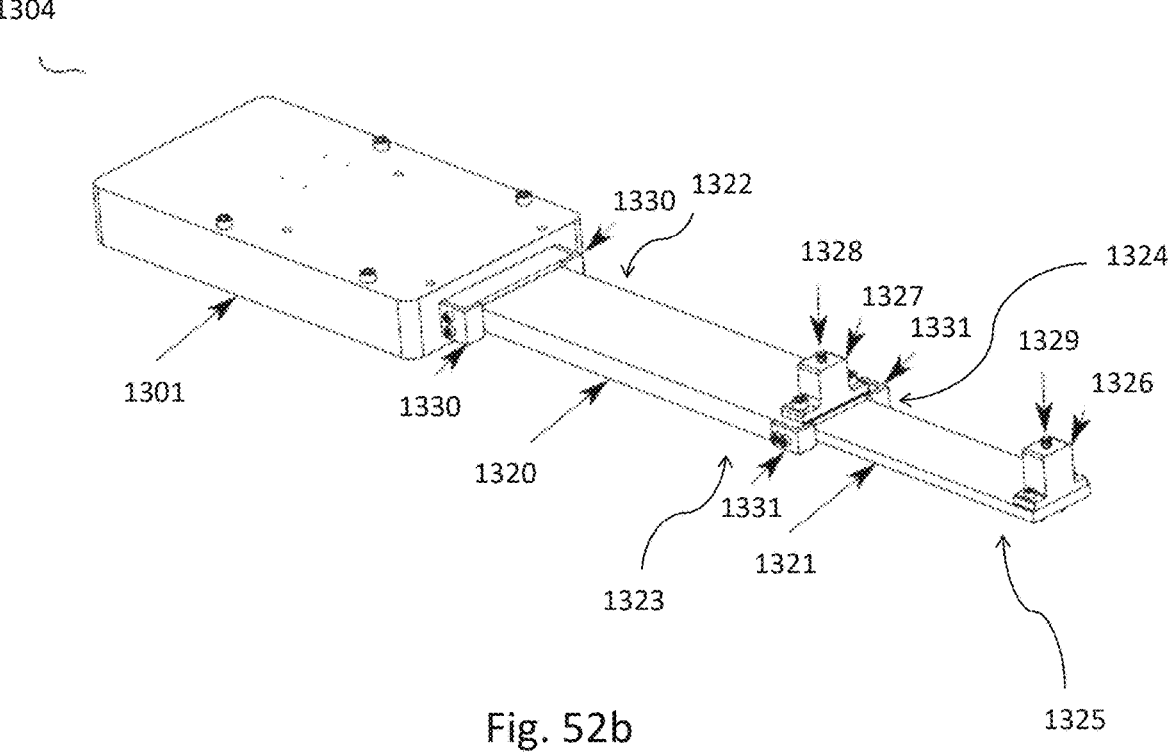
FIG. 52b is a perspective view of a support arm which may be comprised in systems or apparatus according to embodiments of the present invention, in an open configuration.

The support arm 1304 can have a closed (FIG. 52a) and an open (FIG. 52b) configuration. The support arm 1304 comprises a first telescopic arm 1320 and a second telescopic arm 1321 nested within the first telescopic arm 1320, such that in a fully extended configuration (FIG. 52b), the first telescopic arm 1320 provides a first extension relative to the base plate 1301 and the second telescopic arm 1321 provides a second extension relative to the first telescopic arm 1320. In the closed configuration (FIG. 52a), the first and second arms 1320, 1321 are in a retracted state.

The first arm 1320 has a first end 1322 and a second, opposite end 1323. In the extended state the first end 1322 is closer to the base plate 1301 than the second end 1323. The second arm 1321 has a first end 1324 and a second, opposite end 1325. In the extended state the first end 1324 is closer to the base plate 1301 than the second end 1325. In the retracted state the second end 1323 of the first arm 1320 is adjacent to the second end 1325 of the second arm 1321.

The support arm 1304 comprises a first connecting block 1326 at the second end 1323 of the first arm 1320 and a second connecting block 1327 at the second end 1325 of the second arm 1321.

Figure 53:
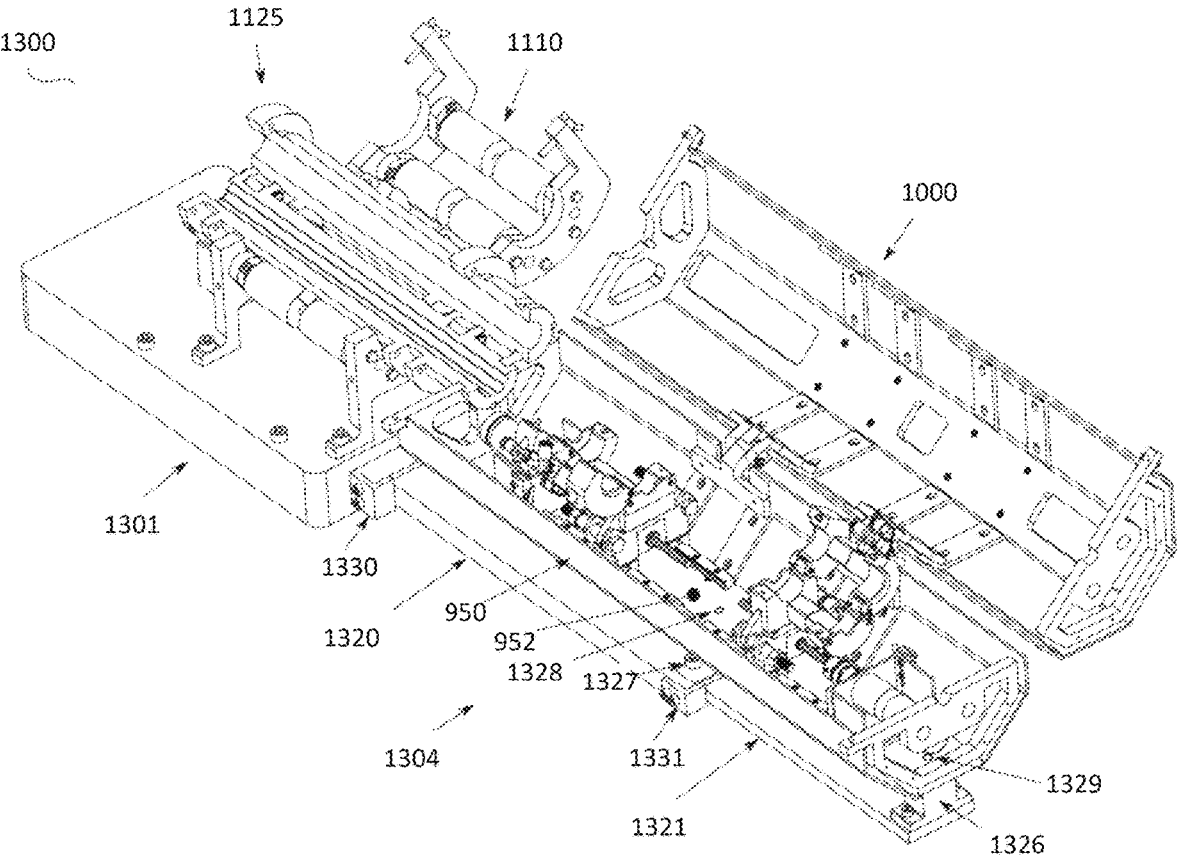
FIG. 53 is a perspective view of apparatus comprising a support arm and a system according to embodiments of the present invention in an open configuration coupled to the support arm with the support arm in an extended state.
Figure 54:
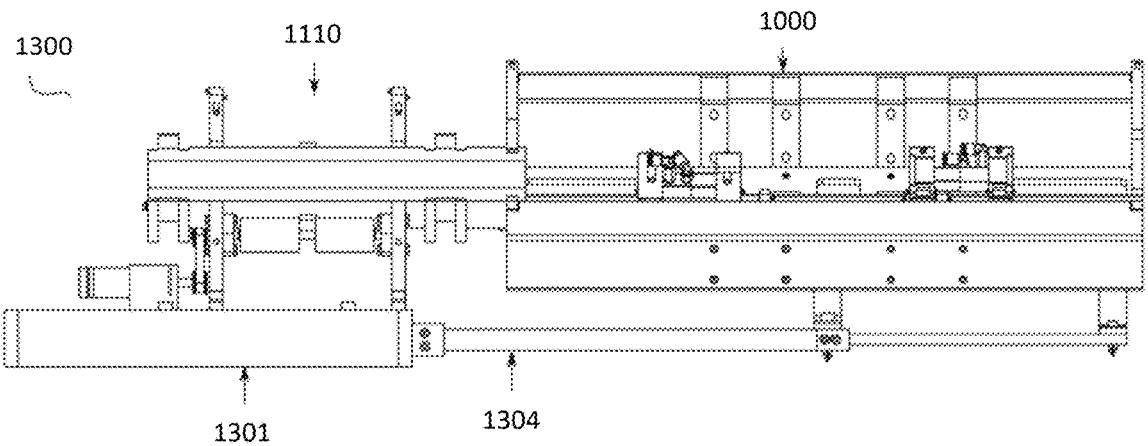
FIG. 54 is a cross-sectional side view of FIG. 53.

Referring to FIGS. 53 and 54, the support arm 1304 provides means for supporting the apparatus 1000, for example when the apparatus 1000 is in an open configuration for accessing internal parts of the apparatus 1000 and/or when the rotary module 1110 is in an open configuration. For example, the support arm 1304 may be placed in an extended configuration for supporting the apparatus 1000 during insertion, exchange, or removal of an elongate member into the apparatus 1000 and/or the rotary module 1110. During manipulation of the elongate member by the apparatus 1000 and/or the rotary module 1110 the support arm 1304 is retracted.

The support arm 1304 preferably comprises a first fixation screw 1328 at the first connecting block 1326 and configured to couple the first arm 1320 via the first connection block 1326 to the longitudinal portion, or base plate, 952 of the apparatus 1000. The support arm 1304 preferably comprises a second fixation screw 1329 at the second connecting block 1327 and configured to couple the second arm 1321 via the second connection block 1327 to the longitudinal portion, or base plate, 952 of the frame 950 comprised in apparatus 1000.

The support arm 1304 preferably comprises a first set of restraining corners 1330 arranged on the base plate 1301 and a second set of restraining corners 1331 arranged at the second end 1323 of the first arm 1320. The restraining corners 1330, 1331 are configured to guide the extension of the support arm 1304 and to prevent the first arm 1320 and second arm 1321 from dislocating. Embodiments of the present invention provide configurations for routing one or more cables or tubes, for example for supply to pneumatic and electromagnetic actuators or for sending control signals or for receiving signals from one or more sensors.

Figure 55:
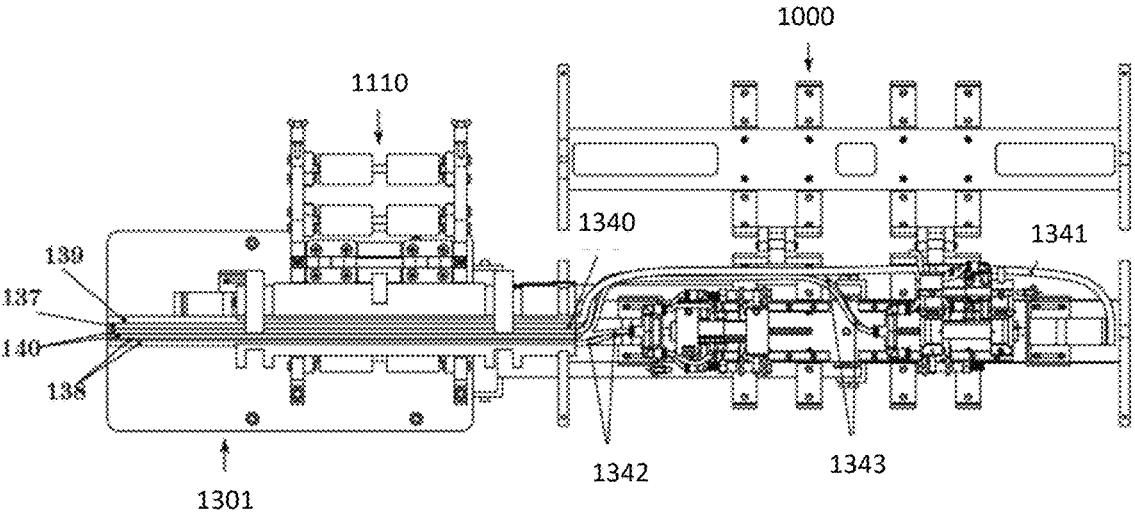
FIG. 55 is a cross-sectional side view of a cable routing configuration for the apparatus of FIG. 53.
Figure 56:
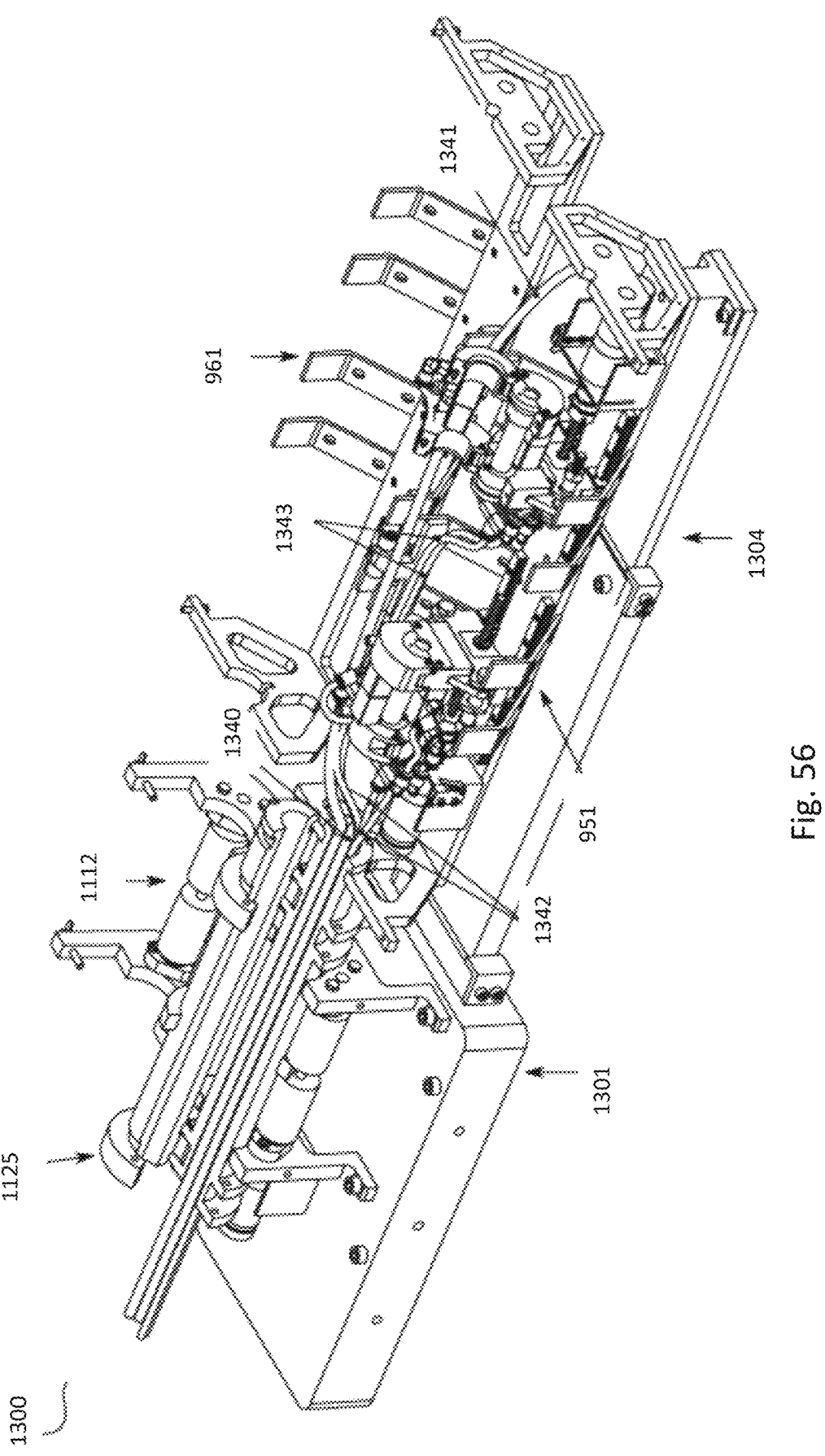
FIG. 56 is a perspective view of a cable routing configuration for the apparatus of FIG. 53 in an open configuration.

Referring to FIGS. 55 and 56, one example of routing of power cables, signal cables, supply and exhaust tubes for the system depicted in FIG. 53 is shown.

The system 1300 comprises motor cables 1340, 1341 and air supply tubes 1342, 1343. The motor cables 1340, 1341 and air supply tubes 1342, 1343 are routed around the system 1300 through machined slots 1140 (FIG. 51) of the fixed rotary shaft 1125 within the rotary module 1110.

This kind of routing where the cables and tubes are routed along the longitudinal axis of the system can be advantageous because upon rotation of the rotary module these cables will only twist about their own axis with little interference with surrounding components. The rotary module 1110 can then rotate over large angular ranges of up to 360 degrees or even more.

Referring to the top view shown in FIG. 56, the proximal motor cable 134 and air supply tubes 133 can be directly passed through the machined slots 174 of the fixed rotary shaft 1125 within the rotary module 1110. The distal motor cable 136 and air supply tubes 135 are pre-bent and curved towards the side of the frame 950 before being passed through the machined slots 174 of the fixed rotary shaft 1125 within the rotary module 1110. The cables 134, 136 and tubes 133, 135 contact the first part 1130 of the rotary shaft 1125 only. The upper part 1131 of the rotary shaft 1125 is free allowing for easy insertion of an elongate member. This also simplifies the creation of a sterile barrier e.g. through use of an elongated sterile arrangement as will described hereinafter.

Figure 57:
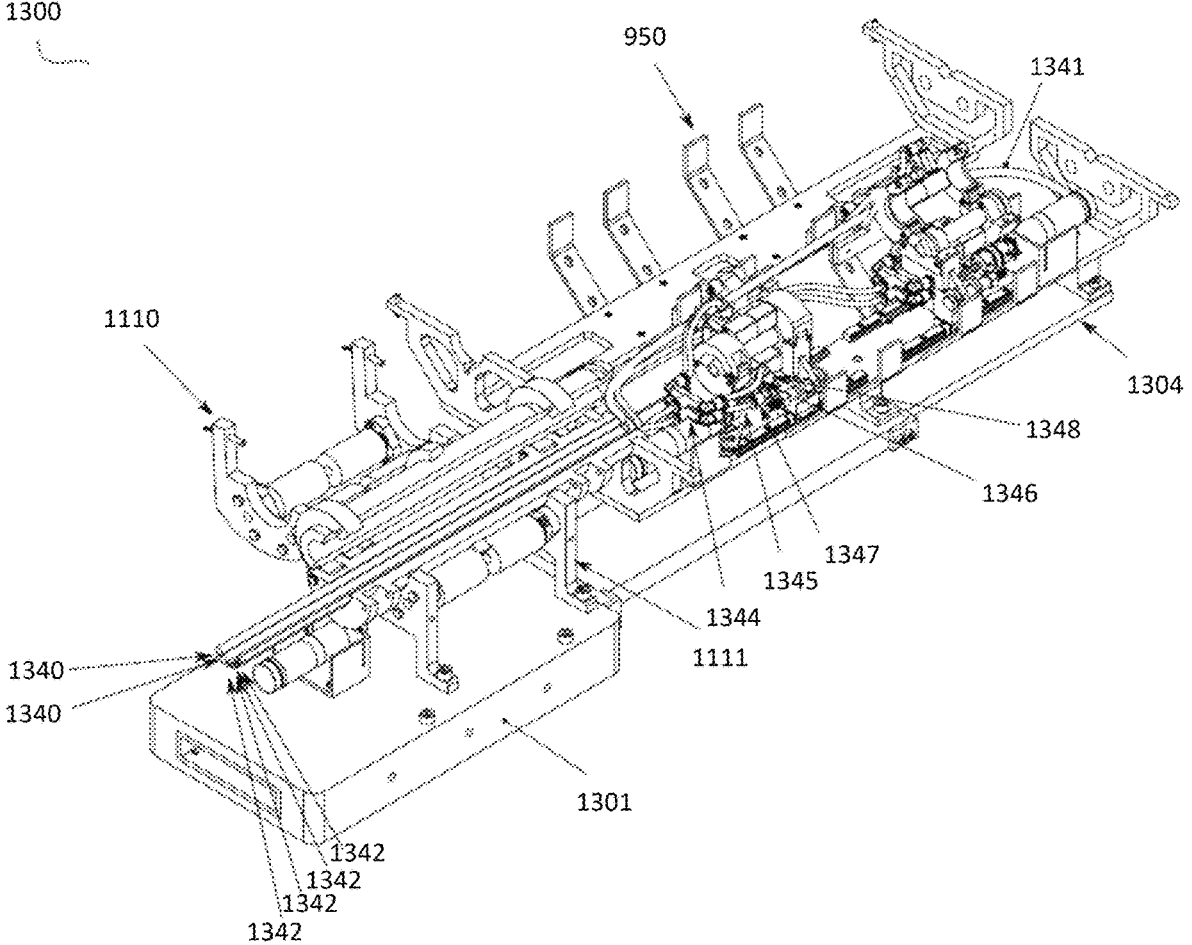
FIG. 57 is a perspective view of a system according to embodiments of the present invention.

Referring to the isometric view of the system 1300 shown in FIG. 57, as seen from the proximal side, in a preferred embodiment the grippers are double-acting, but also single-acting pistons that act against a return-spring can be envisioned. In case of double-acting grippers two supply/exhaust lines are needed for acting fast (approximately equally fast) in both directions. Further each gripper 600 comprises two pistons positioned in a parallel layout.

In order to prevent the grippers from jamming, e.g. due to non-synchronized motion, in an preferred embodiment of the invention, both pistons are fed by one single supply-line. A t-shaped connector 1344 is then used to connect two intermediate tubes 1345 and 1346 from the common supply/exhaust line to the individual inputs 1347 and 1348. This can help to ensure that that both sides of the pistons move synchronously in or out.

The proposed invention is of particular use to drive a broad range of elongate members.

Embodiments of the present invention are capable of manipulating specific elongate members which could be rigid with a constant cross-section, rigid with a variable cross-section over the length of the elongate member, flexible with a constant cross-section over the length of the elongate member or flexible with a variable cross-section over the length of the elongate member.

Variations in cross-sections of elongate member are preferably, but not necessary, gradual and smooth over the length of the elongate member. Variations in cross-sections may be step-wise, and the elongate member can be considered as a concatenation of elongate members. Elongate members with step-wise variations at some and smooth variations at other parts of the elongate member are also capable of being manipulated according to embodiments of the present invention.

Some elongate members may be driven over their entire length. Other elongate members may be driven only over a certain length and only over some specific parts of their length.

Elongate members may be manipulated for which the cross-section varies over time. Such variation could be geometrically where over the entire length or over specific regions the elongate member shrinks in size or where it expands or dilates.

An elongate member having a variation in stiffness over a part or all of its length can be manipulated according to embodiments of the present invention, for example a rise in stiffness becoming more rigid or a reduction of stiffness becoming less rigid.

Variations in stiffness could be caused for example wherein the elongate member comprises a smart material, for which the crystalline structure alters upon applying a charge input, such in piezoelectric materials, or upon applying a magnetic field, heat or changing other properties of the elongate member. The variation could be caused for example also by adjusting the pressure in an internal channel that runs through the elongate such as in the case of granular jamming.

Cross-sectional properties of an elongate member and variations thereof may change in time, for example one or more sections may grow larger in length or shift in position, for example by sliding over inner or outer structures of the elongate member. A cable or bar may run through the elongate member or parts of it, wherein when displacement of this cable or bar takes place over a certain length of the cable or bar, the effect may be effectively to change the cross-sectional shape at some specific localised or distributed regions of the elongate member.

Figure 58:
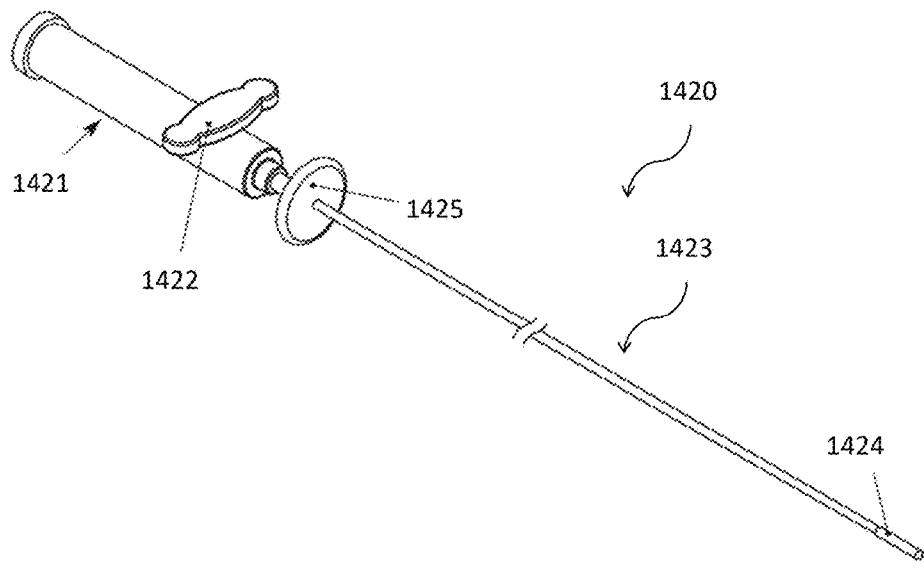
FIG. 58 is a perspective view of a catheter as an example of an elongate member capable of manipulation by grippers, devices, systems or apparatus according to embodiments of the present invention.

Examples of such structure would be for example endoscopes or catheters with distal dexterity, where parts of the distal structure are capable of contracting, elongating, twisting or bending or any combination thereof upon, for example, changes that are initiated proximally for example, but not limited to, pushing or pulling of a handle 101 (FIG. 9) or operation of a lever (FIG. 58).

Some embodiments of the present invention are capable of manipulating a broad range of such elongate members. Some embodiments of the present invention may be tailored to a specific type of elongate member. For the purpose of providing an example and without loss of generality an example is given of how the present invention and an embodiment thereof can be used advantageously to drive an elongate member comprising a catheter with a flexible bendable tip.

Referring to FIG. 58, a catheter 1420 capable of manipulation according to embodiments of the present invention comprises a handle 1421 that may be used held manually by an operator or clinician or handled by a mechanism such as a distal tip driving element 1640 as will be described hereinafter and a bending lever 1422 to be used manually by an operator or a clinician or by an actuation system such as shown in FIG. 57. The bending lever 1422 is supported by the handle 1421. The catheter 1420 comprises an elongate portion 1423 extending between a proximal end coupled to the handle 1421 and a distal tip 1424 which may be bendable. The bending lever 1422 can be for a uni- or bidirectional catheter meaning that the distal tip 1424 can deflect in one or two directions describing a position or shape that is considered its preferential neutral position or shape. If the initial configuration is the straight line then the catheter tip will deflect in two directions. If the catheter tip start at a bending position (180°) for example then one direction can be possible. The catheter 1420 optionally or alternatively comprises a frontal gripper 1425 adjacent to the proximal end of the elongate portion 1423.

When the catheter 1420 is to be operated in a patient's body the sterility of the catheter 1420 may need to be guaranteed. This means that prior to its use the catheter must be delivered in a sterile fashion and during its use care should be taken that it does not become insterile e.g. by entering contaminated zones outside the human body.

To avoid that the catheter loses sterility through contact with an embodiment of the present invention such as system 1300, care should be taken that it does at no instant in time come into contact with parts of the system 1300 that are non-sterile.

One method of ensuring this is to sterilise the entire apparatus or to sterilise any part of the apparatus with which the catheter may come into contact either directly or indirectly through convection, radiation, leakage or any other means.

Another method is to install and maintain a barrier between a so-called sterile zone in which the catheter is to reside and a non-sterile zone.

This can be done by using a surgical drape for sealing the sterile area from its surroundings. Drapes come in all kind of shapes and materials. Plastics are often used as they can seal hermetically while still being very flexible such that they do not interfere with the intended motion of the mechanism.

In many cases different materials and structures are combined in a drape. For example drapes may incorporate features that allow attaching them at certain locations of the surrounding mechanism. For example parts in harder plastic may be welded on top of them for this purpose.

Systems according to embodiments of the present invention may comprise a drape comprising means to releasably attach or that is designed to be permanently fixed to parts of the system such as to shield the internals of the sleeve from external interference. Typically the drape will be disposed after use, most typically together with one or more of the sleeve-based structures.

Figure 59:
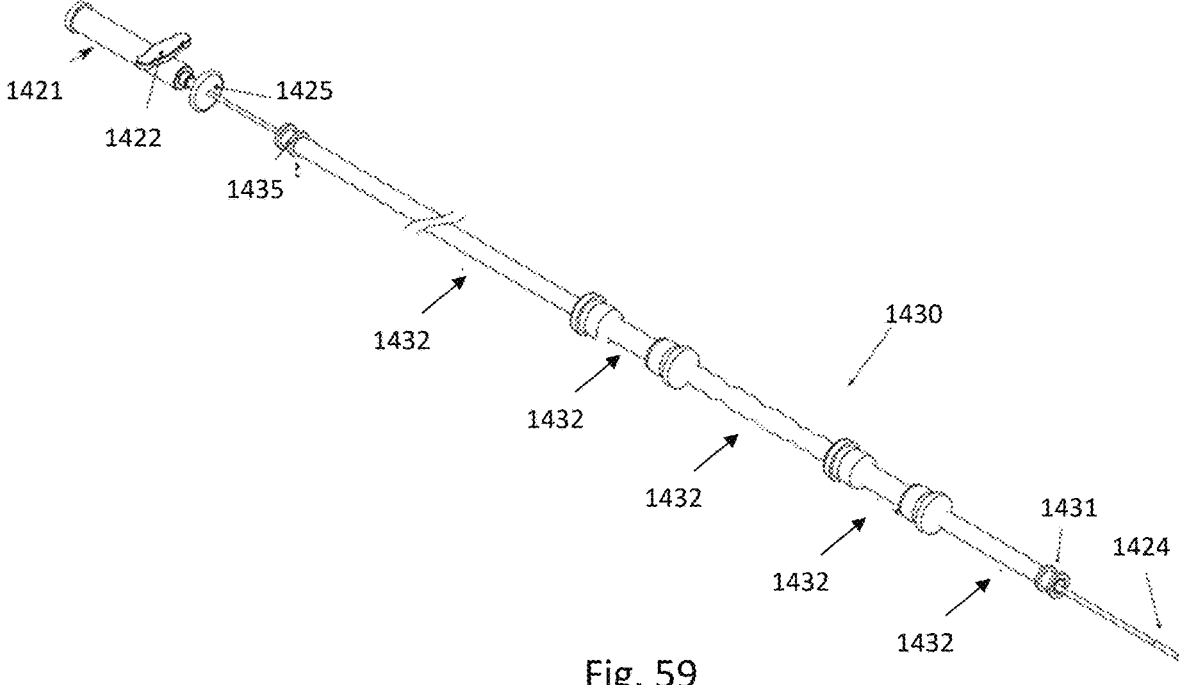
FIG. 59 is a perspective view of the catheter of FIG. 58 and a sterile drape.
Figure 60:
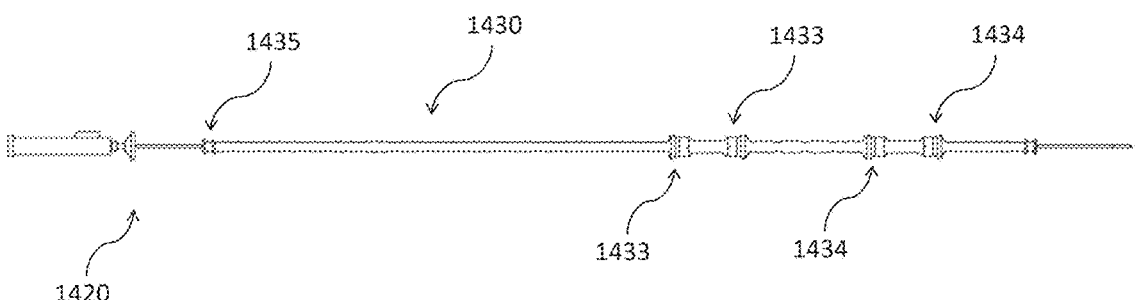
FIG. 60 is a side view of the catheter and drape shown in FIG. 59.
Figure 61:
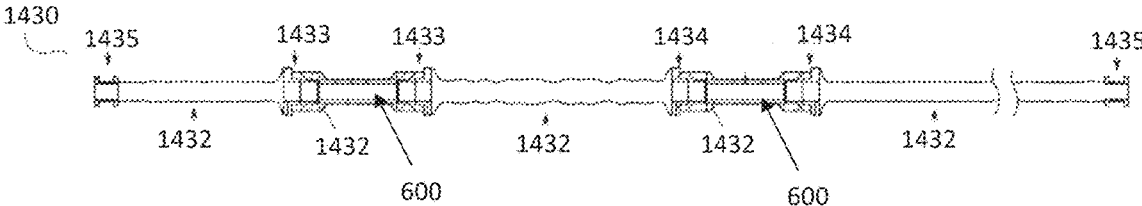
FIG. 61 is a side view of the drape shown in FIG. 59.

A preferred embodiment of a sterile drape 1430 is depicted in FIGS. 59 to 61.

The sterile drape 1430 comprises a connector portion 1431 configured to fix the sterile drape 1430 to the frame 950 of the translational module 1000, a flexible portion 1432, a first set of gripper connectors 1433, a second set of gripper connectors 1434, the sterile drape 1430 being preferably attached and subsequently locked into slots of the grippers 600, and a connector portion 1435 that is used to fix the sterile drape arrangement 1430 at a proximal side sufficiently far from the apparatus 1100 or system 1300 such that accidental contamination can be prevented.

The flexible portion 1432 comprises flexible drape material that can be attached in a sealed fashion at the connectors 1431, 1435. The connectors 1431, 1435 are preferentially made of a stiffer plastic material than the flexible portion providing a stable connection e.g. at the proximal side and distally at the frame 950. The flexible drape material comprising the flexible portion can be attached in a sealed fashion directly to the gripper connectors 1433 and 1434. Alternatively the flexible drape can be attached in a sealed fashion to another set of connectors (not shown) which are designed to be connected to the gripper connectors 1433 and 1434.

The flexible portion 1432 preferably accommodates elongation or contraction of the grippers as well as gross motion of the grippers relative to each other and relative to the frame of the linear motion portion 1000. The drape material is preferably be thin and foldable such that an excess of drape material can be provided for accommodating to the length variations. The excess of material should be determined carefully so that it does not exceed the necessary length. For example, care must be taken such that due to its length, the drape does not entangle between moving structures. Alternatively the drape may consists of stretchable material or folded in a bellows-like configuration such that it can stretch and relax upon relative movement of its extremities.

In a preferred embodiment the flexible drape is connected to the system 1300 or apparatus 1000 beforehand, e.g. by welding or by forming a single integral drape with multiple otherwise non-separable sections. Before use the integrity of these connections are preferably verified. However, an embodiment of the flexible portion 1432 may also comprise multiple separate drape portions that are connected just before the intervention on the spot e.g. by screw like connections.

Figure 62:
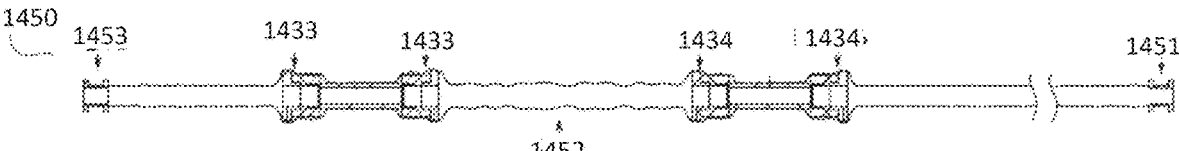
FIG. 62 is a side view of a sterile drape, as can be used in an embodiment of the present invention.

Referring to FIG. 62, in another embodiment 1450 of a sterile drape, the sterile drape 1450 comprises a connector portion 1451 that is used to fix the sterile drape arrangement 1450 to the frame 950 of the translational module 1000, a flexible portion 1452 and a connector portion 1453 that is used to fix the sterile drape arrangement 1450 at a proximal side sufficiently far from the apparatus 1100 or system 1300 such that accidental contamination can be prevented.

In this embodiment a single flexible portion 1453 is draped over the entire length between the connectors 1453 and 1451 running over the sleeve portions 600. Visual marks may be made beforehand on the drape to inform the surgeon how the drape is to be mounted together with the catheter in the apparatus 1000 or system 1300 such that at each location enough drape material is foreseen to ensure correct functioning of the drape independent of the relative motion of and by the grippers.

In another embodiment the flexible portion does not contain connector pieces, but is simply long enough so that it can be disposed far enough outside the apparatus to avoid accidental contamination.

In another embodiment a single drape may be provided together with a series of clamps that can be attached at any or some of the grippers or the frame, to fix the drape. Visual marks may be provided on the drape to inform the operator where to attach the clamps.

Using the sterile configuration of FIG. 59, 61, or 62, the catheter does not make contact with any of the drive system components and subsequently remains sterile.

The combination of the catheter (or another tubular structure) and the sterilization structure shown in FIG. 59 is made in a way such that it can be easily fixed to (or removed from) to the drive system. This entails more convenience for the surgeon (or the operator preparing the setup).

In a preferred embodiment the drapes and the sleeves are disposable. They arrive sterile in a preferred assembled form with instructions on how to introduce a sterile elongate member or catheter in them and instructions on how to check their integrity and subsequently further assemble them or mount them in the apparatus and are disposed of after use.

Figure 63:
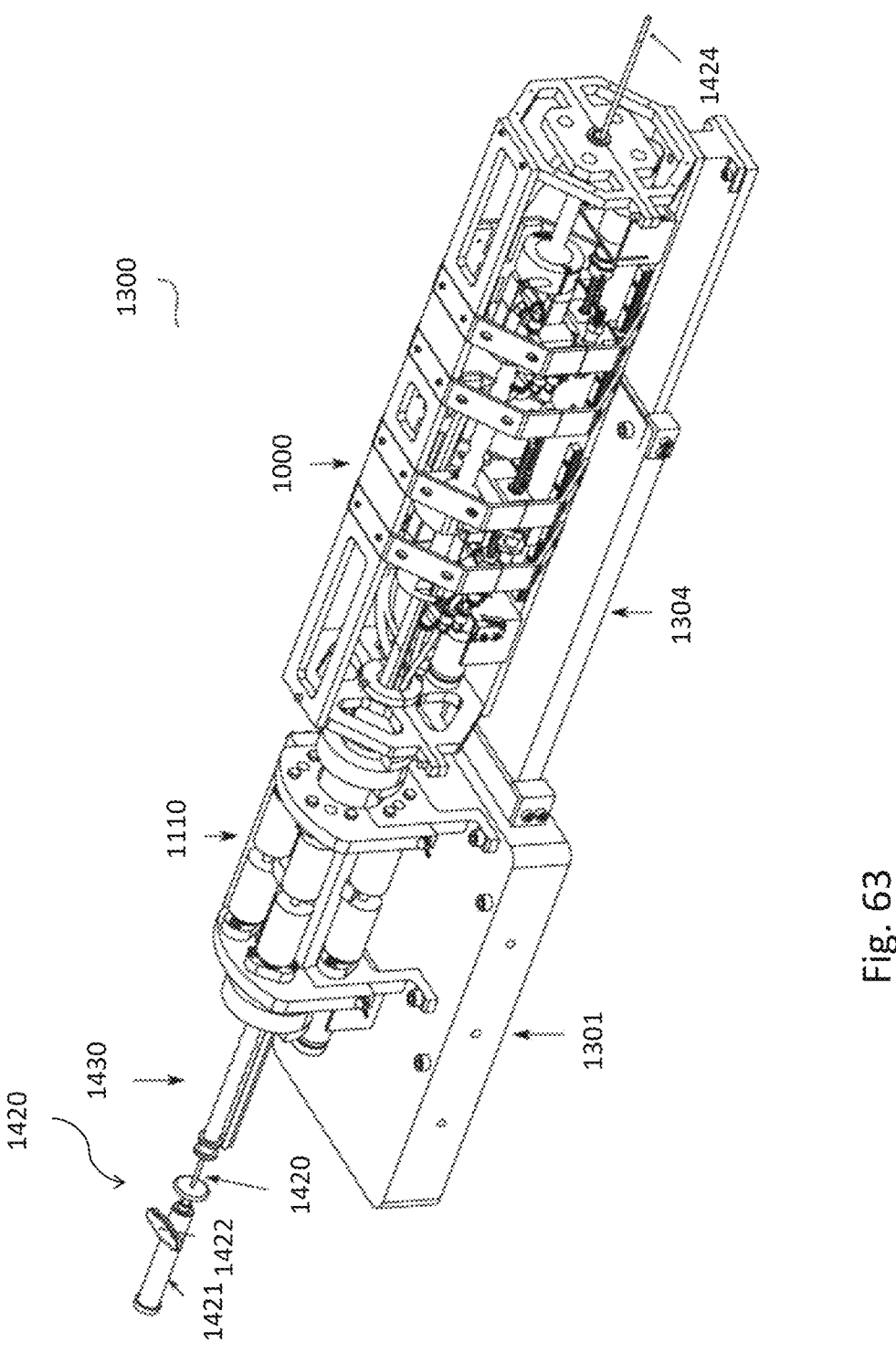
FIG. 63 is a perspective view of the system of FIG. 57 additionally comprising a sterile drape as shown in FIG. 59.
Figure 64:
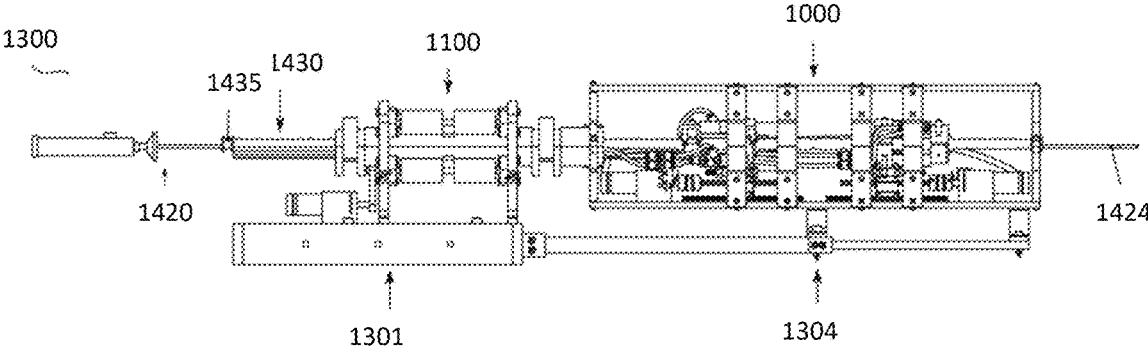
FIG. 64 is a cross-sectional side view of FIG. 63.
Figure 65:
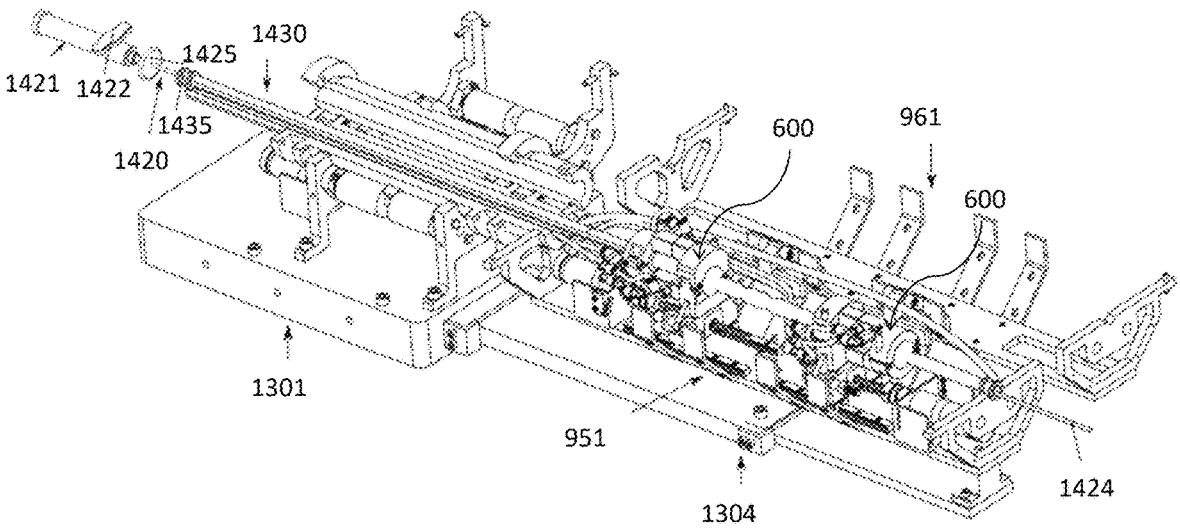
FIG. 65 is a perspective view of the system of FIG. 63 in an open configuration and a catheter introduced into the system.

Referring to FIGS. 63 to 65, an isometric view of a preferred embodiment of the system 1300 comprising a sterile drape 1430 is shown. The system comprises the linear module 1000, the rotary module 1110 fixed to the base 1301, the telescopic support arm 1304, and the surgical drape 1430 providing a sterile barrier. The system 1300 is shown with a catheter 1420 as an elongate member installed in the system.

Referring in particular to FIG. 64, the catheter 1420 with the drape can be seen clearly to be routed though the rotary module 1110 and the translational module 1000. The body of the catheter can thus be constrained by the grippers 600 and made to translate or rotate about its longitudinal axis. The telescopic support 1304 is extracted so that the drive may be opened as is visualised in FIG. 65.

Referring to FIG. 65, the system 1300 is shown in an open configuration showing how the catheter and the drape 1430 are routed. The catheter 1420 and the drape 1430 are placed in the rotary tube and through the two grippers 600. After opening the pair of grippers 600 the catheter 1420 can be extracted.

Figure 66:
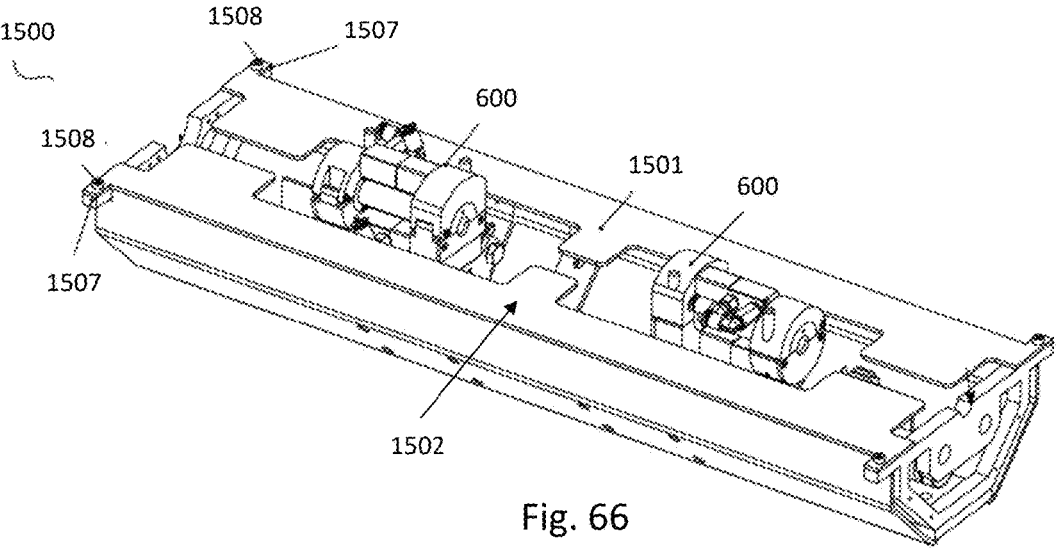
FIG. 66 is a perspective view of an alternative translation module according to embodiments of the present invention.
Figure 67:
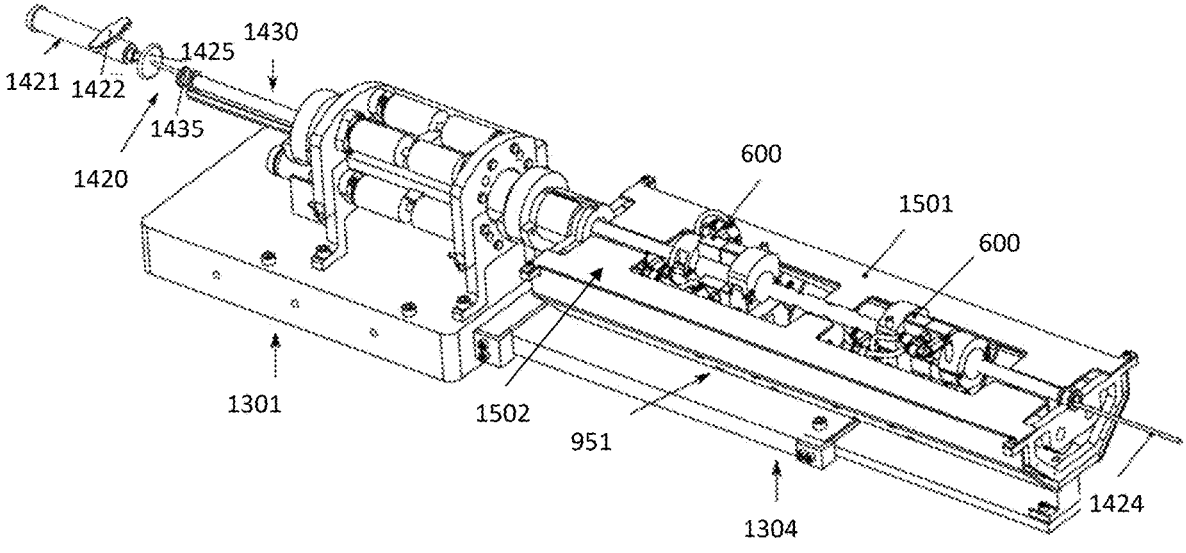
FIG. 67 is a perspective view of a system according to embodiments of the present invention comprising the translation module of FIG. 66.
Figure 68:
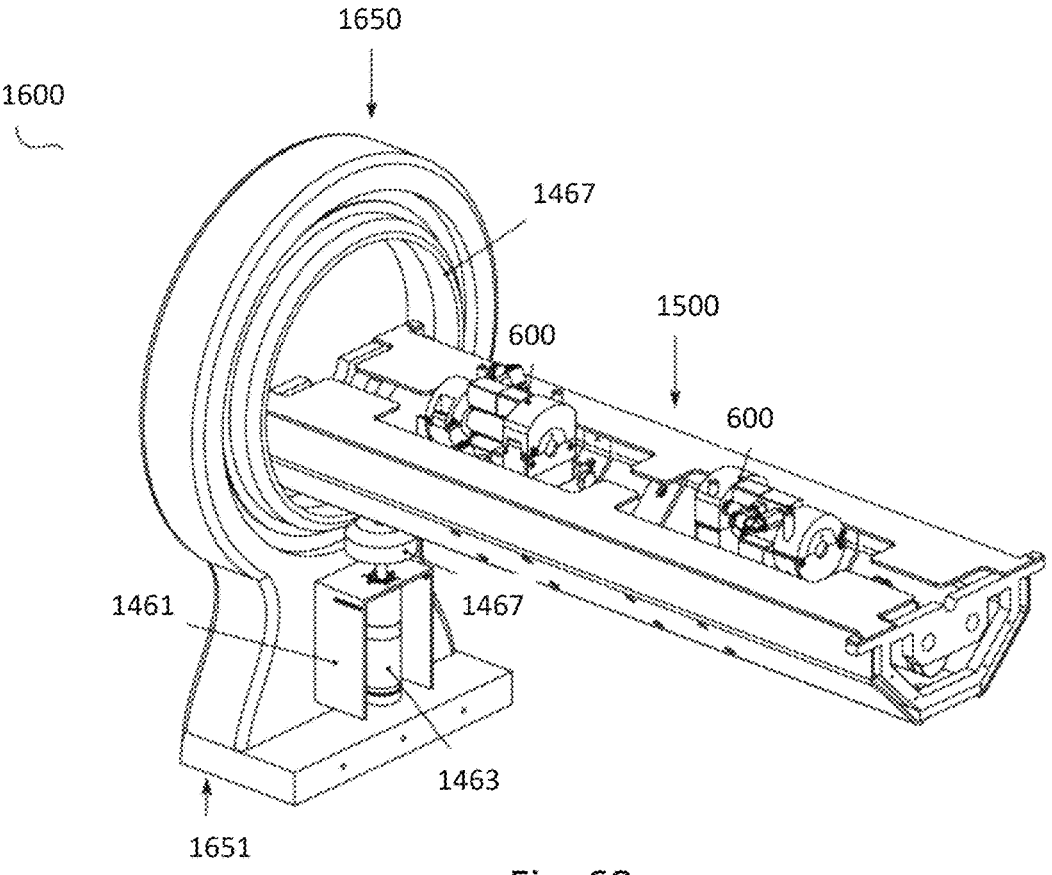
FIG. 68 is a perspective view of a system according to embodiments of the present invention comprising a rotational module and the translation module of FIG. 66.
Figure 69:
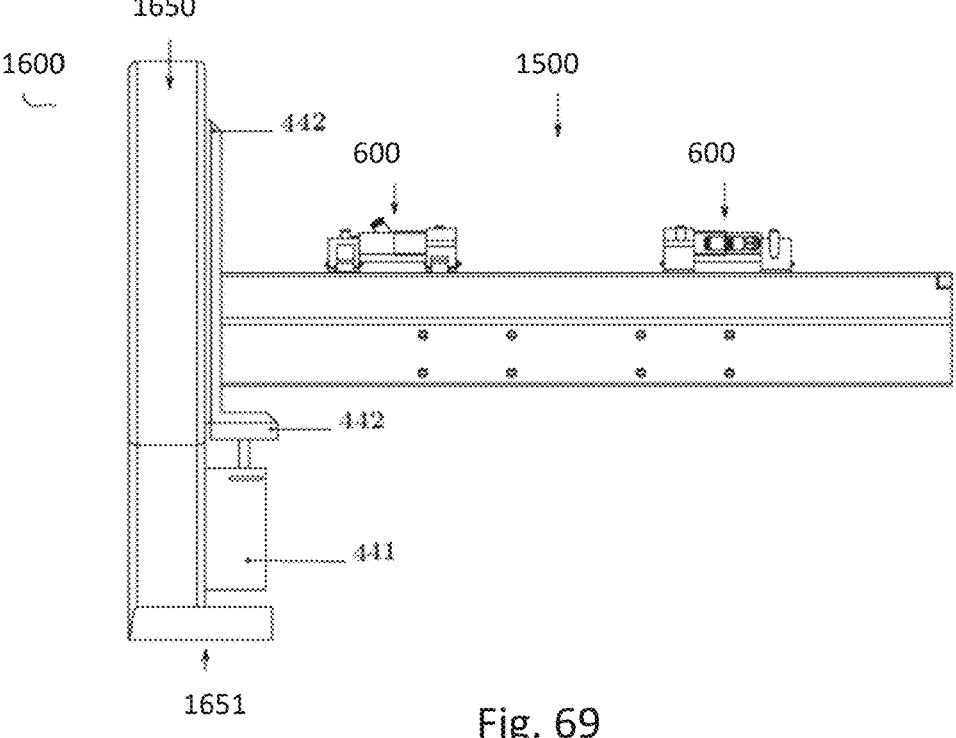
FIG. 69 is a side view of the system of FIG. 68.

An alternative to the design of the translational module 1000 is shown in FIGS. 66 and 67. The alternative translational module 1500 has some similarities to the system 1000, but also has some differences.

The differences are 1) The second part 961 of the frame is removed; 2) two plastic covers 1501, 1502 are added on the upper part of the first part 951 of the frame to isolate the inner components; 3) the translational module 1500 can be permanently fixed to a part of the rotary module 1110, such that upon opening of the rotary module the connection between both remains intact; (4) there is no longer the need for a telescopic support structure to support the frame when introducing, exchanging or retrieving tubular structures from the apparatus. The alternative module 1500 comprises mounting supports 1507 for fixing the module 1500 using screws 1508 to linear driver mounting support 1654 of a rotary module 1650 (described hereinafter).

Other ways to shield the internals of the translational module may be considered as well. In the embodiment of FIG. 66, the protective plastic cover 1501, 1502 of the translational module 1500 is shaped to allow for free translation of the grippers 600 without any collision; for easy mounting and removal of a catheter (or another elongate member) and its associated components and for easy cleaning.

All these aspects are advantageous for maintaining a sterile barrier. Easy mounting and dismantling of a catheter with sterile drape arrangement as in FIG. 59, helps guaranteeing sterility as the risk for unintentional damage to the drape reduces. Thanks to the more direct view it becomes also possible to detect possible anomalies faster.

A particular advantageous feature of this embodiment is that it relieves the need to open and close the two parts 951 and 961 of the frame 950, and gives better access to the catheter and sterile drape arrangements.

The improved access is beneficial in the sense that one can act faster and e.g. replace a catheter or convert from a robotic to a manual intervention in case of emergency or in procedures where one prefers manual operation for some parts and robotic for parts where high precision is needed.

FIGS. 68 to 71 illustrate a system 1600 according to embodiments of the present invention comprising the translational module 1500 and a rotational module 1650, as an alternative to the rotational module 1110, which has a ring-shaped structure.

The translational module 1500 is mounted onto the ring-shaped structure 1650 which is mounted on a base plate 1651. A motor 1463 bevel gear 1646 combination rotates the translational module 1500 about its axis.

The relatively large aperture of the ring-shaped structure makes it easy for an operator to introduce an elongate member through this aperture and guide it to the set of grippers 600. The actions that are needed to position, exchange or extract the elongate member are limited to the opening and closing of the easily accessible pair of clamping elements comprised in the grippers 600.

Figure 71:
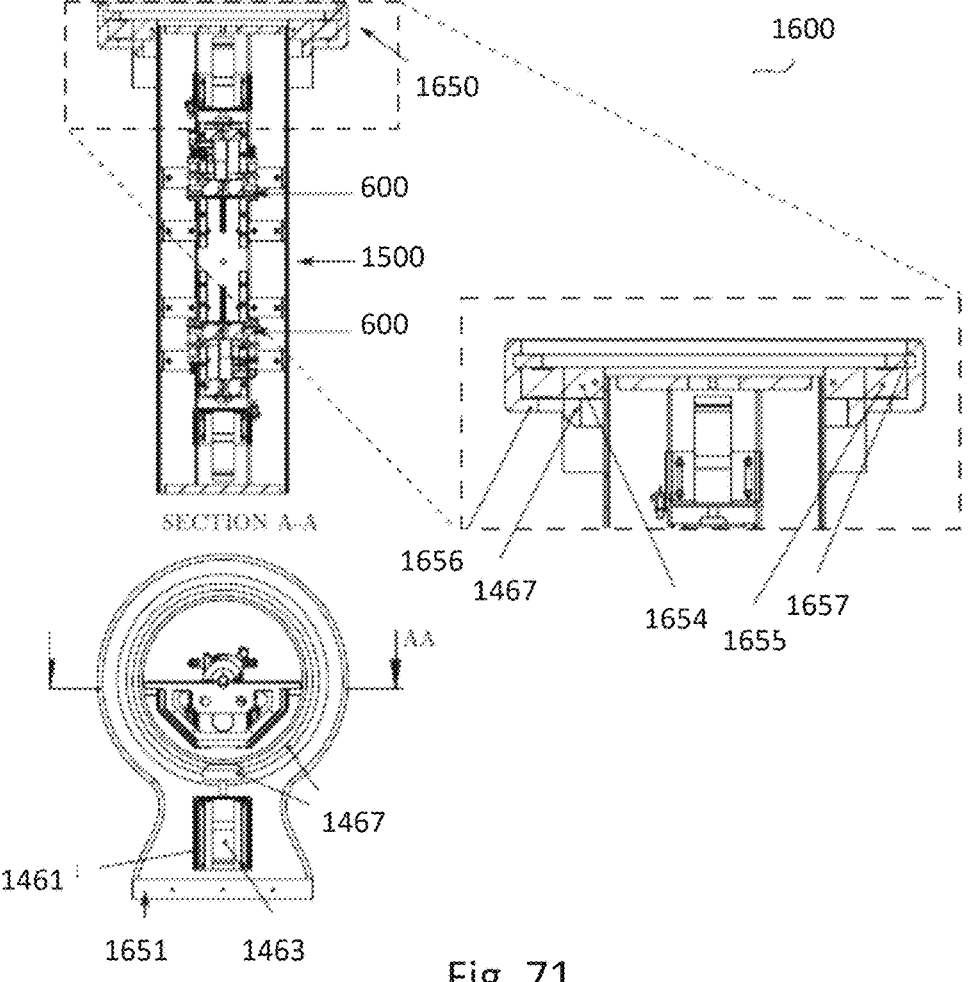
FIG. 71 is a sectional view of the system of FIG. 68.

The sectional view of FIG. 71 shows how the translational portion 1500 is fixedly connected to support ring 1654 that is rotatively fixed in bearing assembly 1655. A portion of a bevel gear 1653 is fixedly connected to this support ring 1654. By driving this bevel wheel the translational portion is caused to rotate about an axis that is aligned with the symmetry-axis of the rotational module 1650. Bearing assembly 1655 is mounted in housing 1656 and axially constrained by a shoulder in this housing at one side and a fixation ring 1657 at the other side.

Whereas in the presented embodiment the motor that drives the rotational motion is fixed to the side of frame 1658 in other embodiments this motor may be integrated on the translational portion 1500 as well. It would then turn together with the translational portion working e.g. against an internal gear that could be clamped in the ring-like structure. Alternatively a capstan drive may be comprised in the system 1600, where cables are routed along an extrusion from the ring-shaped structure. Any other approach known in the-state-of-the art to drive a part within a ring-like portion may be used.

The rotational drive system is preferably equipped with brakes such that upon power failure or any other failure or emergency the rotation of the elongate member would be prevented. Alternatively the drive system may be non-backdrivable such that the rotational structure would not move naturally upon power failure.

Note that a preferred design would distribute the system's weight evenly about the longitudinal axis of the translational portion 1500 such that through good balancing and gravity compensation the module would naturally stop moving even for backdrivable systems. One way to come to this behaviour could consist of adding statistically designed weights for counter-balancing. This property would not only be advantageous upon power failure but could also simplify the control as the response time and effort required to accelerate would become much more constant and easy to predict.

Figure 72:
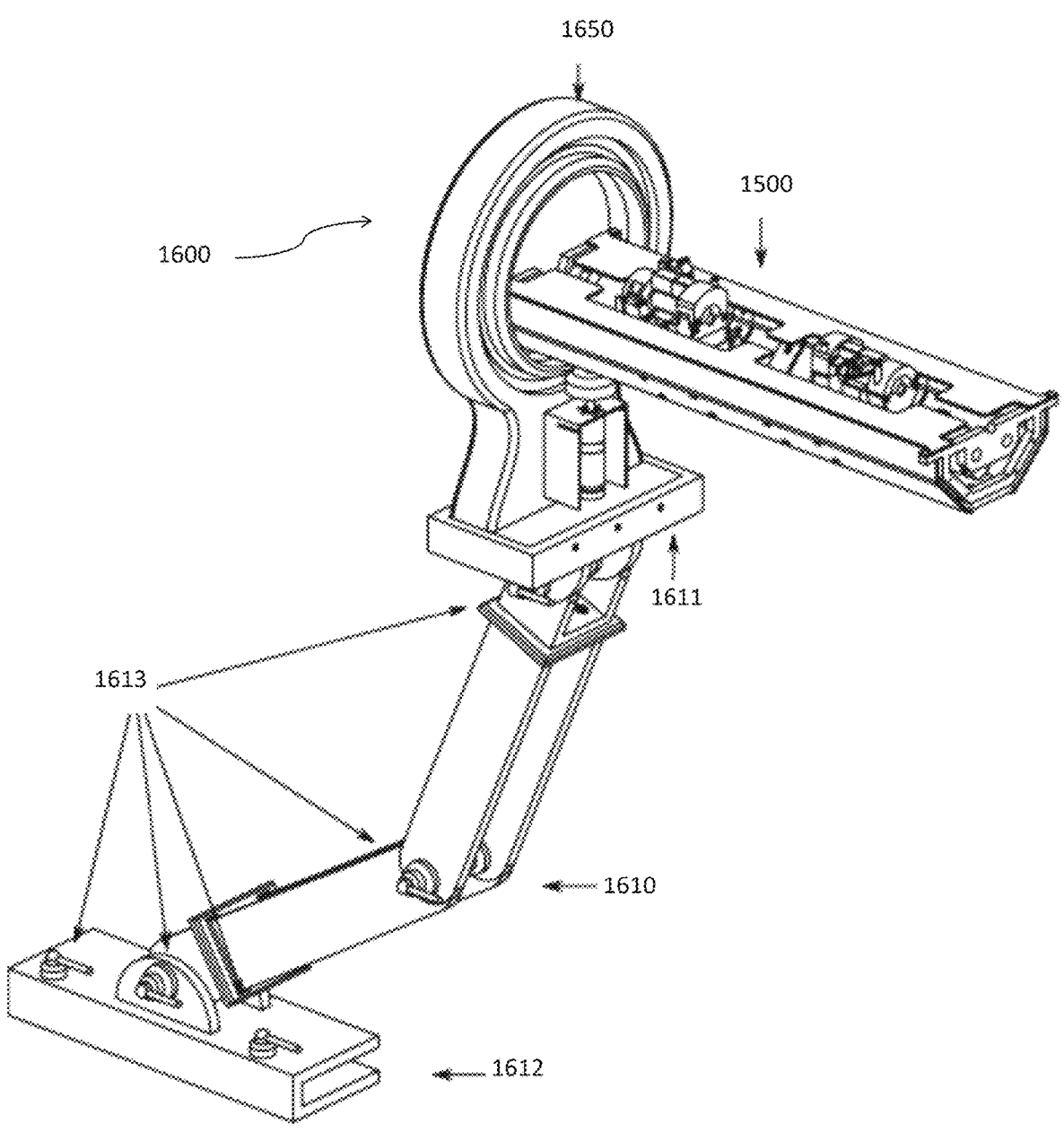
FIG. 72 is a perspective view of apparatus comprising the system of FIG. 68 and a kinematic arm.

Referring to FIG. 72, the system 1600 can be coupled to a kinematic structure 1610, similar to the structure 1310 of FIG. 45, for mounting on for example an operating table (not shown). The rotational module 1650 is removably coupled to a base 1611 comprised in the kinematic structure 1610. The translational module 1500 is coupled to the rotational module 1650. The kinematic structure 1610 comprises, at an opposite end to the base 1611, a clamp 1612 for coupling to for example an operating room table (not shown). The kinematic structure 1610 comprises screw fixings 1613 for fixing parts of the kinematic structure 1610 into place and allows reconfiguration of the kinematic structure 1610.

Other kinematic structures may be employed to align and position systems or apparatus according to embodiments of the present invention in a stable manner and relative to the patient, the operating room table or any relevant inertial frame can be employed as well. For example one may want to mount systems or apparatus according to embodiments of the present invention to the ceiling or a side-wall. The design of the apparatus and of a fixation and alignment system may be conducted to allow operation in collaboration with an MRI machine or any other relevant imaging device or apparatus.

Elongate members that provide additional motion capabilities such as catheters, guidance sheaths or guidewires with distal bending capabilities, such as the catheter 1420 (FIG. 58), may be steered by any appropriate embodiment of the present invention.

An elongate member may comprise any kind of distal tip catheter 1420. Special care may be paid to teach the system the length of the elongate member that is loaded, the targeted motion range and the relative position of the elongate member with respect to the apparatus. The latter may be done at the start of the procedure through a kind of registration, calibration or measurement step or it may be done continuously by monitoring the relative pose of the elongate member by a dedicated sensor.

When driving a catheter comprising features or regions that are not to enter the main body of the apparatus, such as for example, the handle portion 1421, the system may be configured so as to produce an alert or halt the machine when this portion comes too close to a certain boundary region.

Systems and apparatus according to embodiments of the present invention may be tailored or configured to drive elongate members having such additional motion capabilities whereby the system or apparatus is configured to control the propulsion, possibly following reference input signals provided by a remote control joystick or from switches or a human interface positioned anywhere conveniently, along and rotation about a longitudinal or portion of a longitudinal axis, whereas an operator controls the additional motion capability, for example in the case of catheter 1420 manipulating a lever 1422.

Alternatively, the apparatus or system may be fitted with a portion that is designed to drive the additional motion capability in a computer-controlled manner. The control signal determining the steering of the system can come from a user interface or from a dedicated path planning program.

Systems and apparatus according to embodiments of the present invention may comprise actuation or control systems configured to steer the additional motion capabilities, for example in the case of catheter 1420 by controlling the position of the lever 1422.

Figure 73:
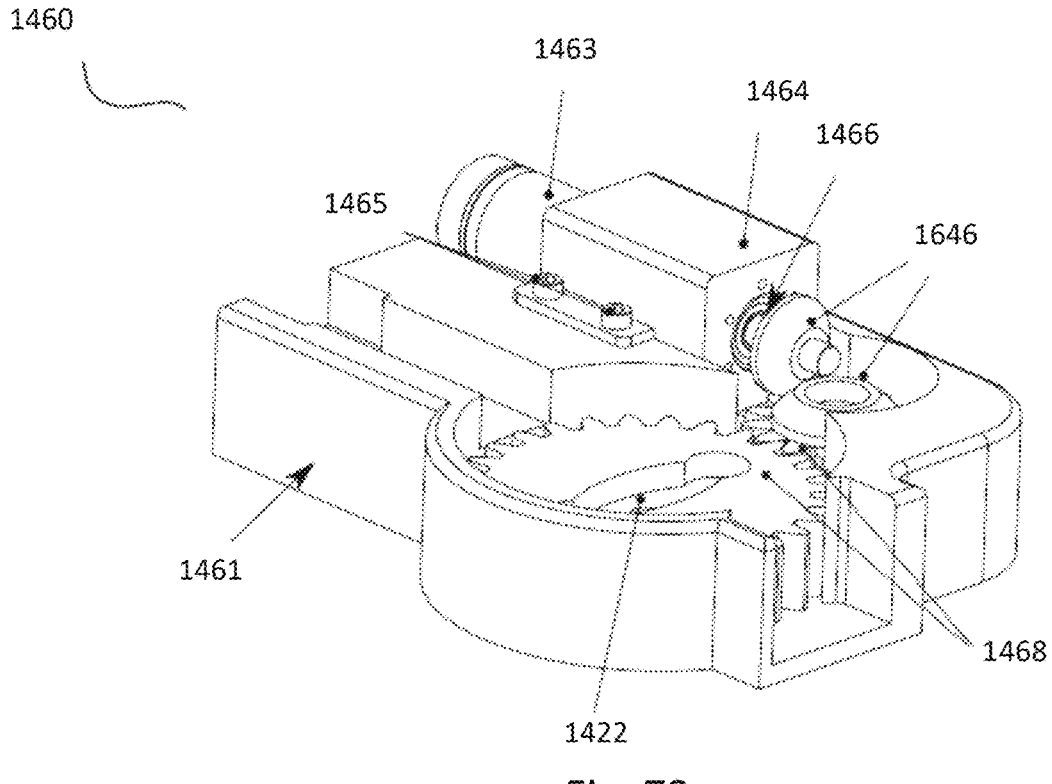
FIG. 73 is a perspective view of a distal tip actuation module which may be comprised in systems, apparatus, or devices according to embodiments of the present invention.
Figure 74:
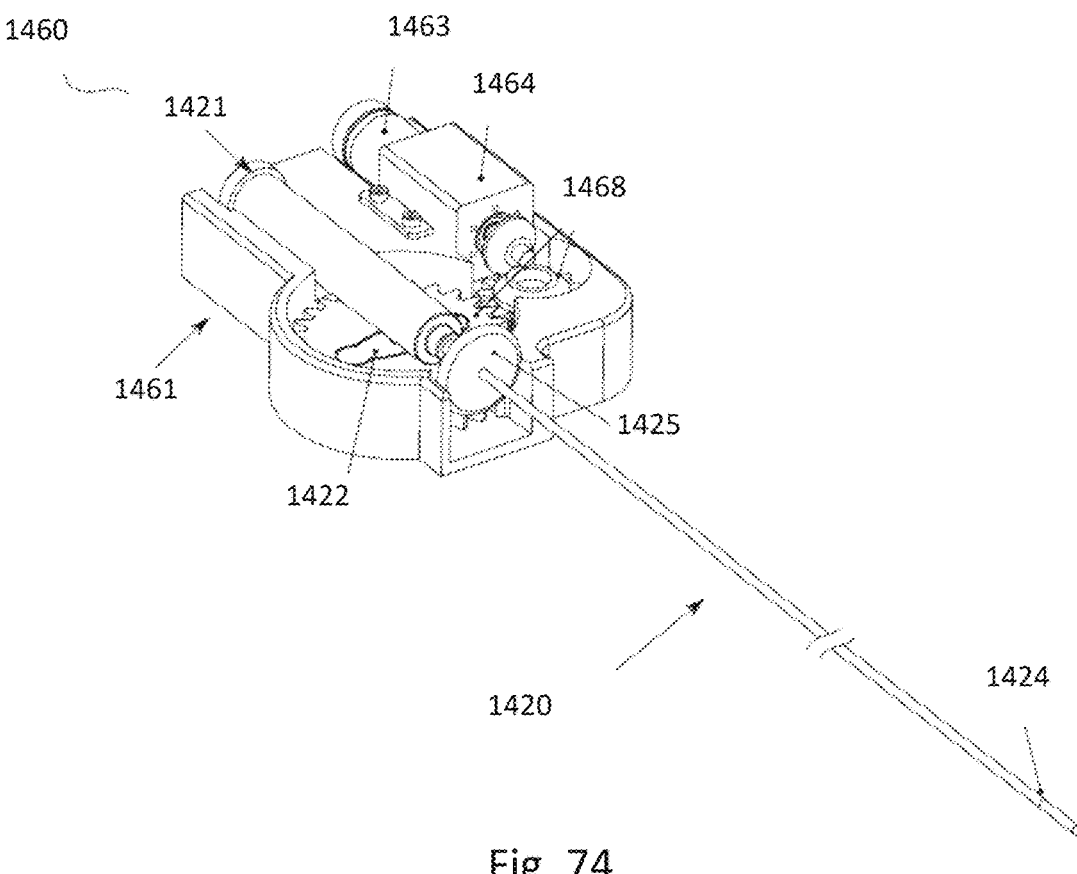
FIG. 74 is a perspective view of the distal tip actuation module of FIG. 73 and a catheter installed in the distal tip actuation module.
Figure 75:
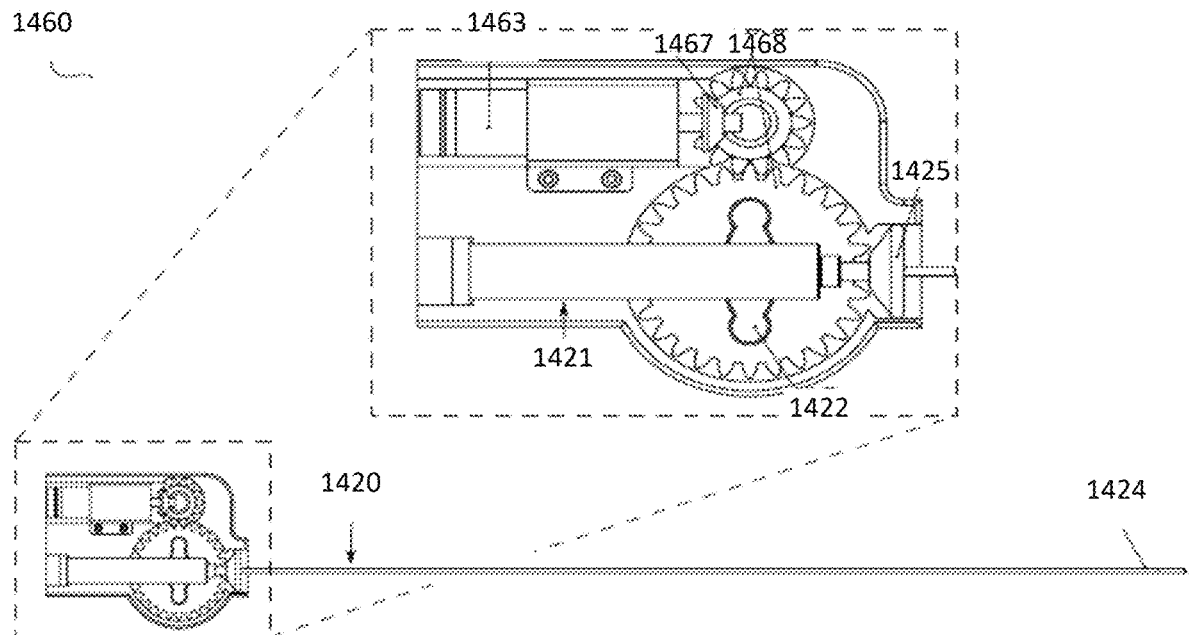
FIG. 75 is a plan view of FIG. 74.

Referring to FIGS. 73 to 75, a distal tip actuation system 1460 is shown which may be comprised in systems or apparatus according to embodiments of the present invention, in particular when the elongate member comprises a catheter 1420 (FIG. 58) comprising a lever 1422 that can be rotated to bend the distal tip 1424 of the catheter 1420.

The distal actuation system 1460 comprises a rigid housing 1461 which supports parts of the a distal drive unit 1460. The actuation of the lever 1422 is provided by a motor 1463. The motor is fixed to a housing 1464 which is on its turn fixed by a pair of screws 1465 on the housing 1461 of the distal drive actuation portion.

The outgoing axis 1466 of the motor 1463 is connected to a bevel gear assembly 1467. Upon rotation of the motor shaft this assembly 1467 transfers its motion to a pair of spur gears 1468 mounted onto the housing 1461.

The catheter 1420 can be removably mounted onto the driver's base by fitting the catheter's bending lever 1422 into a cut out extrusion 1469 of the driven gear 1468.

The larger driven gear 1468 contains a cut extrusion 1422 that resembles the shape of the catheter's bending lever 1422. The catheter is mounted onto the driver's base 1461 by fitting the catheter's bending lever 1422 into the cut extrusion 1469 of the driven gear 1468.

The catheter's handle 1421 and frontal grip (if existing) rest on the base 1461 of the drive. The base 1461 is also configured to constrain the rotation of the catheter. A latch (not shown) may be added to further constrain any other motion of the catheter 1420 with respect to the base.

The gear 1468 can rotate freely in both directions. Depending on the requirement, the limits to the rotation of the gear 1468 can be set. For example, some catheters are unidirectional meaning that they only require one direction of rotation to bend the catheter's distal tip.

The rotation of the gear 1468 is coupled to the rotation of the catheter's bend lever 1422. Hence, a rotation of the gear 1468 would result in the bending of the distal part 1424 of the catheter.

Following the shape of the handle or of any other interface that is used to control additional motion capability of a specific elongate member desired to be controlled, other embodiments and housings may be used. In addition, other type of drive systems not limited to an electromagnetic actuator and gear-based transmissions may be used advantageously to actuate the handle or those particular interfaces to obtain a desired control and precision over the additional motion capability.

Referring to FIG. 74 in particular, it is illustrated how the catheter 1420 can be mounted at its handle portion 1421 onto the distal tip drive system 1460.

An embodiment of a distal tip actuation unit, such as 1460, can be combined with apparatus 1000 or systems 1300 or 1600 or other embodiments of the present invention as described herein, to form an apparatus that can jointly control inherent motion capabilities of an elongate member as well as translate the elongate member along its longitudinal axis and to rotate the elongate member about an axis that is coincident with its longitudinal axis.

Preferably the distal tip actuation unit is combined with apparatus 1000 or systems 1300 or 1600 or other embodiments of the present invention as described herein such that the motion capability of the distal tip actuation unit can be addressed independently, that is, both the distal tip actuation unit and the system or apparatus 1000, 1300, 1600 can both be controlled independently with minimal degradation of control precision side or bandwidth caused by one to the other.

Figure 77:
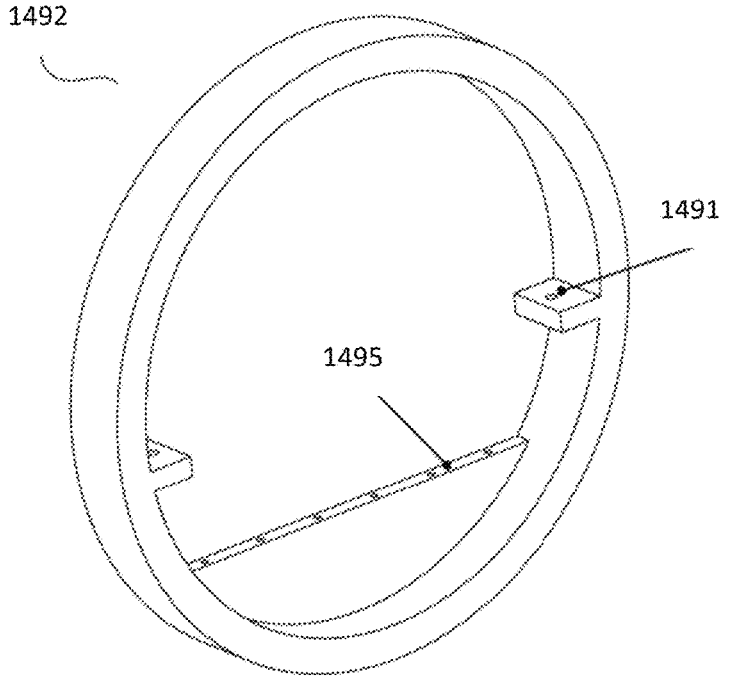
FIG. 77 is a perspective view of a ring structure comprised in the rotary module of FIG. 76.
Figure 76:
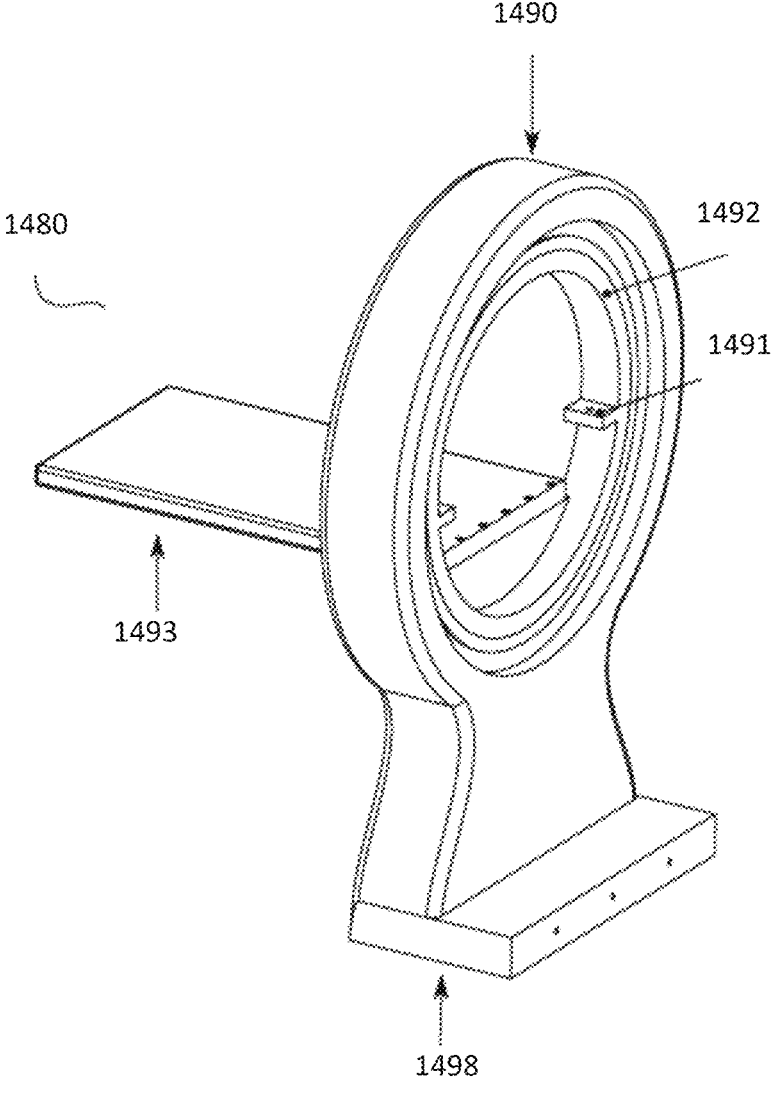
FIG. 76 is a perspective view of a rotary module which may be comprised in a system, device, or apparatus according to embodiments of the present invention.
Figure 78:
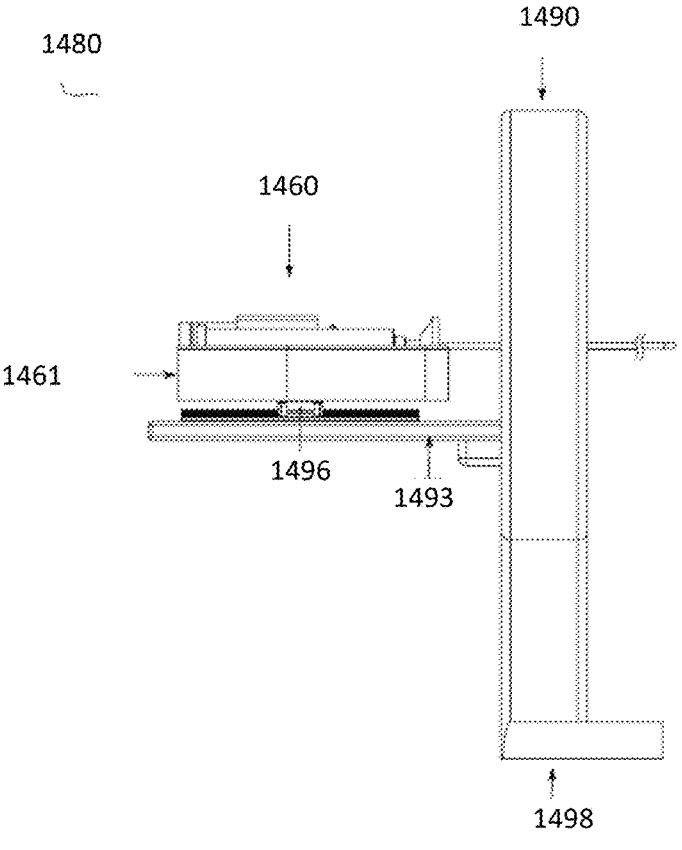
FIG. 78 is a side view of the rotary module of FIG. 76.
Figure 80:
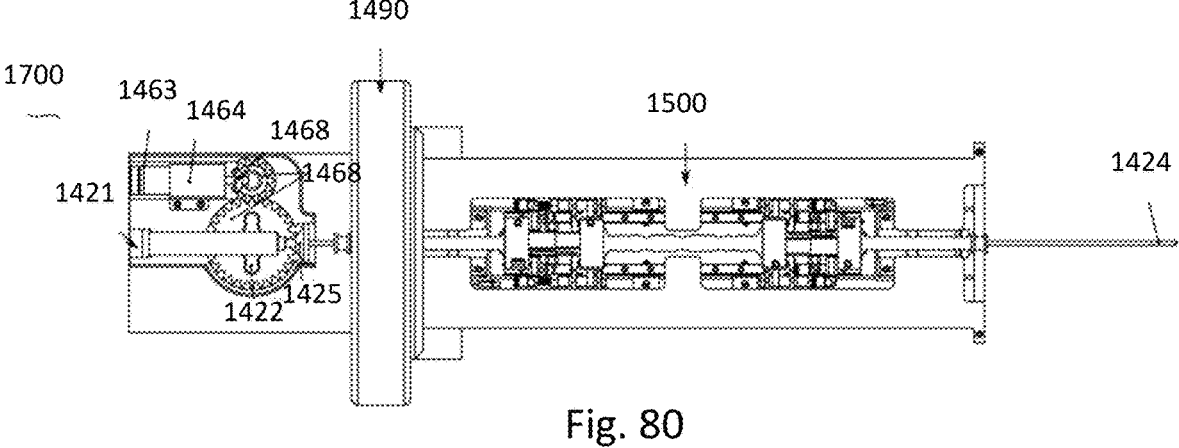
FIG. 80 is a top view of the configuration of FIG. 79.

Referring to FIG. 76 to 78, a rotary module 1480 according to embodiments of the present invention is shown to which a distal tip actuation unit such as the distal tip actuation unit 1460 can be connected to allow unhindered rotation and translation of the catheter or other elongate member.

Using the ring-shape structure 1490 that is depicted in FIG. 77, the translational module 1500 can be clamped to the support 1491 of the inner rotatable mounting ring 1492 comprised in the ring-shape module 1490.

A plate 1493 can also be attached to the mounting ring 1492. The distal tip actuation system 1460 of FIG. 73 can be mounted on this plate 1493. As both the distal tip actuation system 1460 and the translational module 1500 are then rigidly connected to the mounting ring 1492 there will be no relative motion between the distal tip actuation system 1460 and the translational module 1500. When the translational module is tilted by the rotary module 1480 the distal tip actuation system 1460 will be tilted with the same amount.

When mounting the distal tip actuation system 1460 on plate 1493, a preferred approach would take care that the alignment axis of 1460, or at least of a catheter or elongate member that is clamped in it, is maximally coaxial with the longitudinal axis of the translational module 1500, although other configurations, e.g. to save space may be envisioned as well.

FIG. 77 provides an isometric view of an embodiment of a rotary drive mounting ring 1492. A similar structure may be reached by assembling multiple pieces. FIG. 77 shows a possible way to clamp the translational module 1500 at the mounting support 1494 and the distal tip actuation system at the support ridge 1495. The plate 1493 preferably comprises an adequate number of sink holes to pass screws and of a shoulder portion to allow stable fixation to the ridge 1495.

FIG. 78 shows in a side view how the distal tip actuation system 1460 can be mounted on the plate 1493 such that it experiences the same rotation as for the translational module 1500. The figure shows how the distal tip actuation system 1460 is mounted on a slider 1496 of a translation stage that allows the distal driver to move freely in a direction parallel to the longitudinal axis of the catheter or other elongate member.

Figure 79:
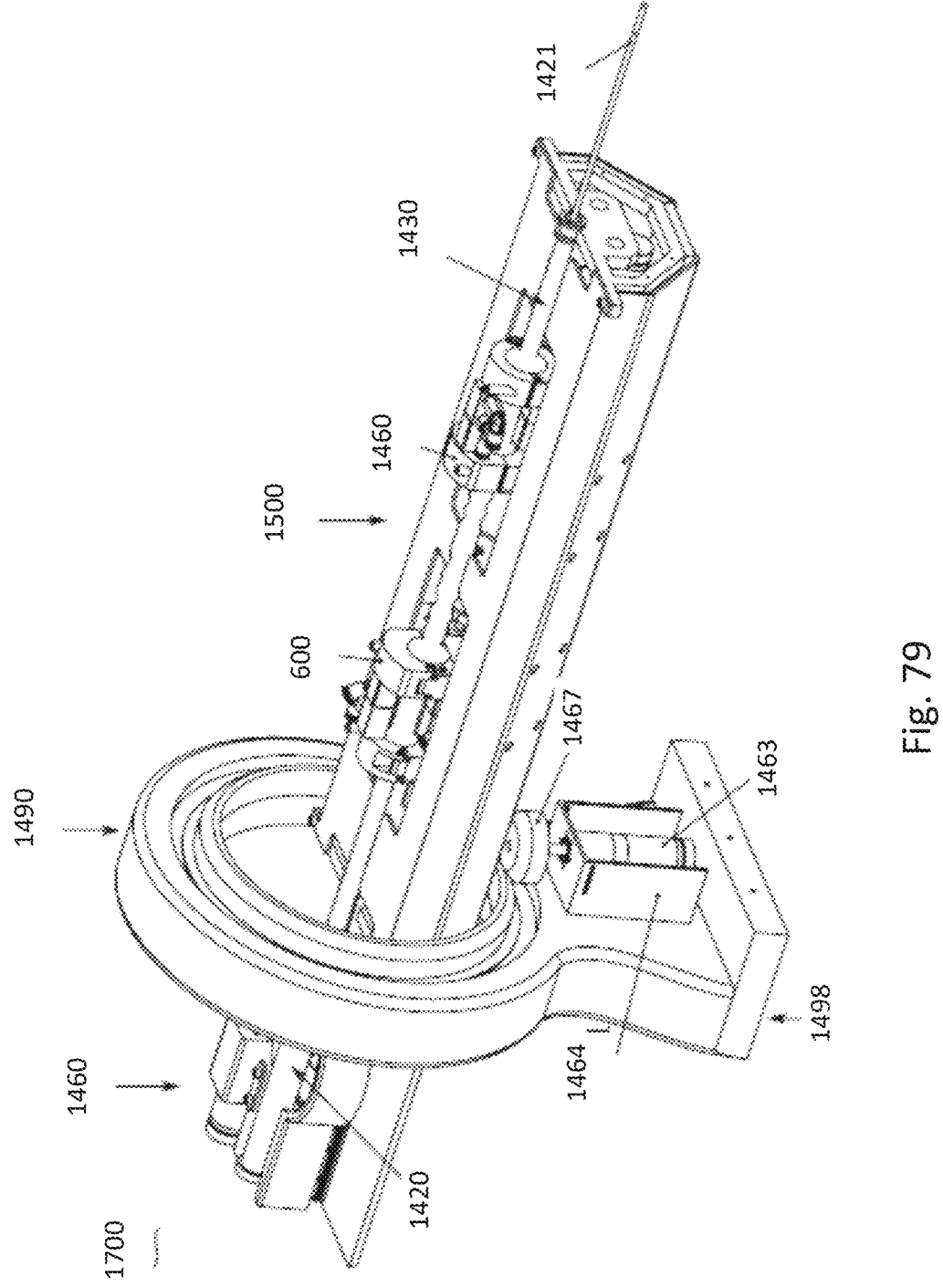
FIG. 79 is a perspective view of apparatus according to embodiments of the present invention comprising the rotary module of FIG. 76 and a catheter installed in the apparatus.

Referring to FIG. 79, the rotary module 1480 and distal tip actuation unit 1460 can be comprised in a system 1700 according to embodiments of the present invention. The distal tip actuation system 1460 can be used to for example to clamp a commercially-available catheter 1420 with associated drape assembly 1430 to the catheter distal driver 1460 and at the same time to the translational module 1500. Both the distal drive unit and the translational module are attached to the rotary module 1490 which is fixed with its base 1498 to the external world.

Figure 81:
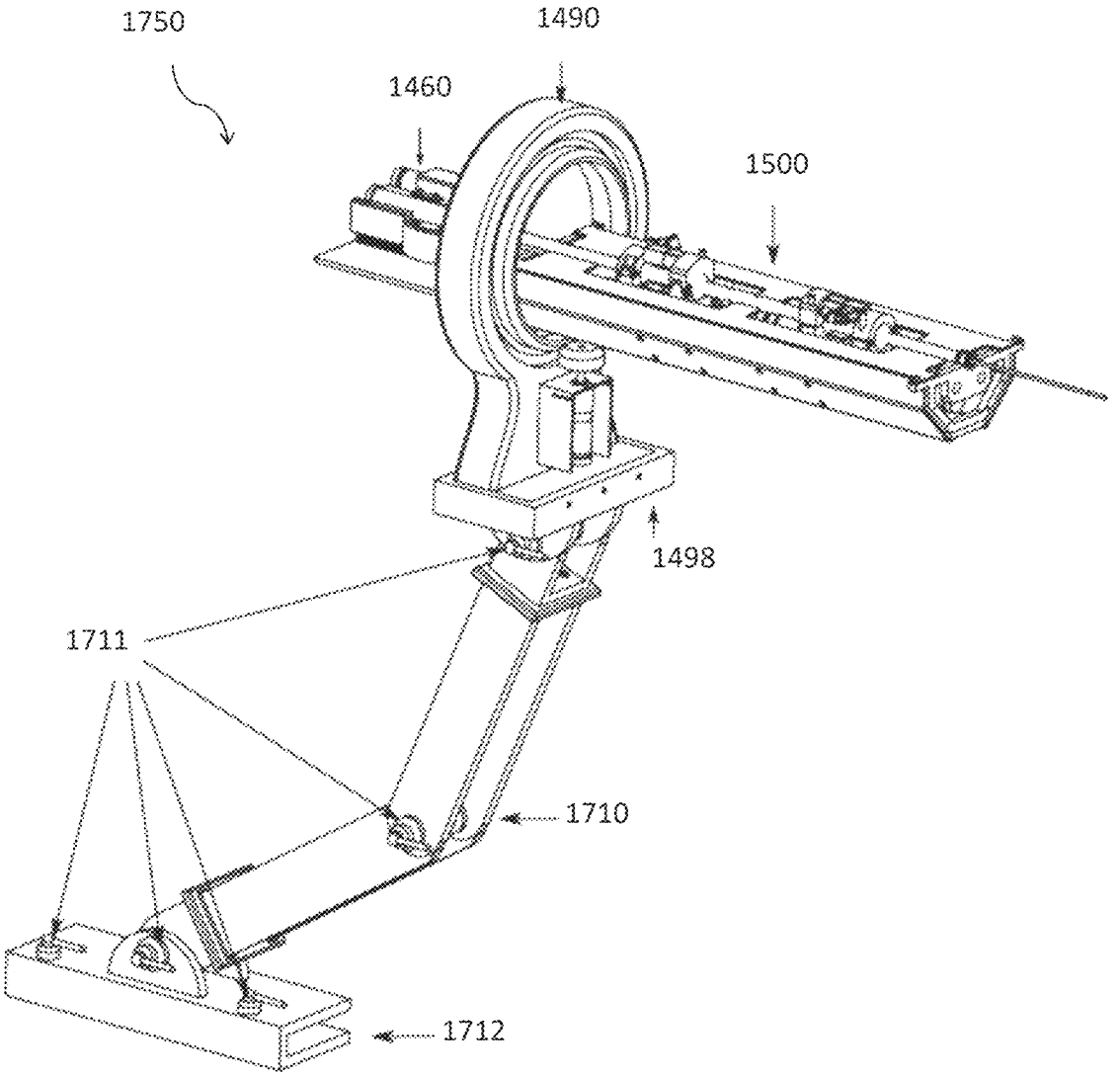
FIG. 81 is a perspective view of a system comprising the apparatus of FIG. 79 and a kinematic arm coupled to the apparatus, wherein a catheter is shown installed in the apparatus but the apparatus may be provided without the catheter.
Figure 82:
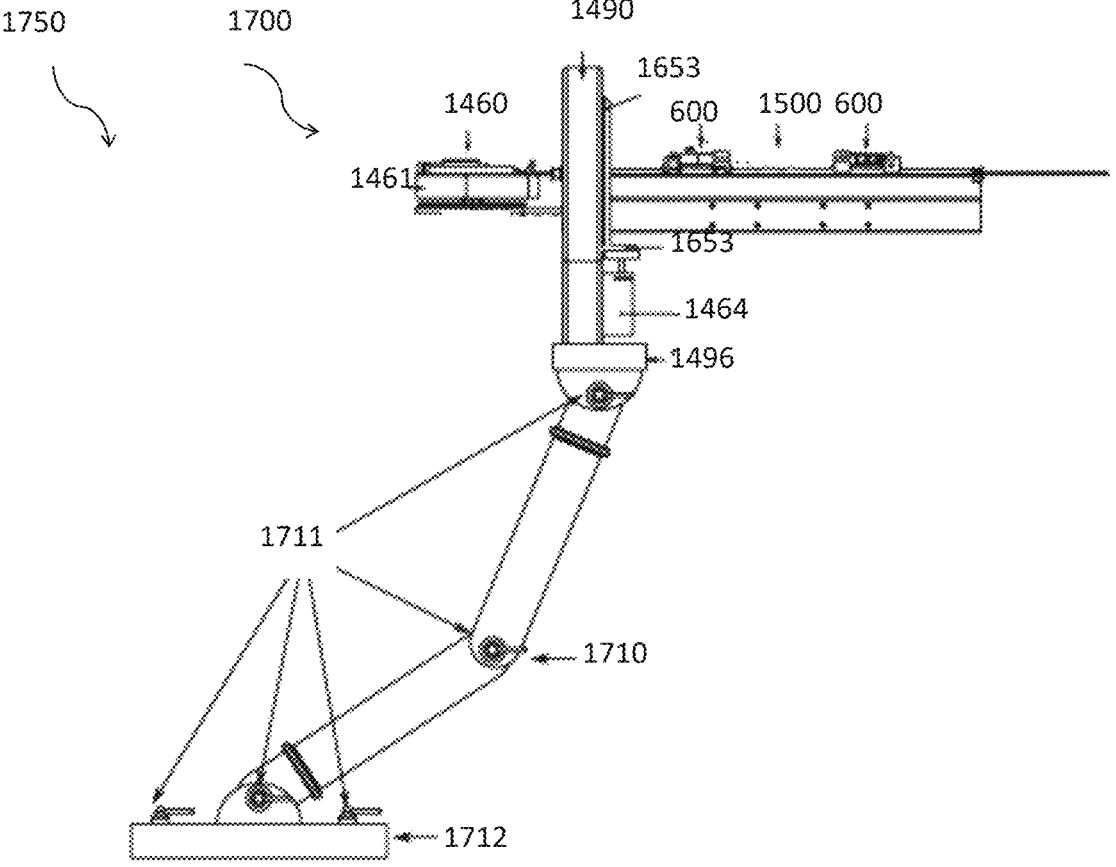
FIG. 82 is a side view of the configuration of FIG. 81.

Referring to FIGS. 81 and 82, the system 1700 can be coupled to a kinematic structure 1710 to form a composite system 1750, similar to the structure 1490 of FIG. 45, for mounting on for example an operating table (not shown). The base 1498 of the rotational module 1490 is removably coupled to the kinematic structure 1710. The translational module 1500 is coupled to the rotational module 1490. The kinematic structure 1710 comprises, at an opposite end to the base 1498, a clamp 1712 for coupling to for example an operating room table (not shown). The kinematic structure 1710 comprises screw fixings 1713 for fixing parts of the kinematic structure 1710 into place and allows reconfiguration of the kinematic structure 1710.

Embodiments of the present invention can be used advantageously in more complex procedures that require combined use of two or more elongate members.

Embodiments of the present invention provide means to drive multiple elongate members based on a plurality of drivers that can be positioned in different appropriate configurations. Alternative embodiments of the present invention may be provided that combine a plurality of distal bending actuation unit(s) 1460, translational drive unit(s) 1500 or rotational drive unit(s) 1650 with possible addition of further drive features.

When the elongate members function in a coaxial configuration, e.g. where one structure is concentric to a second structure and the first is to pass through a lumen of the second or vice versa, a plurality of systems according to embodiments of the present invention arranged in a cascaded fashion can be provided.

Figure 83:
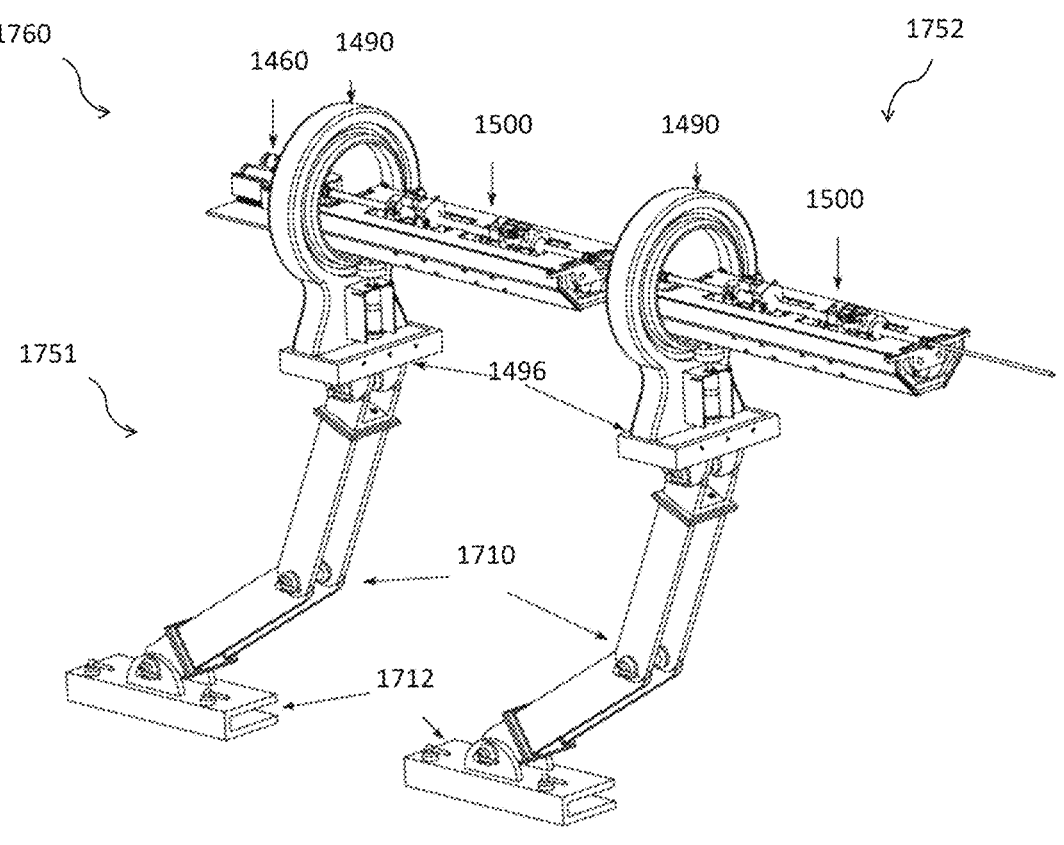
FIG. 83 is a perspective view of a first chained arrangement of systems according to embodiments of the present invention.
Figure 84:
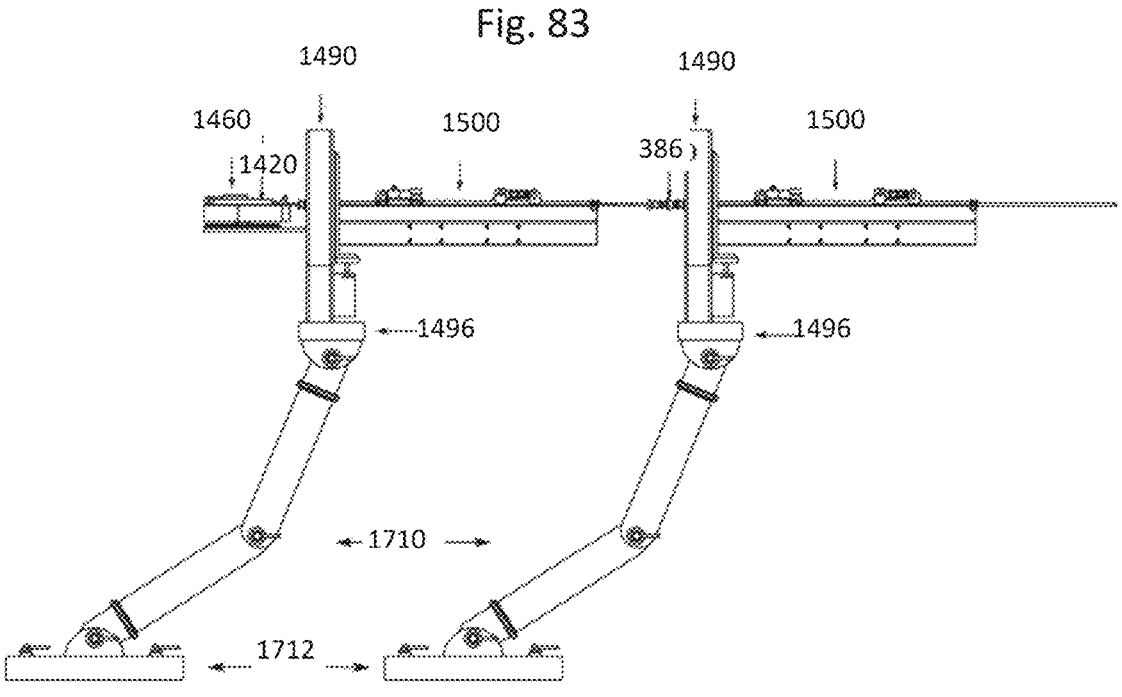
FIG. 84 is a side view of the configuration of FIG. 83.

Referring to FIGS. 83 and 84, a system 1760 according to embodiments of the present invention comprises a cascade arrangement of a first system 1761 similar to the system 1750 and a second system 1762 similar to the system 1750 but without a distal tip actuation unit. The systems 1761, 1762 are arranged approximately co-axial allowing jointly steering of two different concentric elongate members. The cascaded arrangement is using two separate kinematic joint mechanisms 1710. The two mechanisms can be aligned in a way to allow a simultaneous use of the distinct drive systems. The separate joint mechanisms can be fixed to the same Operating Room (OR) table or other different objects.

Figures 85, 86:
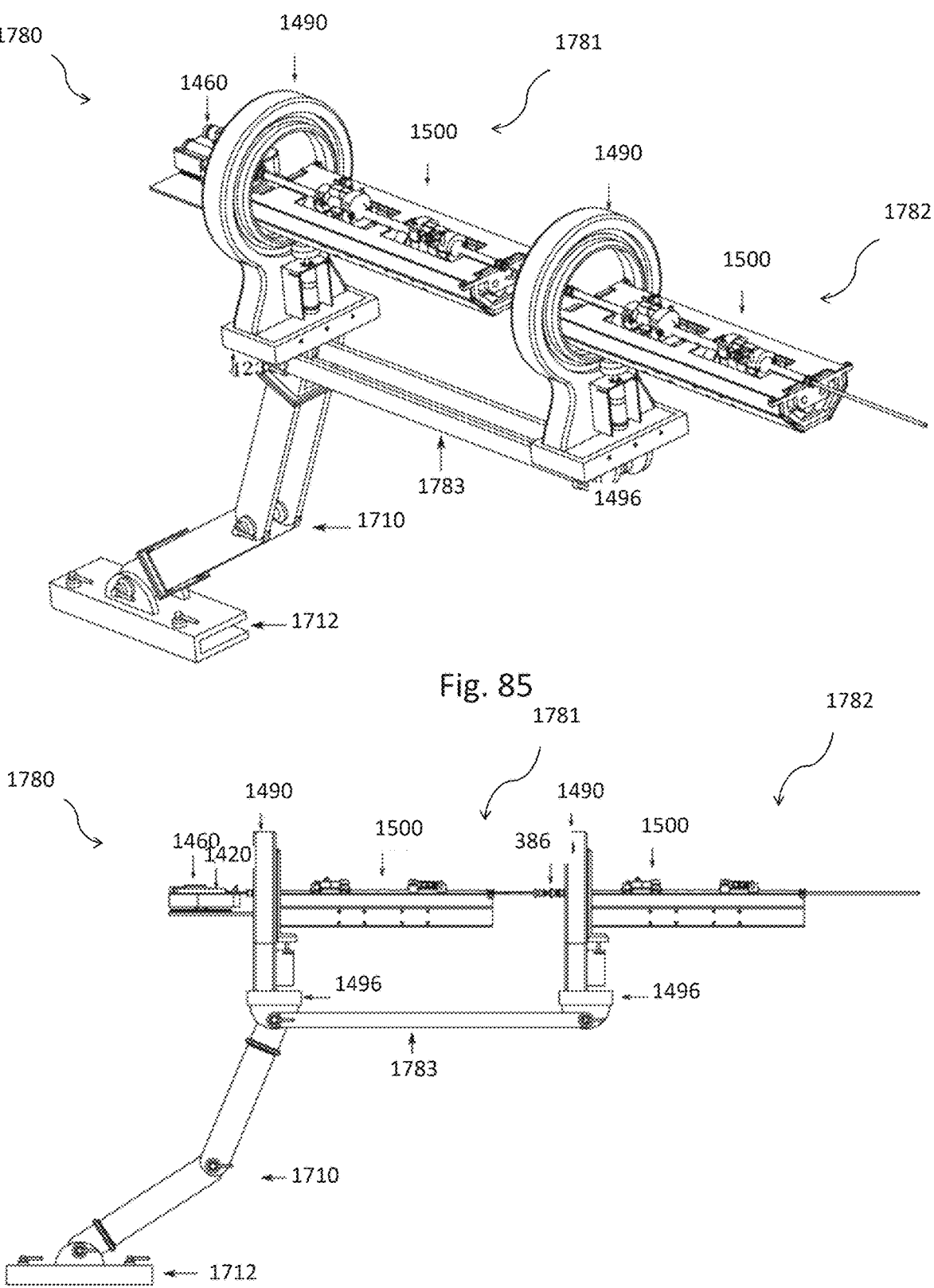
FIG. 85 is a perspective view of a second chained arrangement of systems according to embodiments of the present invention.
FIG. 86 is a side view of the configuration of FIG. 85.

Referring to FIGS. 85 and 86, a system 1780 according to embodiments of the present invention is a cascaded system that uses a single kinematic joint mechanism 1710 and a connection clamping link 1783. A primary system 1781 similar to system 1700 is supported by the kinematic joint mechanism 1710 and a secondary system 1782 similar to the system 1700 but without a distal tip actuation unit is coupled to the primary system 1781 by the connection clamping link 1783.

The clamping link 1783 may be made as to contain a slot at its ends such that the positioning of one drive system with respect to the other can be adjusted along the axial direction. The position may then be fixed using separate clamping screws 1784.

The system 1780 simplifies co-axial alignment of the primary and the secondary system. The system 1760 has the advantage that it offers freedom to mount the different systems independently.

Figure 87:
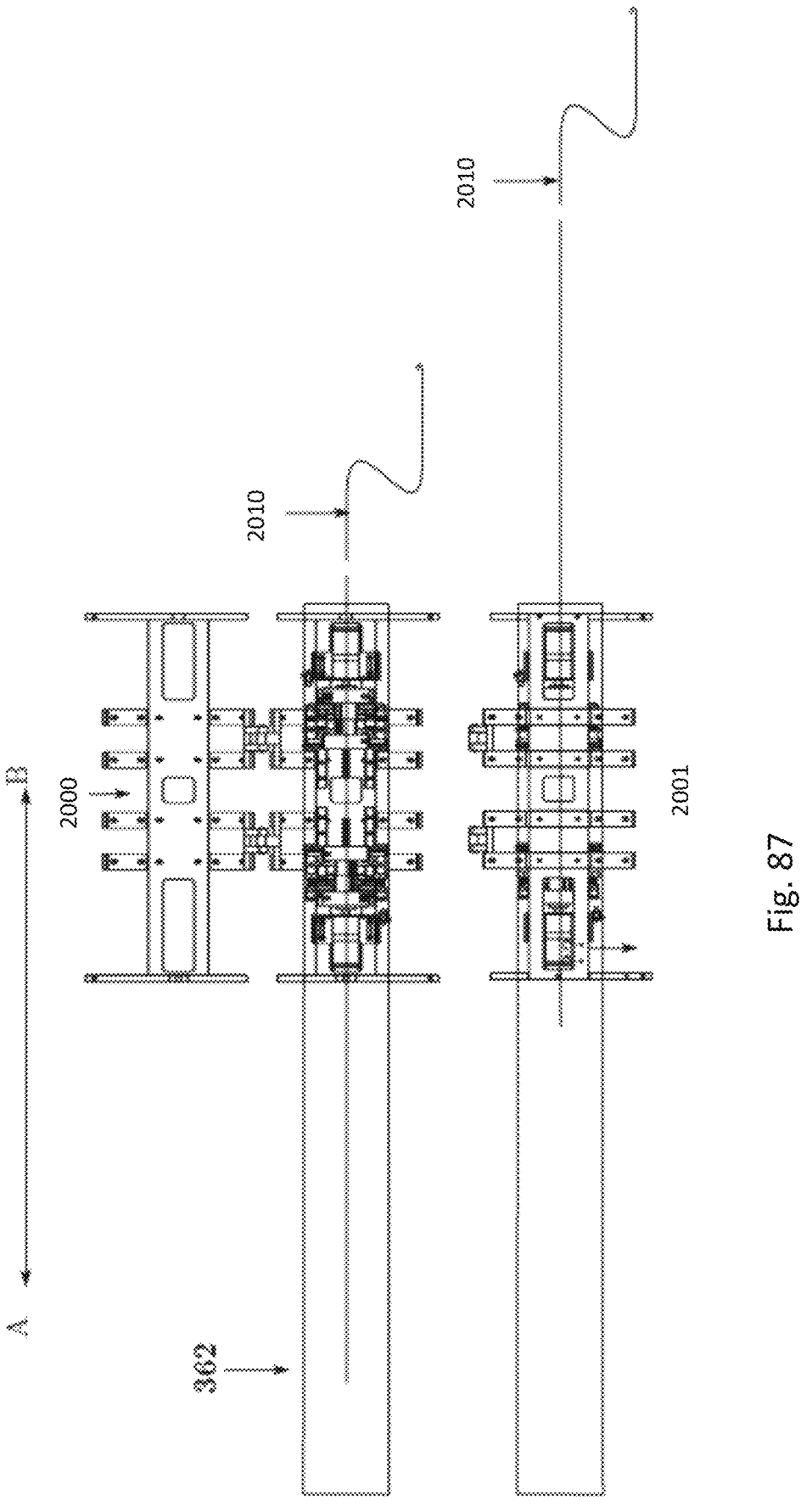
FIG. 87 is an illustration of configurations of a system according to embodiments of the present invention for a guide wire propulsion step.
Figure 88:
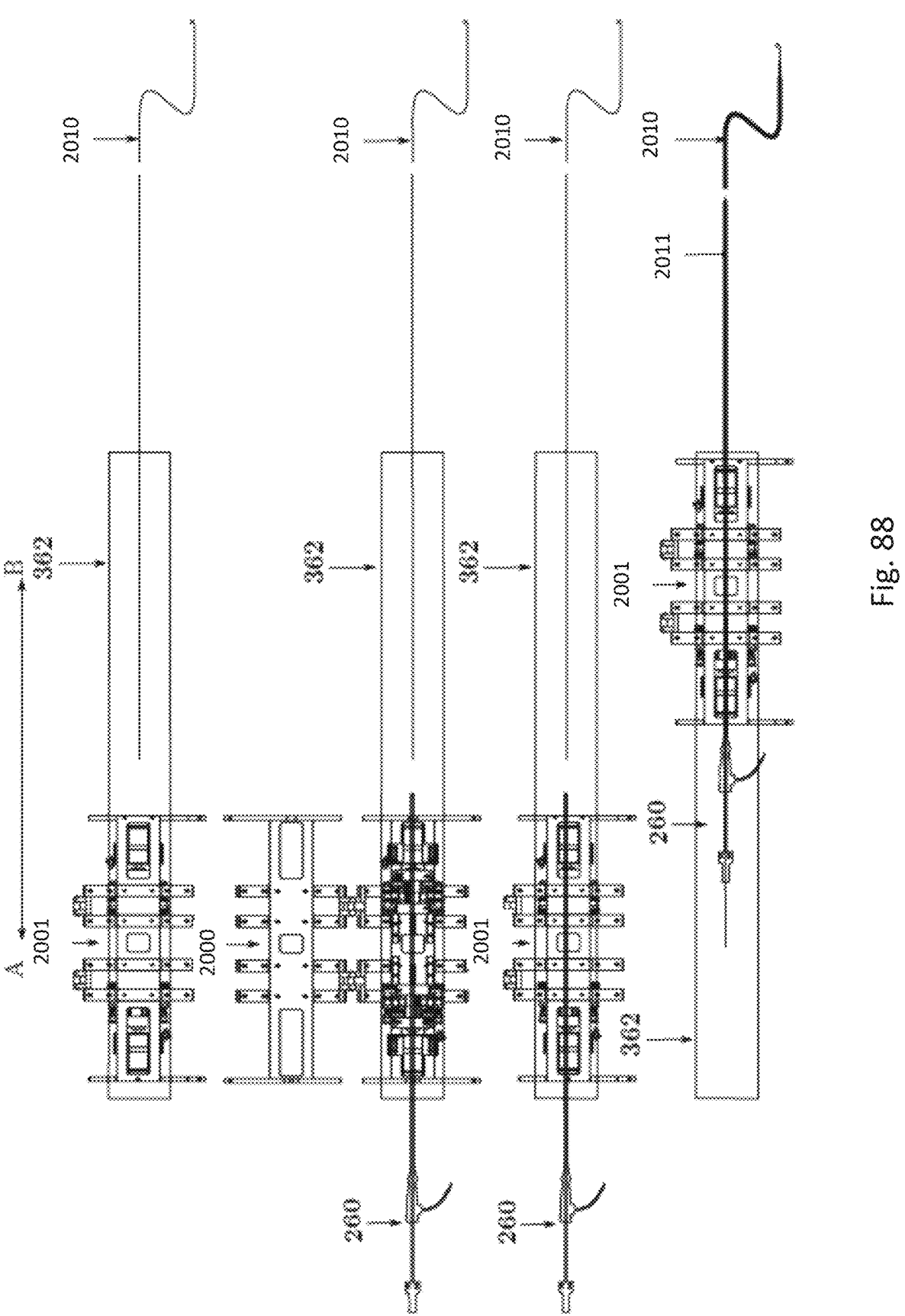
FIG. 88 is an illustration of configurations of a system according to embodiments of the present invention for a sheath propulsion step.
Figure 89:
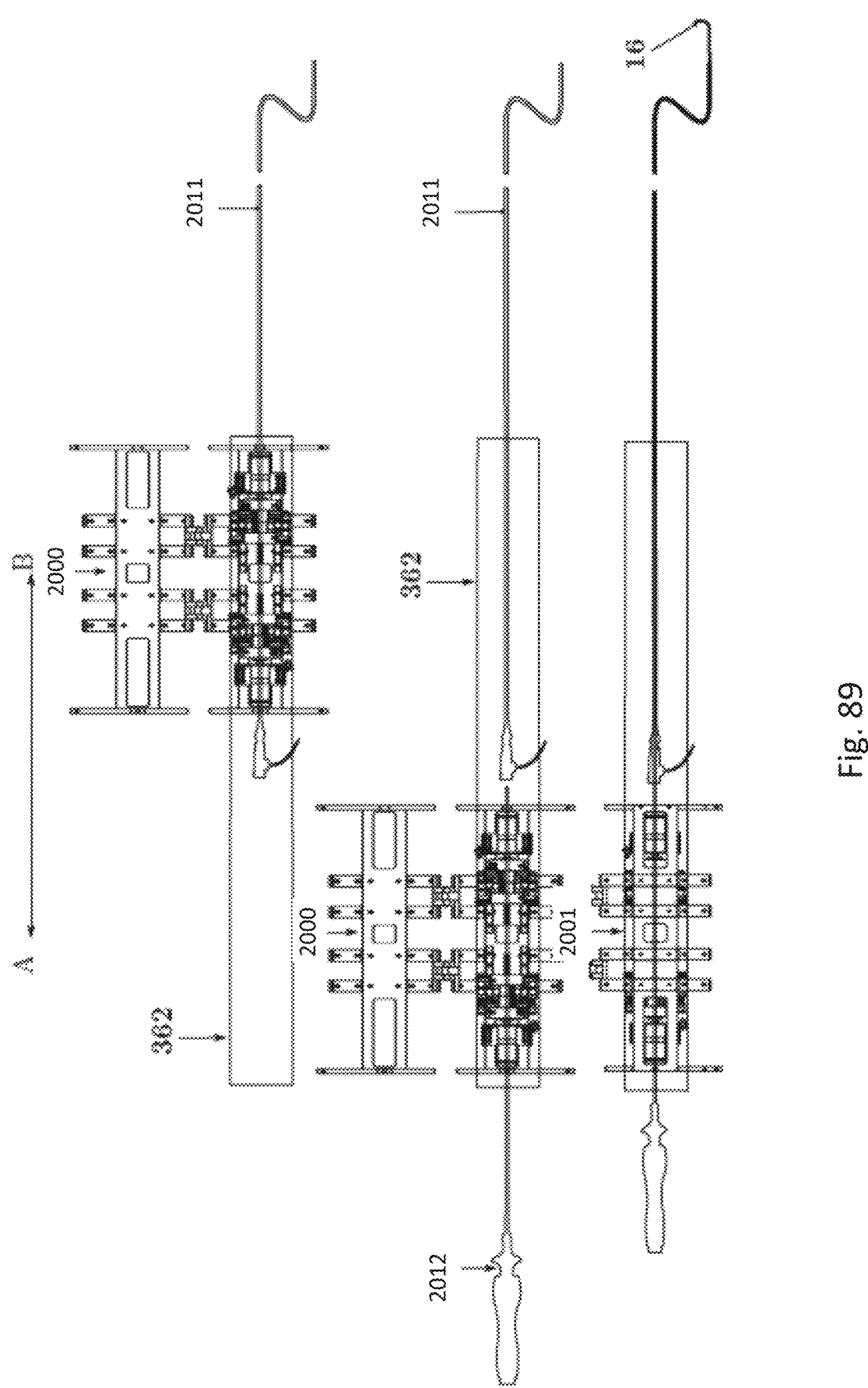
FIG. 89 is an illustration of configurations of a system according to embodiments of the present invention for a catheter propulsion step.

Referring to FIGS. 87 to 89, a fully automatic propulsion sequence using system 1300 is now described. The sequence comprises a guide wire propulsion stage, a sheath propulsion stage, and a catheter propulsion stage. In FIGS. 87 to 89, an open configuration of the system 1300 is indicated by 2000. A closed configuration of the system 1300 is indicated by 2001.

FIG. 87 provides an illustration of possible ways to use the system 1300 to achieve a fully automatic propulsion of the complete procedure for a guide wire propulsion step.

FIG. 88 provides an illustration of possible ways to use the system 1300 to achieve a fully automatic propulsion of the complete procedure in case of a sheath propulsion step.

FIG. 89 provides an illustration of possible ways to use the system 1300 to achieve a fully automatic propulsion of the complete procedure for a catheter propulsion step.

A possible sequence is as follows:

1 The needle is inserted into the vein by the surgeon
2 The system 1300 is translated to the position B using a translation stage
3 The system 1300 is opened
4 The guide wire 2010 is installed in the grippers
5 The system 1300 is closed
6 The system 1300 is actuated to insert the guide wire 2010 through the needle. Once the guide wire 2010 reaches the desired position, the grippers are left open.
7 The system 1300 is opened
8 The system 1300 is translated to the position A
9 The needle is removed
10 The sheath 2011 and the dilator are placed in the grippers
11 The system 1300 is closed
12 The system 1300 is translated to the position B and the sheath and the dilator are inserted over the guide wire
13 The system 1300 is actuated to insert the sheath and the dilator over the guide wire 2010 inside the body
14 Once the sheath is placed, the guide wire and the dilator are removed by the surgeon. The grippers are left open once the positioning is done.
15 The system 1300 is opened
16 The system 1300 is translated to the position A
17 The catheter 2012 is installed in the system 1300
18 The system 1300 is closed
19 The system 1300 is actuated to insert the catheter. The system 1300 will control the catheter position inside the heart in rotation, translation and bending.
20 Once the surgery is done, the catheter is retracted automatically with the actuation of the system 1300. The grippers are left open once the catheter is completely removed from the body.
21 The system 1300 is opened and the catheter is removed
22 The system 1300 is translated to the position B
23 The sheath is clamped on the grippers and is removed with system 1300.
24 The system 1300 is opened, and the sheath is removed for system 1300.

Figure 90:
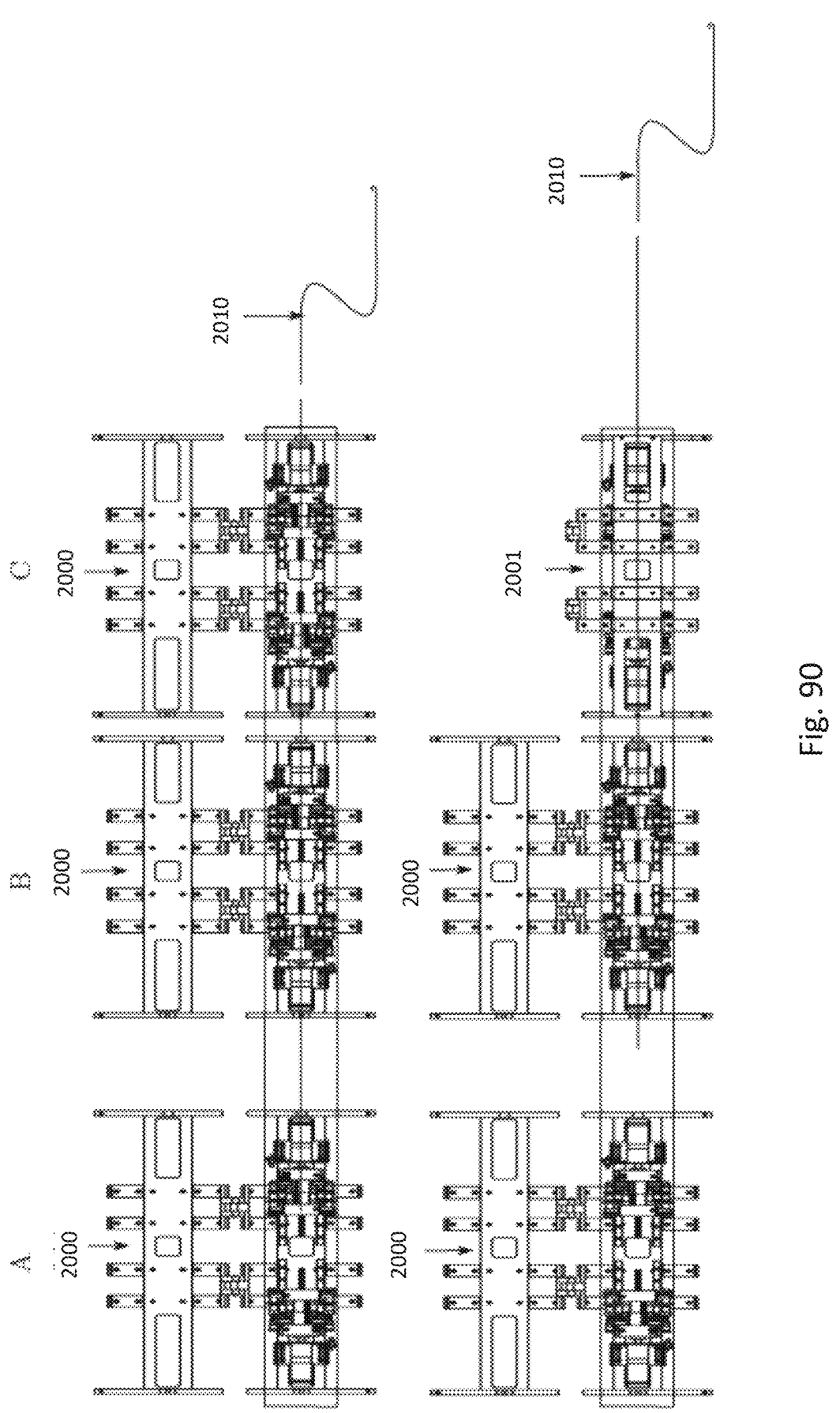
FIG. 90 is an illustration of configurations of a chained system according to embodiments of the present invention for a guide wire propulsion step.
Figure 91:
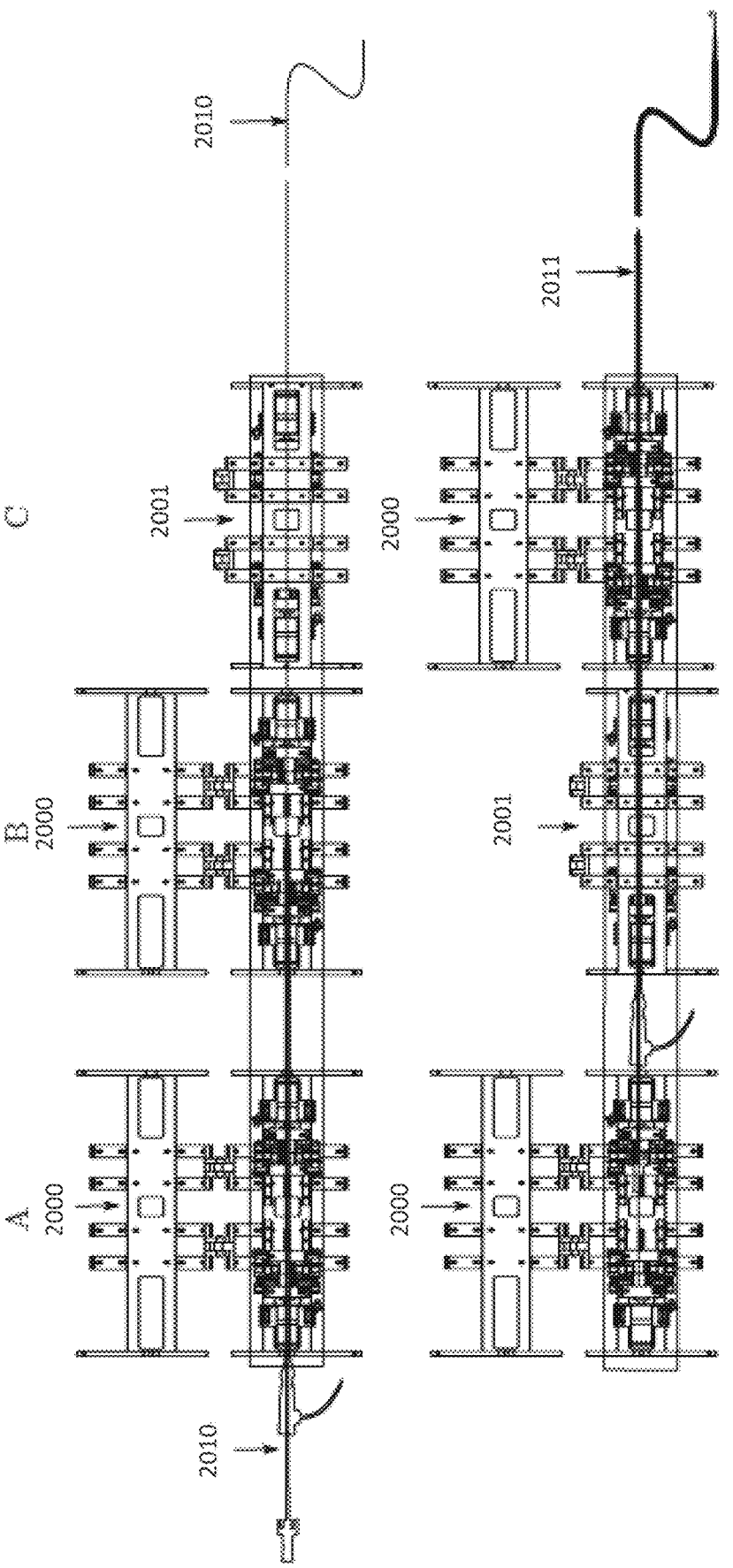
FIG. 91 is an illustration of configurations of a chained system according to embodiments of the present invention for a sheath propulsion step.
Figure 92:
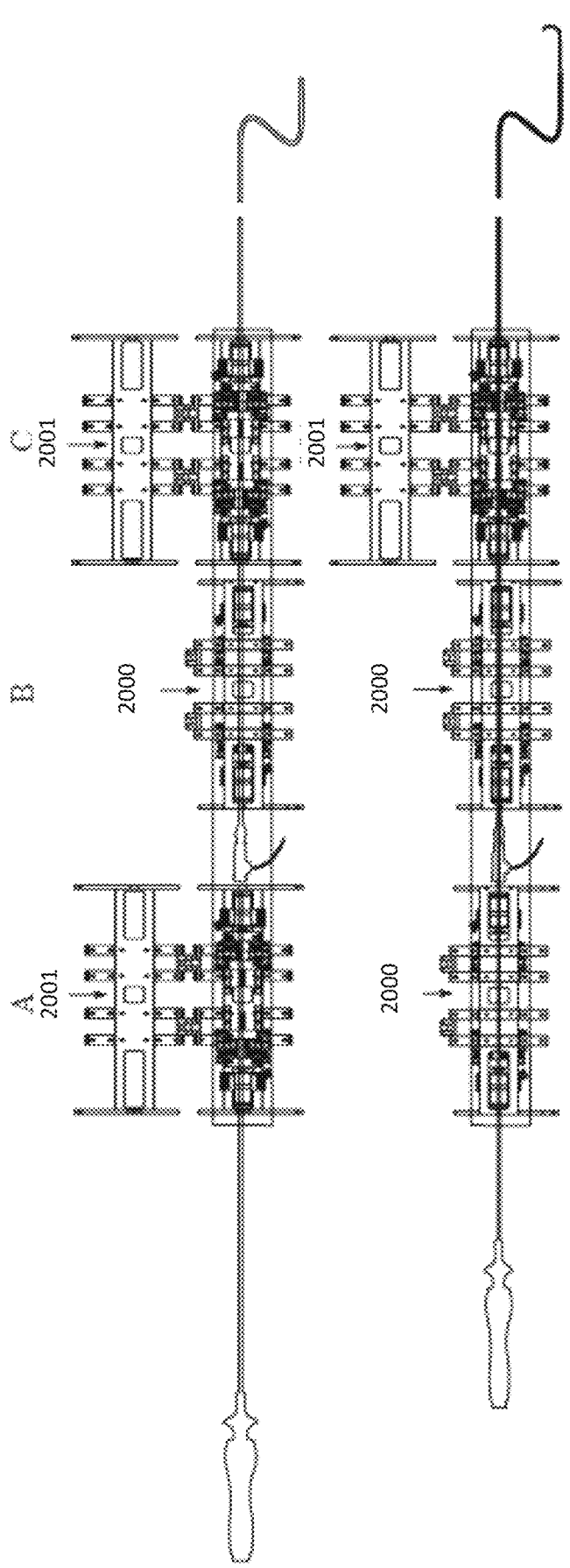
FIG. 92 is an illustration of configurations of a chained system according to embodiments of the present invention for a catheter propulsion step.

Referring to FIGS. 90 to 92, a fully automatic propulsion sequence using an apparatus comprising a chain of three systems 1100 is now described, for example in a configuration such as that shown in FIG. 84 or 86 with an additional system 1100 aligned with the other two systems. The sequence comprises a guide wire propulsion stage (FIG. 90), a sheath propulsion stage (FIG. 91), and a catheter propulsion stage (FIG. 92). In FIGS. 90 to 92, an open configuration of a system 1100 is indicated by 2000. A closed configuration of a system 1100 is indicated by 2001.

A possible sequence is as follows:

1 The needle is inserted into the vein by the surgeon
2 The three systems A, B, C are opened
3 The guide wire is installed in the grippers
4 The system C is closed
5 The apparatus is actuated to insert the guide wire 2010 through the needle. Once the guide wired reaches the desired position, the grippers are left open.
6 The system C is opened
7 The needle is removed
8 The sheath 2011 and the dilator are placed in the grippers of the system B
9 The system B is closed 10 The system B is actuated to insert the sheath and the dilator over the guide wire inside the body 11 Once the sheath is placed, the guide wire and the dilator are removed by the surgeon. The grippers are left close to ensure a precise positioning of the sheath.

12 The catheter 2012 is installed in the system A

13 The system A is closed

14 The apparatus is actuated to insert the catheter. The apparatus will control the catheter position inside the heart in rotation, translation and bending.

15 Once the surgery done, the catheter is retracted automatically with the actuation of the apparatus. The grippers are left open once the catheter is completely removed from the body.

16 The system A is opened, and the catheter is removed by the surgeon

17 The sheath is removed from the body with the system B.

18 The system B is opened, and the sheath is removed by the surgeon

Figure 70:
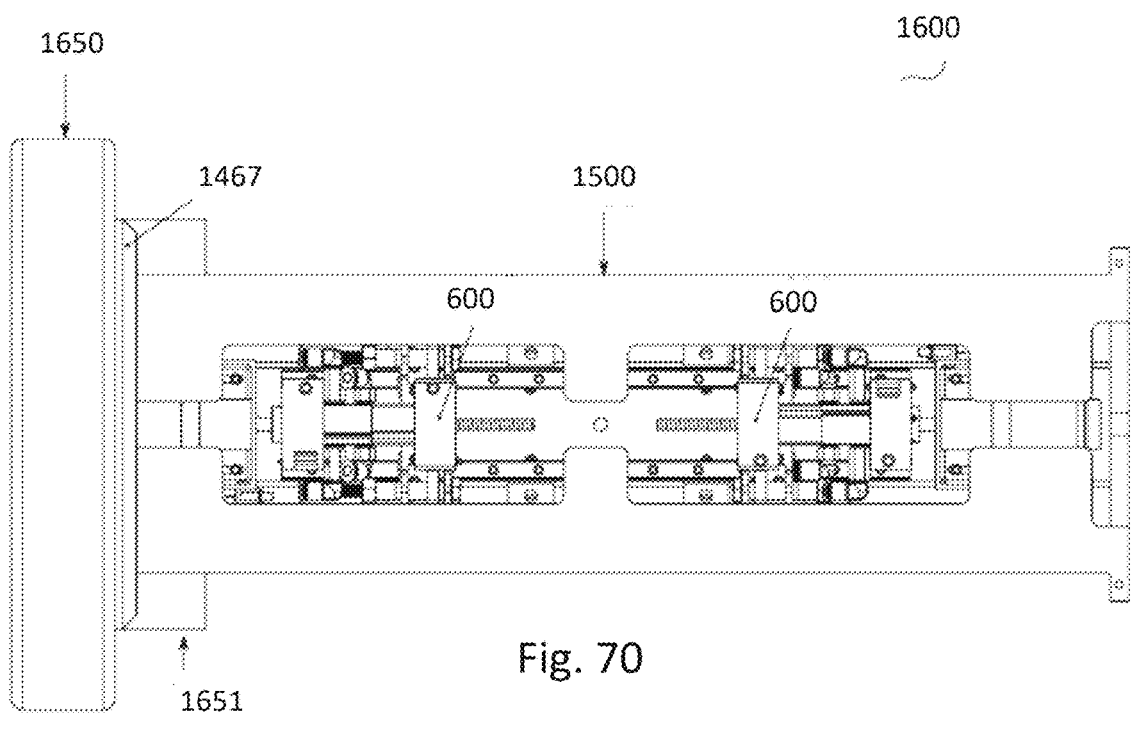
FIG. 70 is a plan view of the system of FIG. 68.

The embodiment 1600 of FIG. 70 can be opened if:

1 the frame of the linear module 1500 is in the initial horizontal orientation 2 the telescopic support slider 1304 is fully extended 3 the fixation screws 1328, 1329 embedded within the fixation blocks 1326, 1327 of the telescopic support slider 1304 are fully inserted and engaged with the frame 950 of the linear module 1500.

4 the frame of the rotary module 1650, the linear module 1500 and the rotating shaft 1125 are opened 5 the proximal and distal grippers 600 are opened 6 an embodiment of a catheter (or any tubular structure of the like) such catheter 1420 as shown in FIG. 58 within a sterile arrangement 1430 with drapes as as shown in FIG. 59 can be inserted within the modules of the drive system 1600.

7 the proximal and distal grippers 600 are closed 8 the frame of the rotary module 1650, the linear module 1500 and the rotating shaft 1125 are closed 9 the telescopic support slider 1304 is unscrewed and retracted.

The present invention is an open platform that can accommodate a broad range of commercially available catheters, guidewires, or other elongated medical devices or it can be used together with purposedly designed devices. Whereas a discrete set of sleeves would already offer a broad coverage of existing instruments, dedicated sleeves could be tailored to specific catheters or the like such as to optimize the compatibility and performance.

Modifications

It will be understood that a number of modifications of the embodiments described herein are possible within the scope of the present invention.

Embodiments of the present invention may comprise means for estimating an interaction force between the elongate member and the patient's anatomy. This information may be used advantageously to prevent tissue damage e.g. when excessively large forces are noticed which could indicate that the catheter is stuck, it may help at identifying the location of the instrument relatively to the anatomy e.g. informing about contact state or even relative location which may help during control or decision-making by the physician.

Embodiments of the present invention may comprise a force sensor, for example integrated into the mounting piece 771 (FIG. 29) between spindle and the gripper. A simple 1-degree of freedom force sensor e.g. based on strain-gages may be used which is capable of measuring the propulsion force delivered by a gripper upon an elongate member.

In some embodiments the driving force may be estimated indirectly e.g. via measurement of certain displacement of a flexible structure, e.g. introduced between the driving motor and the sleeve, from observing the extension of the sleeve or any other means.

Part of the force that is imparted by the driver upon the elongate member such as a catheter or guidewire may be taken up as friction at an entry port (cannula) into a patint, part may be taken up by the friction between the catheter and a guiding sheet, part may be taken up by the interaction of the elongate member with the anatomy. To obtain a better understanding of the latter, one particular embodiment of the invention includes an external force sensor or sensing method that is interfaced with the cannula or the guiding sheath and that directly measures the force applied by catheter on these additional bodies. By subtracting the estimated friction forces on these bodies from the driving force a more accurate estimate of the interaction force between the catheter and target anatomy can be obtained.

To improve the estimation of the interaction force at the tip of the elongate member one may also combine measurements of the drive system (displacements, forces, accelerations etc), with external measurements and/or medical data to estimate the distributed interaction force along the catheter body and more effectively isolate and estimate the tip interaction forces.

In some embodiments the propulsion and retraction mechanism is implemented through a pair of pneumatic cylinders or through any other non-magnetic drive approach. The rotation about the longitudinal direction can also be implemented in such a manner, for example, but not limited to, a pneumatic cylinder that drives a rack. In some embodiments a hollow pinion is rigidly connected to the frame 950 and aligned so that its axis coincides with the longitudinal axis of the outer frame and of the catheter or other elongate member. Upon displacement of the cylinder and the rack connected to it, the pinion which is engaged with the rack, rotates about its own axis and at the same time controls the rotation of the frame and catheter about their respective rotation axis. Such an embodiment provides a compact catheter drive system which can be used in the vicinity of an MRI system. By excluding use of ferro-magnetic materials, the embodiment can be used together with the MRI machine in such a way that the drive system would not interfere with the MRI machine and would hence not negatively affect the quality of the MRI scans. Along similar lines the working of the MRI machine would not negatively affect the functioning of the catheter drive system. Hence the resulting embodiment would be fully MRI-compatible.

The sleeve may be configured to increase in diameter when the ends of the sleeve are moved towards each other and to decrease in diameter when the ends of the sleeve are moved away from each other. For example the sleeve may have accordion-like behaviour, such that it expands radially when the ends are moved further apart and contracts radially when the ends are moved closer. With only one sleeve diameter a range of different elongate members can be manipulated.

Whereas in the above description, embodiments were described wherein the gripper firmly grips the elongated body such that the elongated body does not slip and that at such point the gripper is displaced to displace the elongated body by an equal amount, in other embodiments of the present invention grippers are envisaged for other applications whereby the body is gripped in such a way that some amount of slip is intentionally realized. In fact the resistance to movement of the elongated body may be controlled, allowing a certain displacement as function of an external force that is applied.

According to some embodiments, for some applications, slip is desirable, even when lower forces are applied. For example, a haptic feedback system for rendering controllable resistance forces for simulating the behaviour when introducing elongated bodies into natural lumens. Such embodiments may be used for training colonoscopy, hysteroscopy, or catheter procedures. The user would then manipulate the elongated body and as he/she inserts it into the in-silico trainer where one would deform the lumen more or less (by extending/contracting the sleeve) to generate a resistance force. Rotation of the sleeve could be done to inflict torques upon the surgical instrument.

The invention claimed is:

1. A device for manipulation of an elongate member, the device comprising:
   at least one gripper including:
      a flexible sleeve for receiving the elongate member, the sleeve extending along a sleeve axis and having first and second opposite ends, the sleeve being a stretchable tubular sleeve;
      a first clamping element configured to receive and removably couple to the first end of the sleeve; and
      a second clamping element configured to receive and removably couple to the second end of the sleeve; and;
   a driving element coupled to the first clamping element and to the second clamping element
   at least one sensor; and
   a control element configured to receive data from the at least one sensor and to provide a control signal to the driving element in dependence upon the received data;
   wherein spacing between the first and second clamping elements can be controlled for causing a difference of sleeve width by stretching the sleeve and gripping the elongate member;
   wherein the sleeve has a first width at a first location when the first and second clamping elements have a first spacing along the sleeve axis and a second width at the first location when the first and second clamping elements have a second spacing along the sleeve axis which is less than the first spacing; and
   wherein the first width is different to the second width, and
   wherein at least one of the first clamping element and the second clamping element is adapted for being arranged:
      in an open configuration providing at least sideways access for inserting the sleeve sideways in a direction not along a sleeve axis direction in said at least one clamping element, and
      in a closed configuration when the sleeve is clamped.

2. The device according to claim 1, wherein the sleeve is configured to engage with a surface of the elongate member for a specified spacing of the first and second clamping elements.

3. The device according to claim 1, wherein in the open configuration the first clamping element and/or the second clamping element comprises an opening along its circumference.

4. The device according to claim 1, wherein at least one of the first clamping element and the second clamping element is configured to receive the sleeve in a direction substantially perpendicular to the sleeve axis or wherein at least one of the first clamping element and the second clamping element is configured to also receive the sleeve in a direction substantially parallel to the sleeve axis.

5. The device according to claim 1, wherein the first clamping element is rotatable about the sleeve axis relative to the second clamping element or wherein the second clamping element is rotatable about the sleeve axis relative to the first clamping element.

6. The device according to claim 1, wherein the first clamping element has an open-ended elongate form or wherein the second clamping element has an open-ended elongate form.

7. The device according to claim 1, wherein the first clamping element comprises an aperture for receiving the sleeve, the aperture extending parallel to the axis of the first clamping element or wherein the second clamping element comprises an aperture for receiving the sleeve, the aperture extending parallel to the axis of the first clamping element.

8. The device according to claim 1, wherein at least one of the first clamping element and the second clamping element comprises first and second portions coupled by a hinge.

9. The device according to claim 1, wherein the sleeve comprises a first collar at the first end of the sleeve and a second collar at the second end of the sleeve,
   wherein the first clamping element is configured to couple to the first collar and the second clamping element is configured to couple to the second collar.

10. The device according to claim 1, wherein the elongated member is any of a catheter or an endoscope.

11. The device according to claim 1,
   wherein the driving element is configured to control the spacing of the first clamping element and the second clamping element along the sleeve axis, or
   wherein the driving element is configured to rotate the first clamping element about the sleeve axis, or
   wherein the driving element is configured to rotate the second clamping element about the sleeve axis.

12. The device according to claim 1, wherein the driving element is configured to rotate the second clamping element about the sleeve axis.

13. The device according to claim 1, comprising another gripper, the grippers being spaced apart along the sleeve axis.

14. The device according to claim 1 comprising a sterile barrier for separating the elongate member at an interior of the sleeve and an exterior of the sleeve.

* * * * *